US012577324B2

(12) United States Patent
Pelegrin et al.

(10) Patent No.: US 12,577,324 B2
(45) Date of Patent: Mar. 17, 2026

(54) ANTIBODIES HAVING SPECIFICITY TO HER4 AND USES THEREOF

(71) Applicants:INSERM (INSTITUT NATIONAL DE LA SANTÉ ET DE LA RECHERCHE MÉDICALE), Paris (FR); INSTITUT RÉGIONAL DU CANCER DE MONTPELLIER, Montpellier (FR); UNIVERSITÉ DE MONTPELLIER, Montpellier (FR)

(72) Inventors: Andre Pelegrin, Montpellier Cedex (FR); Pierre Martineau, Montpellier Cedex (FR); Thierry Chardes, Montpellier Cedex (FR); Romain Lanotte, Calvisson (FR)

(73) Assignees: INSERM (INSTITUT NATIONAL DE LA SANTE ET DE LA RECHERCHE MEDICALE), Paris (FR); INSTITUT RÉGIONAL DU CANCER DE MONTPELLIER, Montpellier (FR); UNIVERSITÉ DE MONTPELLIER, Montpellier (FR)

( * ) Notice: Subject to any disclaimer, the term of this patent is extended or adjusted under 35 U.S.C. 154(b) by 887 days.

(21) Appl. No.: 17/783,182

(22) PCT Filed: Dec. 8, 2020

(86) PCT No.: PCT/EP2020/085118
§ 371 (c)(1),
(2) Date: Jun. 7, 2022

(87) PCT Pub. No.: WO2021/116119
PCT Pub. Date: Jun. 17, 2021

(65) Prior Publication Data
US 2023/0040928 A1 Feb. 9, 2023

(30) Foreign Application Priority Data

Dec. 9, 2019 (EP) .................................... 19306608

(51) Int. Cl.
| | |
|---|---|
| *C07K 16/32* | (2006.01) |
| *A61K 39/00* | (2006.01) |
| *A61K 39/395* | (2006.01) |
| *A61K 47/68* | (2017.01) |
| *A61P 15/00* | (2006.01) |
| *A61P 35/00* | (2006.01) |
| *C12N 15/00* | (2006.01) |
| *C12N 15/13* | (2006.01) |

(52) U.S. Cl.
CPC .............. *C07K 16/32* (2013.01); *A61K 39/00* (2013.01); *A61K 47/6817* (2017.08); *A61K 47/6869* (2017.08); *A61P 15/00* (2018.01); *A61P 35/00* (2018.01); *A61K 39/395* (2013.01); *A61K 2039/505* (2013.01); *C07K 2317/21* (2013.01); *C07K 2317/24* (2013.01); *C07K 2317/565* (2013.01); *C07K 2317/73* (2013.01); *C07K 2317/76* (2013.01); *C12N 15/00* (2013.01)

(58) Field of Classification Search
CPC ............ A61K 47/6817; A61K 47/6869; A61K 2039/505; A61P 15/00; A61P 35/00; C07K 16/32; C07K 2317/21; C07K 2317/24; C07K 2317/565; C07K 2317/622; C07K 2317/73; C07K 2317/75; C07K 2317/76
See application file for complete search history.

(56) References Cited

U.S. PATENT DOCUMENTS

2002/0119148 A1 * 8/2002 Gerritsen ........... C07K 14/4756
424/143.1

OTHER PUBLICATIONS

Almagro et al., Frontiers in Immunology, 2018, 8: 1751, pp. 1-19.*
Herold et al., Science Reports, 2017, 7(1):12276, pp. 1-17.*
Murphy et al., Journal of Immunological Methods, 2018, 463: 127-133.*
Berglund et al., Protein Science, 2008, 17:606-613.*
Greenspan et al., Nature Biotechnology, 1999, 7: 936-937.*
Vered Kunik et al, "Structural Consensus among Antibodies Defines the Antigen Binding Site", PLOS Computational Biology, vol. 8, No. 2, Feb. 23, 2012 (Feb. 23, 2012), p. e1002388.
Jollmen M et al, "Suppression of breast cancer cell growth by a monoclonal antibody targeting cleavable ErbB4 soforms", Mar. 1, 2009 (Mar. 1, 2009), vol. 28, No. 10, p. 1309-1319.
Shogo Okazaki et al., "Development of an ErbB4 monoclonal antibody that blocks neuregulin-1-induced ErbB4 activation in cancer cells", Biochemical and Biophysical Research Communications, vol. 470, No. 1, Jan. 1, 2016 (Jan. 1, 2016), p. 239-244.

* cited by examiner

*Primary Examiner* — Hong Sang
(74) *Attorney, Agent, or Firm* — WCF IP

(57) ABSTRACT

The present invention relates to antibodies having specificity to HER4 and uses thereof, which are able to induce biased 4ICD routing/signaling. The inventors have isolated by antibody phage display three fully human anti-HER4 single-chain variable antibody fragment (scFv), selected on human HER4 extracellular domain, referred as C6 mAb, D5 mAb and F4 mAb and one fully human anti-HER4 scFv named H2 mAb, selected on NRG 1β1-stimulated EGFR/HER4 JMaCYT1-transfected NIH3T3 cells. In particular, the present invention relates to an isolated anti-HER4 antibody, wherein said antibody binds to an epitope of the HER4 protein.

16 Claims, 3 Drawing Sheets
Specification includes a Sequence Listing.

SEQUENCE LISTING

<160> NUMBER OF SEQ ID NOS: 33

<210> SEQ ID NO 1
<211> LENGTH: 121
<212> TYPE: PRT
<213> ORGANISM: Artificial Sequence
<220> FEATURE:
<223> OTHER INFORMATION: Synthetic C6 mAb VH

<400> SEQUENCE: 1

```
Glu Val Gln Leu Val Glu Ser Gly Gly Ser Leu Val Lys Pro Gly Gly
1               5                   10                  15

Ser Leu Arg Leu Ser Cys Ala Ala Ser Gly Phe Thr Phe Ser Asn Tyr
            20                  25                  30

Tyr Met Asn Trp Val Arg Gln Ala Pro Gly Lys Gly Leu Glu Trp Ile
        35                  40                  45

Ser Ser Ile Ser Gly Ser Ser Arg Tyr Ile Asp Tyr Ala Asp Phe Val
    50                  55                  60

Lys Gly Arg Phe Thr Ile Ser Arg Asp Asn Ala Thr Asn Ser Leu Tyr
65                  70                  75                  80

Leu Gln Met Asn Ser Leu Arg Ala Glu Asp Thr Ala Val Tyr Tyr Cys
                85                  90                  95

Val Arg Ser Ser Ser Asp Tyr Phe Gly Gly Gly Met Asp Val Trp Gly
            100                 105                 110

Arg Gly Thr Leu Val Thr Val Ser Ser
        115                 120
```

```
<210> SEQ ID NO 2
<211> LENGTH: 8
<212> TYPE: PRT
<213> ORGANISM: Artificial Sequence
<220> FEATURE:
<223> OTHER INFORMATION: Synthetic C6 mAb H-CDR1

<400> SEQUENCE: 2

Gly Phe Thr Phe Ser Asn Tyr Tyr
1               5
```

```
<210> SEQ ID NO 3
<211> LENGTH: 8
<212> TYPE: PRT
<213> ORGANISM: Artificial Sequence
<220> FEATURE:
<223> OTHER INFORMATION: Synthetic C6 mAb H-CDR2

<400> SEQUENCE: 3

Ile Ser Gly Ser Ser Arg Tyr Ile
1               5
```

```
<210> SEQ ID NO 4
<211> LENGTH: 14
<212> TYPE: PRT
<213> ORGANISM: Artificial Sequence
<220> FEATURE:
<223> OTHER INFORMATION: Synthetic C6 mAb H-CDR3

<400> SEQUENCE: 4

Val Arg Ser Ser Ser Asp Tyr Phe Gly Gly Gly Met Asp Val
1               5                   10
```

```
<210> SEQ ID NO 5
<211> LENGTH: 111
<212> TYPE: PRT
<213> ORGANISM: Artificial Sequence
<220> FEATURE:
<223> OTHER INFORMATION: Synthetic C6 mAb VL

<400> SEQUENCE: 5

Gln Ser Val Leu Thr Gln Pro Ala Ser Val Ser Gly Ser Pro Gly Gln
1               5                   10                  15

Ser Ile Thr Ile Ser Cys Ala Gly Thr Ser Ser Asp Val Gly Gly Ser
            20                  25                  30
```

```
Tyr Tyr Val Ser Trp Tyr Gln Gln His Pro Gly Lys Ala Pro Lys Leu
        35              40              45

Met Ile Tyr Tyr Asp Ser Tyr Arg Pro Ser Gly Val Ser Asn Arg Phe
    50              55              60

Ser Gly Ser Lys Ser Gly Asn Thr Ala Ser Leu Thr Ile Ser Gly Leu
65              70              75              80

Gln Ala Glu Asp Glu Ala Asp Tyr Tyr Cys Ser Ser Ser Thr Tyr Asn
                85              90              95

Ser Thr Arg Val Phe Gly Gly Gly Thr Lys Leu Ala Val Leu Gly
            100             105             110
```

```
<210> SEQ ID NO 6
<211> LENGTH: 9
<212> TYPE: PRT
<213> ORGANISM: Artificial Sequence
<220> FEATURE:
<223> OTHER INFORMATION: Synthetic C6 mAb L-CDR1

<400> SEQUENCE: 6

Ser Ser Asp Val Gly Gly Ser Tyr Tyr
1               5
```

```
<210> SEQ ID NO 7
<211> LENGTH: 3
<212> TYPE: PRT
<213> ORGANISM: Artificial Sequence
<220> FEATURE:
<223> OTHER INFORMATION: Synthetic C6 mAb L-CDR2

<400> SEQUENCE: 7

Tyr Asp Ser
1
```

```
<210> SEQ ID NO 8
<211> LENGTH: 10
<212> TYPE: PRT
<213> ORGANISM: Artificial Sequence
<220> FEATURE:
<223> OTHER INFORMATION: Synthetic C6 mAb L-CDR3

<400> SEQUENCE: 8

Ser Ser Ser Thr Tyr Asn Ser Thr Arg Val
1               5               10
```

```
<210> SEQ ID NO 9
<211> LENGTH: 121
<212> TYPE: PRT
<213> ORGANISM: Artificial Sequence
<220> FEATURE:
<223> OTHER INFORMATION: Synthetic D5 mAb VH

<400> SEQUENCE: 9

Glu Val Gln Leu Val Glu Ser Gly Gly Ser Leu Val Lys Pro Gly Gly
1               5               10              15

Ser Leu Arg Leu Ser Cys Ala Ala Ser Gly Phe Thr Phe Ser Asn Tyr
            20              25              30

Tyr Met Asn Trp Val Arg Gln Ala Pro Gly Lys Gly Leu Glu Trp Ile
        35              40              45

Ser Ser Ile Asp Gly Ser Ser Arg Tyr Ile Asp Tyr Ala Asp Phe Val
    50              55              60

Lys Gly Arg Phe Thr Ile Ser Arg Asp Asn Ala Thr Asn Ser Leu Tyr
65              70              75              80
```

```
Leu Gln Met Asn Ser Leu Arg Ala Glu Asp Thr Ala Val Tyr Tyr Cys
                85                  90                  95

Val Arg Ser Ser Ser Asp Tyr Phe Gly Gly Gly Met Asp Val Trp Gly
            100                 105                 110

Arg Gly Thr Leu Val Thr Val Ser Ser
        115                 120

<210> SEQ ID NO 10
<211> LENGTH: 8
<212> TYPE: PRT
<213> ORGANISM: Artificial Sequence
<220> FEATURE:
<223> OTHER INFORMATION: Synthetic D5 mAb H-CDR1

<400> SEQUENCE: 10

Gly Phe Thr Phe Ser Asn Tyr Tyr
1               5

<210> SEQ ID NO 11
<211> LENGTH: 8
<212> TYPE: PRT
<213> ORGANISM: Artificial Sequence
<220> FEATURE:
<223> OTHER INFORMATION: Synthetic D5 mAb H-CDR2

<400> SEQUENCE: 11

Ile Asp Gly Ser Ser Arg Tyr Ile
1               5

<210> SEQ ID NO 12
<211> LENGTH: 14
<212> TYPE: PRT
<213> ORGANISM: Artificial Sequence
<220> FEATURE:
<223> OTHER INFORMATION: Synthetic D5 mAb H-CDR3

<400> SEQUENCE: 12

Val Arg Ser Ser Ser Asp Tyr Phe Gly Gly Gly Met Asp Val
1               5                   10

<210> SEQ ID NO 13
<211> LENGTH: 111
<212> TYPE: PRT
<213> ORGANISM: Artificial Sequence
<220> FEATURE:
<223> OTHER INFORMATION: Synthetic D5 mAb VL

<400> SEQUENCE: 13

Gln Ser Val Leu Thr Gln Pro Ala Ser Val Ser Gly Ser Pro Gly Gln
1               5                   10                  15

Ser Ile Thr Ile Ser Cys Ala Gly Thr Ser Ser Asp Val Gly Gly Ser
            20                  25                  30

Ser Tyr Val Ser Trp Tyr Gln Gln His Pro Gly Lys Ala Pro Lys Leu
        35                  40                  45

Met Ile Tyr Tyr Asp Ser Tyr Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Asn Thr Tyr Tyr
                85                  90                  95

Ser Thr Arg Val Phe Gly Gly Gly Thr Lys Leu Ala Val Leu Gly
            100                 105                 110
```

<210> SEQ ID NO 14
<211> LENGTH: 9
<212> TYPE: PRT
<213> ORGANISM: Artificial Sequence
<220> FEATURE:
<223> OTHER INFORMATION: Synthetic D5 mAb L-CDR1

<400> SEQUENCE: 14

Ser Ser Asp Val Gly Gly Ser Ser Tyr
1               5

<210> SEQ ID NO 15
<211> LENGTH: 3
<212> TYPE: PRT
<213> ORGANISM: Artificial Sequence
<220> FEATURE:
<223> OTHER INFORMATION: Synthetic SEQ ID NO: 16

<400> SEQUENCE: 15

Tyr Asp Ser
1

<210> SEQ ID NO 16
<211> LENGTH: 10
<212> TYPE: PRT
<213> ORGANISM: Artificial Sequence
<220> FEATURE:
<223> OTHER INFORMATION: Synthetic D5 mAb  L-CDR3

<400> SEQUENCE: 16

Ser Ser Asn Thr Tyr Tyr Ser Thr Arg Val
1               5                   10

<210> SEQ ID NO 17
<211> LENGTH: 121
<212> TYPE: PRT
<213> ORGANISM: Artificial Sequence
<220> FEATURE:
<223> OTHER INFORMATION: Synthetic F4 mAb VH

<400> SEQUENCE: 17

Glu Val Gln Leu Val Glu Ser Gly Gly Ser Leu Val Lys Pro Gly Gly
1               5                   10                  15

Ser Leu Arg Leu Ser Cys Ala Ala Ser Gly Phe Thr Phe Ser Asn Asn
            20                  25                  30

Asp Met Asn Trp Val Arg Gln Ala Pro Gly Lys Gly Leu Glu Trp Ile
        35                  40                  45

Ser Ser Ile Ser Gly Ser Ser Arg Tyr Ile Asn Tyr Ala Asp Phe Val
    50                  55                  60

Lys Gly Arg Phe Thr Ile Ser Arg Asp Asn Ala Thr Asn Ser Leu Tyr
65                  70                  75                  80

Leu Gln Met Asn Ser Leu Arg Ala Glu Asp Thr Ala Val Tyr Tyr Cys
                85                  90                  95

Val Arg Ser Ser Asp Asp Tyr Phe Gly Gly Gly Met Asp Val Trp Gly
            100                 105                 110

Arg Gly Thr Leu Val Thr Val Ser Ser
        115                 120

<210> SEQ ID NO 18
<211> LENGTH: 8
<212> TYPE: PRT
<213> ORGANISM: Artificial Sequence
<220> FEATURE:

<223> OTHER INFORMATION: Synthetic F4 mAb H-CDR1

<400> SEQUENCE: 18

Gly Phe Thr Phe Ser Asn Asn Asp
1               5

<210> SEQ ID NO 19
<211> LENGTH: 8
<212> TYPE: PRT
<213> ORGANISM: Artificial Sequence
<220> FEATURE:
<223> OTHER INFORMATION: Synthetic F4 mAb H-CDR2

<400> SEQUENCE: 19

Ile Ser Gly Ser Ser Arg Tyr Ile
1               5

<210> SEQ ID NO 20
<211> LENGTH: 14
<212> TYPE: PRT
<213> ORGANISM: Artificial Sequence
<220> FEATURE:
<223> OTHER INFORMATION: Synthetic F4 mAb H-CDR3

<400> SEQUENCE: 20

Val Arg Ser Ser Asp Asp Tyr Phe Gly Gly Gly Met Asp Val
1               5                   10

<210> SEQ ID NO 21
<211> LENGTH: 111
<212> TYPE: PRT
<213> ORGANISM: Artificial Sequence
<220> FEATURE:
<223> OTHER INFORMATION: Synthetic F4 mAb VL

<400> SEQUENCE: 21

Gln Ser Val Leu Thr Gln Pro Ala Ser Val Ser Gly Ser Pro Gly Gln
1               5                   10                  15

Ser Ile Thr Ile Ser Cys Ala Gly Thr Ser Ser Asp Val Gly Gly Tyr
                20                  25                  30

Ser Gly Val Ser Trp Tyr Gln Gln His Pro Gly Lys Ala Pro Lys Leu
        35                  40                  45

Met Ile Tyr Asn Asp Ser Tyr Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Asn Asn
                85                  90                  95

Ser Thr Arg Val Phe Gly Gly Gly Thr Lys Leu Ala Val Leu Gly
            100                 105                 110

<210> SEQ ID NO 22
<211> LENGTH: 9
<212> TYPE: PRT
<213> ORGANISM: Artificial Sequence
<220> FEATURE:
<223> OTHER INFORMATION: Synthetic F4 mAb L-CDR1

<400> SEQUENCE: 22

Ser Ser Asp Val Gly Gly Tyr Ser Gly
1               5

<210> SEQ ID NO 23

```
<211> LENGTH: 3
<212> TYPE: PRT
<213> ORGANISM: Artificial Sequence
<220> FEATURE:
<223> OTHER INFORMATION: Synthetic F4 mAb L-CDR2

<400> SEQUENCE: 23

Asn Asp Ser
1

<210> SEQ ID NO 24
<211> LENGTH: 10
<212> TYPE: PRT
<213> ORGANISM: Artificial Sequence
<220> FEATURE:
<223> OTHER INFORMATION: Synthetic F4 mAb L-CDR3

<400> SEQUENCE: 24

Ser Ser Tyr Thr Asn Asn Ser Thr Arg Val
1               5                   10

<210> SEQ ID NO 25
<211> LENGTH: 121
<212> TYPE: PRT
<213> ORGANISM: Artificial Sequence
<220> FEATURE:
<223> OTHER INFORMATION: Synthetic H2 mAb VH

<400> SEQUENCE: 25

Glu Val Gln Leu Val Glu Ser Gly Gly Ser Leu Val Lys Pro Gly Gly
1               5                   10                  15

Ser Leu Arg Leu Ser Cys Ala Ala Ser Gly Phe Thr Phe Ser Asn Asn
            20                  25                  30

Asp Met Asn Trp Val Arg Gln Ala Pro Gly Lys Gly Leu Glu Trp Ile
        35                  40                  45

Ser Asp Ile Asn Gly Ser Ser Arg Tyr Ile Tyr Tyr Ala Asp Phe Val
    50                  55                  60

Lys Gly Arg Phe Thr Ile Ser Arg Asp Asn Ala Thr Asn Ser Leu Tyr
65                  70                  75                  80

Leu Gln Met Asn Ser Leu Arg Ala Glu Asp Thr Ala Val Tyr Tyr Cys
                85                  90                  95

Val Arg Ser Ser Asp Asp Tyr Phe Gly Gly Gly Met Asp Val Trp Gly
            100                 105                 110

Arg Gly Thr Leu Val Thr Val Ser Ser
        115                 120

<210> SEQ ID NO 26
<211> LENGTH: 8
<212> TYPE: PRT
<213> ORGANISM: Artificial Sequence
<220> FEATURE:
<223> OTHER INFORMATION: Synthetic H2 mAb H-CDR1

<400> SEQUENCE: 26

Gly Phe Thr Phe Ser Asn Asn Asp
1               5

<210> SEQ ID NO 27
<211> LENGTH: 8
<212> TYPE: PRT
<213> ORGANISM: Artificial Sequence
<220> FEATURE:
<223> OTHER INFORMATION: Synthetic H2 mAb H-CDR2
```

```
<400> SEQUENCE: 27

Ile Asn Gly Ser Ser Arg Tyr Ile
1               5

<210> SEQ ID NO 28
<211> LENGTH: 14
<212> TYPE: PRT
<213> ORGANISM: Artificial Sequence
<220> FEATURE:
<223> OTHER INFORMATION: Synthetic H2 mAb H-CDR3

<400> SEQUENCE: 28

Val Arg Ser Ser Asp Asp Tyr Phe Gly Gly Gly Met Asp Val
1               5                   10

<210> SEQ ID NO 29
<211> LENGTH: 111
<212> TYPE: PRT
<213> ORGANISM: Artificial Sequence
<220> FEATURE:
<223> OTHER INFORMATION: Synthetic H2 mAb VL

<400> SEQUENCE: 29

Gln Ser Val Leu Thr Gln Pro Ala Ser Val Ser Gly Ser Pro Gly Gln
1               5                   10                  15

Ser Ile Thr Ile Ser Cys Ala Gly Thr Ser Ser Asp Val Gly Gly Tyr
            20                  25                  30

Tyr Ser Val Ser Trp Tyr Gln Gln His Pro Gly Lys Ala Pro Lys Leu
        35                  40                  45

Met Ile Tyr Asn Asp Ser Tyr Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Ser Thr Tyr Tyr
                85                  90                  95

Ser Thr Arg Val Phe Gly Gly Gly Thr Lys Leu Ala Val Leu Gly
            100                 105                 110

<210> SEQ ID NO 30
<211> LENGTH: 9
<212> TYPE: PRT
<213> ORGANISM: Artificial Sequence
<220> FEATURE:
<223> OTHER INFORMATION: Synthetic H2 mAb L-CDR1

<400> SEQUENCE: 30

Ser Ser Asp Val Gly Gly Tyr Tyr Ser
1               5

<210> SEQ ID NO 31
<211> LENGTH: 3
<212> TYPE: PRT
<213> ORGANISM: Artificial Sequence
<220> FEATURE:
<223> OTHER INFORMATION: Synthetic H2 mAb L-CDR2

<400> SEQUENCE: 31

Asn Asp Ser
1

<210> SEQ ID NO 32
<211> LENGTH: 9
<212> TYPE: PRT
```

<213> ORGANISM: Artificial Sequence
<220> FEATURE:
<223> OTHER INFORMATION: Synthetic H2 mAb L-CDR3

<400> SEQUENCE: 32

Ser Ser Thr Tyr Tyr Ser Thr Arg Val
1               5

<210> SEQ ID NO 33
<211> LENGTH: 1308
<212> TYPE: PRT
<213> ORGANISM: Homo sapiens

<400> SEQUENCE: 33

Met Lys Pro Ala Thr Gly Leu Trp Val Trp Val Ser Leu Leu Val Ala
1               5                   10                  15

Ala Gly Thr Val Gln Pro Ser Asp Ser Gln Ser Val Cys Ala Gly Thr
                20                  25                  30

Glu Asn Lys Leu Ser Ser Leu Ser Asp Leu Glu Gln Gln Tyr Arg Ala
            35                  40                  45

Leu Arg Lys Tyr Tyr Glu Asn Cys Glu Val Val Met Gly Asn Leu Glu
        50                  55                  60

Ile Thr Ser Ile Glu His Asn Arg Asp Leu Ser Phe Leu Arg Ser Val
65                  70                  75                  80

Arg Glu Val Thr Gly Tyr Val Leu Val Ala Leu Asn Gln Phe Arg Tyr
                85                  90                  95

Leu Pro Leu Glu Asn Leu Arg Ile Ile Arg Gly Thr Lys Leu Tyr Glu
                100                 105                 110

Asp Arg Tyr Ala Leu Ala Ile Phe Leu Asn Tyr Arg Lys Asp Gly Asn
            115                 120                 125

Phe Gly Leu Gln Glu Leu Gly Leu Lys Asn Leu Thr Glu Ile Leu Asn
        130                 135                 140

Gly Gly Val Tyr Val Asp Gln Asn Lys Phe Leu Cys Tyr Ala Asp Thr
145                 150                 155                 160

Ile His Trp Gln Asp Ile Val Arg Asn Pro Trp Pro Ser Asn Leu Thr
                165                 170                 175

Leu Val Ser Thr Asn Gly Ser Ser Gly Cys Gly Arg Cys His Lys Ser
                180                 185                 190

Cys Thr Gly Arg Cys Trp Gly Pro Thr Glu Asn His Cys Gln Thr Leu
                195                 200                 205

Thr Arg Thr Val Cys Ala Glu Gln Cys Asp Gly Arg Cys Tyr Gly Pro
        210                 215                 220

Tyr Val Ser Asp Cys Cys His Arg Glu Cys Ala Gly Gly Cys Ser Gly
225                 230                 235                 240

Pro Lys Asp Thr Asp Cys Phe Ala Cys Met Asn Phe Asn Asp Ser Gly
                245                 250                 255

Ala Cys Val Thr Gln Cys Pro Gln Thr Phe Val Tyr Asn Pro Thr Thr
                260                 265                 270

Phe Gln Leu Glu His Asn Phe Asn Ala Lys Tyr Thr Tyr Gly Ala Phe
            275                 280                 285

Cys Val Lys Lys Cys Pro His Asn Phe Val Val Asp Ser Ser Ser Cys
            290                 295                 300

Val Arg Ala Cys Pro Ser Ser Lys Met Glu Val Glu Glu Asn Gly Ile
305                 310                 315                 320

Lys Met Cys Lys Pro Cys Thr Asp Ile Cys Pro Lys Ala Cys Asp Gly
                325                 330                 335

-continued

```
Ile Gly Thr Gly Ser Leu Met Ser Ala Gln Thr Val Asp Ser Ser Asn
            340                 345                 350

Ile Asp Lys Phe Ile Asn Cys Thr Lys Ile Asn Gly Asn Leu Ile Phe
            355                 360                 365

Leu Val Thr Gly Ile His Gly Asp Pro Tyr Asn Ala Ile Glu Ala Ile
            370                 375                 380

Asp Pro Glu Lys Leu Asn Val Phe Arg Thr Val Arg Glu Ile Thr Gly
385                 390                 395                 400

Phe Leu Asn Ile Gln Ser Trp Pro Pro Asn Met Thr Asp Phe Ser Val
                    405                 410                 415

Phe Ser Asn Leu Val Thr Ile Gly Gly Arg Val Leu Tyr Ser Gly Leu
            420                 425                 430

Ser Leu Leu Ile Leu Lys Gln Gln Gly Ile Thr Ser Leu Gln Phe Gln
            435                 440                 445

Ser Leu Lys Glu Ile Ser Ala Gly Asn Ile Tyr Ile Thr Asp Asn Ser
    450                 455                 460

Asn Leu Cys Tyr Tyr His Thr Ile Asn Trp Thr Thr Leu Phe Ser Thr
465                 470                 475                 480

Ile Asn Gln Arg Ile Val Ile Arg Asp Asn Arg Lys Ala Glu Asn Cys
                    485                 490                 495

Thr Ala Glu Gly Met Val Cys Asn His Leu Cys Ser Ser Asp Gly Cys
            500                 505                 510

Trp Gly Pro Gly Pro Asp Gln Cys Leu Ser Cys Arg Arg Phe Ser Arg
            515                 520                 525

Gly Arg Ile Cys Ile Glu Ser Cys Asn Leu Tyr Asp Gly Glu Phe Arg
    530                 535                 540

Glu Phe Glu Asn Gly Ser Ile Cys Val Glu Cys Asp Pro Gln Cys Glu
545                 550                 555                 560

Lys Met Glu Asp Gly Leu Leu Thr Cys His Gly Pro Gly Pro Asp Asn
                    565                 570                 575

Cys Thr Lys Cys Ser His Phe Lys Asp Gly Pro Asn Cys Val Glu Lys
            580                 585                 590

Cys Pro Asp Gly Leu Gln Gly Ala Asn Ser Phe Ile Phe Lys Tyr Ala
            595                 600                 605

Asp Pro Asp Arg Glu Cys His Pro Cys His Pro Asn Cys Thr Gln Gly
    610                 615                 620

Cys Asn Gly Pro Thr Ser His Asp Cys Ile Tyr Tyr Pro Trp Thr Gly
625                 630                 635                 640

His Ser Thr Leu Pro Gln His Ala Arg Thr Pro Leu Ile Ala Ala Gly
                    645                 650                 655

Val Ile Gly Gly Leu Phe Ile Leu Val Ile Val Gly Leu Thr Phe Ala
            660                 665                 670

Val Tyr Val Arg Arg Lys Ser Ile Lys Lys Lys Arg Ala Leu Arg Arg
            675                 680                 685

Phe Leu Glu Thr Glu Leu Val Glu Pro Leu Thr Pro Ser Gly Thr Ala
    690                 695                 700

Pro Asn Gln Ala Gln Leu Arg Ile Leu Lys Glu Thr Glu Leu Lys Arg
705                 710                 715                 720

Val Lys Val Leu Gly Ser Gly Ala Phe Gly Thr Val Tyr Lys Gly Ile
                    725                 730                 735

Trp Val Pro Glu Gly Glu Thr Val Lys Ile Pro Val Ala Ile Lys Ile
            740                 745                 750
```

-continued

```
Leu Asn Glu Thr Thr Gly Pro Lys Ala Asn Val Glu Phe Met Asp Glu
        755                 760                 765

Ala Leu Ile Met Ala Ser Met Asp His Pro His Leu Val Arg Leu Leu
        770                 775                 780

Gly Val Cys Leu Ser Pro Thr Ile Gln Leu Val Thr Gln Leu Met Pro
785                 790                 795                 800

His Gly Cys Leu Leu Glu Tyr Val His Glu His Lys Asp Asn Ile Gly
                    805                 810                 815

Ser Gln Leu Leu Leu Asn Trp Cys Val Gln Ile Ala Lys Gly Met Met
                    820                 825                 830

Tyr Leu Glu Glu Arg Arg Leu Val His Arg Asp Leu Ala Ala Arg Asn
        835                 840                 845

Val Leu Val Lys Ser Pro Asn His Val Lys Ile Thr Asp Phe Gly Leu
        850                 855                 860

Ala Arg Leu Leu Glu Gly Asp Glu Lys Glu Tyr Asn Ala Asp Gly Gly
865                 870                 875                 880

Lys Met Pro Ile Lys Trp Met Ala Leu Glu Cys Ile His Tyr Arg Lys
                    885                 890                 895

Phe Thr His Gln Ser Asp Val Trp Ser Tyr Gly Val Thr Ile Trp Glu
                    900                 905                 910

Leu Met Thr Phe Gly Gly Lys Pro Tyr Asp Gly Ile Pro Thr Arg Glu
                    915                 920                 925

Ile Pro Asp Leu Leu Glu Lys Gly Glu Arg Leu Pro Gln Pro Pro Ile
        930                 935                 940

Cys Thr Ile Asp Val Tyr Met Val Met Val Lys Cys Trp Met Ile Asp
945                 950                 955                 960

Ala Asp Ser Arg Pro Lys Phe Lys Glu Leu Ala Ala Glu Phe Ser Arg
                    965                 970                 975

Met Ala Arg Asp Pro Gln Arg Tyr Leu Val Ile Gln Gly Asp Asp Arg
                    980                 985                 990

Met Lys Leu Pro Ser Pro Asn Asp  Ser Lys Phe Phe Gln  Asn Leu Leu
            995                 1000                1005

Asp Glu  Glu Asp Leu Glu Asp  Met Met Asp Ala Glu  Glu Tyr Leu
    1010                1015                1020

Val Pro  Gln Ala Phe Asn Ile  Pro Pro Pro Ile Tyr  Thr Ser Arg
    1025                1030                1035

Ala Arg  Ile Asp Ser Asn Arg  Ser Glu Ile Gly His  Ser Pro Pro
    1040                1045                1050

Pro Ala  Tyr Thr Pro Met Ser  Gly Asn Gln Phe Val  Tyr Arg Asp
    1055                1060                1065

Gly Gly  Phe Ala Ala Glu Gln  Gly Val Ser Val Pro  Tyr Arg Ala
    1070                1075                1080

Pro Thr  Ser Thr Ile Pro Glu  Ala Pro Val Ala Gln  Gly Ala Thr
    1085                1090                1095

Ala Glu  Ile Phe Asp Asp Ser  Cys Cys Asn Gly Thr  Leu Arg Lys
    1100                1105                1110

Pro Val  Ala Pro His Val Gln  Glu Asp Ser Ser Thr  Gln Arg Tyr
    1115                1120                1125

Ser Ala  Asp Pro Thr Val Phe  Ala Pro Glu Arg Ser  Pro Arg Gly
    1130                1135                1140

Glu Leu  Asp Glu Glu Gly Tyr  Met Thr Pro Met Arg  Asp Lys Pro
    1145                1150                1155

Lys Gln  Glu Tyr Leu Asn Pro  Val Glu Glu Asn Pro  Phe Val Ser
```

-continued

```
        1160                1165                1170

Arg Arg  Lys Asn Gly Asp Leu  Gln Ala Leu Asp Asn  Pro Glu Tyr
    1175                1180                1185

His Asn  Ala Ser Asn Gly Pro  Pro Lys Ala Glu Asp  Glu Tyr Val
    1190                1195                1200

Asn Glu  Pro Leu Tyr Leu Asn  Thr Phe Ala Asn Thr  Leu Gly Lys
    1205                1210                1215

Ala Glu  Tyr Leu Lys Asn Asn  Ile Leu Ser Met Pro  Glu Lys Ala
    1220                1225                1230

Lys Lys  Ala Phe Asp Asn Pro  Asp Tyr Trp Asn His  Ser Leu Pro
    1235                1240                1245

Pro Arg  Ser Thr Leu Gln His  Pro Asp Tyr Leu Gln  Glu Tyr Ser
    1250                1255                1260

Thr Lys  Tyr Phe Tyr Lys Gln  Asn Gly Arg Ile Arg  Pro Ile Val
    1265                1270                1275

Ala Glu  Asn Pro Glu Tyr Leu  Ser Glu Phe Ser Leu  Lys Pro Gly
    1280                1285                1290

Thr Val  Leu Pro Pro Pro Pro  Tyr Arg His Arg Asn  Thr Val Val
    1295                1300                1305
```

ANTIBODIES HAVING SPECIFICITY TO HER4 AND USES THEREOF

FIELD OF THE INVENTION

The present invention relates to antibodies having specificity to HER4 and uses thereof, which are able to induce biased 4ICD routing/signaling.

BACKGROUND OF THE INVENTION

Human epidermal growth factor receptor 4 (HER4) is a tyrosine kinase receptor belonging to the EGFR family. HER 4 is involved in the phenomena of resistance to treatments (Canfield et al, 2015 Cell Cycle 14(4):648-55) and plays a role of oncogenic driver in certain cancers (Prickett et al, 2009 Nat Genet. 41(10):1127-32). mRNA of HER4 undergoes alternative splicing which leads to membrane addressing of four isoforms that differ in extracellular (JMa or JMb (Elenius et al, 1997 J Biol Chem. 17; 272(42):26761-8)) and cytoplasmic (CYT1 or CYT2: (Elenius et al, 1999 Oncogene 22; 18(16):2607-15)) parts. These four produced receptors are called JMaCYT1, JMaCYT2, JMbCYT1 and JMbCYT2. The JMa isoforms (unlike JMb) have a juxtamembrane cleavage site by the enzyme TACE. Cleavage occurring mainly during ligand-dependent activation of the receptor, its natural ligand being neuregulin (NRG). This first cleavage allows a second intracellularly by the γ-secretase enzyme, releasing the intracellular portion of the so-called 4ICD receptor, mainly dictating HER4 signaling (Williams et al, 2004al, J Cell Biol. 167(3):469-78). The JMaCYT1 or JMbCYT1 isoforms can in particular activate the PI3K/AKT pathway and induce the degradation of the receptor, unlike JMaCYT2 or JMbCYT2. Although it induces cell proliferation (Kainulainen et al, 2000 al, J Biol Chem. 275(12):8641-9), NRG has also been described as having a pro-apoptotic action via HER4 (Das et al, 2010 Oncogene. 29(37):5214-9). The JMa isoforms appear to be predominantly expressed on the surface of tumor cells, with homogeneous expression of CYT1/CYT2 (Veikkolainen et al, 2011 Cell Cycle. 10(16):2647-57).

The inventors hypothesized that HER4 targeting would be relevant only in the case where JMa isoforms are only affected, so as to bias 4ICD signaling. Effective anti-HER4 antibodies should be receptor agonists, to potentiate this tumor suppressor effect, directing 4ICD to mitochondria to induce apoptosis (Naresh et al, 2006 Cancer Res. 66(12): 6412-20), whereas classical 4ICD signaling to the nucleus promotes proliferation (Kainulainen et al, 2000 J Biol Chem. 275(12):8641-9).

The inventors have selected, by phage display on cells, HER4 agonist antibodies (P. Martineau Coll., IRCM). No therapeutic anti-HER4 antibody having this biological profile has been described to date. Accordingly, the overall objectives are thus to develop antibodies against HER4 receptor in order to propose a new targeted therapy against cancer.

SUMMARY OF THE INVENTION

The present invention relates to antibodies (particularly monoclonal antibodies) having specificity to HER4 and uses thereof. In particular, the present invention is defined by the claims.

The inventors have isolated by antibody phage display three fully human anti-HER4 single-chain variable antibody fragment (scFv), selected on human HER4 extracellular domain, referred as C6 mAb, D5 mAb and F4 mAb and one fully human anti-HER4 scFv named H2 mAb, selected on NRG1β1-stimulated EGFR/HER4 JMaCYT1-transfected NIH3T3 cells. The inventors have also worked on HER4 epitope mapping.

DETAILED DESCRIPTION OF THE INVENTION

The inventors have realized a HER4 epitope mapping using the MAbTope technology (Bourquard et al. 2015) developed by the MAbSilico company (Nouzilly, France). The inventors have identified the amino acids of the region P1: (amino acids 606-623), region P2 (amino acids 573-593) to belong to the D5 and C6 putative epitopes. More particularly, the domains identified are restricted to regions 605-620 (part of P1 area) and 575-592 (part of P2 area). In these restricted regions, the inventors have identified the amino acid residues D611, E613 and H615 involved in these binding.

In one embodiment, the present invention relates to an isolated anti-HER4 antibody, wherein said antibody binds to HER4 protein. The sequence of said protein can be found under the Uniprot accession number Q15303. An exemplary amino acid sequence is represented by SEQ ID NO: 33.

```
                                        SEQ ID NO: 33
MKPATGLWVWVSLLVAAGTVQPSDSQSVCAGTENKLSSLSDLEQQYRALR

KYYENCEVVMGNLEITSIEHNRDLSFLRSVREVTGYVLVALNQFRYLPLE

NLRIIRGTKLYEDRYALAIFLNYRKDGNFGLQELGLKNLTEILNGGVYVD

QNKFLCYADTIHWQDIVRNPWPSNLTLVSTNGSSGCGRCHKSCTGRCWGP

TENHCQTLTRTVCAEQCDGRCYGPYVSDCCHRECAGGCSGPKDTDCFACM

NFNDSGACVTQCPQTFVYNPTTFQLEHNFNAKYTYGAFCVKKCPHNFVVD

SSSCVRACPSSKMEVEENGIKMCKPCTDICPKACDGIGTGSLMSAQTVDS

SNIDKFINCTKINGNLIFLVTGIHGDPYNAIEAIDPEKLNVFRTVREITG

FLNIQSWPPNMTDFSVFSNLVTIGGRVLYSGLSLLILKQQGITSLQFQSL

KEISAGNIYITDNSNLCYYHTINWTTLFSTINQRIVIRDNRKAENCTAEG

MVCNHLCSSDGCWGPGPDQCLSCRRFSRGRICIESCNLYDGEFREFENGS

ICVECDPQCEKMEDGLLTCHGPGPDNCTKCSHFKDGPNCVEKCPDGLQGA

NSFIFKYADPDRECHPCHPNCTQGCNGPTSHDCIYYPWTGHSTLPQHART

PLIAAGVIGGLFILVIVGLTFAVYVRRKSIKKKRALRRFLETELVEPLTP

SGTAPNQAQLRILKETELKRVKVLGSGAFGTVYKGIWVPEGETVKIPVAI

KILNETTGPKANVEFMDEALIMASMDHPHLVRLLGVCLSPTIQLVTQLMP

HGCLLEYVHEHKDNIGSQLLLNWCVQIAKGMMYLEERRLVHRDLAARNVL

VKSPNHVKITDFGLARLLEGDEKEYNADGGKMPIKWMALECIHYRKFTHQ

SDVWSYGVTIWELMTFGGKPYDGIPTREIPDLLEKGERLPQPPICTIDVY

MVMVKCWMIDADSRPKFKELAAEFSRMARDPQRYLVIQGDDRMKLPSPND

SKFFQNLLDEEDLEDMMDAEEYLVPQAFNIPPPIYTSRARIDSNRSEIGH

SPPPAYTPMSGNQFVYRDGGFAAEQGVSVPYRAPTSTIPEAPVAQGATAE

IFDDSCCNGTLRKPVAPHVQEDSSTQRYSADPTVFAPERSPRGELDEEGY

MTPMRDKPKQEYLNPVEENPFVSRRKNGDLQALDNPEYHNASNGPPKAED
```

3

-continued

EYVNEPLYLNTFANTLGKAEYLKNNILSMPEKAKKAFDNPDYWNHSLPPR

STLQHPDYLQEYSTKYFYKQNGRIRPIVAENPEYLSEFSLKPGTVLPPPP

YRHRNTVV

In some embodiment, the present invention relates to an isolated anti-HER4 antibody, wherein said antibody binds to JMa isoforms.

In some embodiment, the present invention relates to an isolated anti-HER4 antibody, wherein said antibody binds to JMaCYT1 isoform. The sequence of said protein can be found under the Uniprot accession number (*Homo sapiens*): NP_005226.

In some embodiment, the present invention relates to an isolated anti-HER4 antibody, wherein said antibody binds to JMaCYT2 isoform. The sequence of said protein can be found under the Uniprot accession number (*Homo sapiens*): NP_001036064.

In one embodiment, the present invention also provides for an isolated anti-HER4 antibody, wherein said antibody binds to an epitope of the HER4 protein comprising amino acid at position 613 of SEQ ID NO: 33 (residue E613), amino acid at position 611 of SEQ ID NO: 33 (residue D611) and/or amino acid at position 615 of SEQ ID NO: 33 (residue H615).

In one embodiment, the present invention also provides for an isolated anti-HER4 antibody, wherein said antibody binds to an epitope of the HER4 protein consisting of amino acid at position 613 of SEQ ID NO: 33 (residue E613), amino acid at position 611 of SEQ ID NO: 33 (residue D611) and/or amino acid at position 615 of SEQ ID NO: 33 (residue H615).

In one embodiment, the present invention provides for an isolated anti-HER4 antibody, wherein said antibody binds to an epitope of the HER4 protein comprising region P1 at position 606-623 of SEQ ID NO: 33 and/or region P2 at position 573-593 of SEQ ID NO: 33.

In one embodiment, the present invention provides for an isolated anti-HER4 antibody, wherein said antibody binds to an epitope of the HER4 protein consisting of region Plat position 606-623 of SEQ ID NO: 33 and/or region P2 at position 573-593 of SEQ ID NO: 33.

In one embodiment, the present invention provides for an isolated anti-HER4 antibody, wherein said antibody binds to an epitope of the HER4 protein comprising part of P1 area at position 605-620 of SEQ ID NO: 33 and/or part of P2 area at position 575-592 of SEQ ID NO: 33.

In one embodiment, the present invention provides for an isolated anti-HER4 antibody, wherein said antibody binds to an epitope of the HER4 protein consisting of part of P1 area at position 605-620 of SEQ ID NO: 33 and/or part of P2 area at position 575-592 of SEQ ID NO: 33.

In one embodiment, the present invention also relates to antibodies C6 mAb, D5 mAb, F4 mAb and H2 mAb having specificity to anti-HER4 wherein:

C6 mab, has:

(a) a heavy chain wherein the variable domain comprises:
  a H-CDR1 having a sequence set forth as SEQ ID NO: 2;
  a H-CDR2 having a sequence set forth as SEQ ID NO: 3;
  a H-CDR3 having a sequence set forth as SEQ ID NO: 4;

(b) a light chain wherein the variable domain comprises:
  a L-CDR1 having a sequence set forth as SEQ ID NO: 6;
  a L-CDR2 having a sequence set forth as SEQ ID NO: 7;
  a L-CDR3 having a sequence set forth as SEQ ID NO: 8;

D5 mab, has:

(a) a heavy chain wherein the variable domain comprises:
  a H-CDR1 having a sequence set forth as SEQ ID NO: 10;
  a H-CDR2 having a sequence set forth as SEQ ID NO: 11;
  a H-CDR3 having a sequence set forth as SEQ ID NO: 12;

(b) a light chain wherein the variable domain comprises:
  a L-CDR1 having a sequence set forth as SEQ ID NO: 14;
  a L-CDR2 having a sequence set forth as SEQ ID NO: 15;
  a L-CDR3 having a sequence set forth as SEQ ID NO: 16;

F4 mab, has:

(a) a heavy chain wherein the variable domain comprises:
  a H-CDR1 having a sequence set forth as SEQ ID NO: 18;
  a H-CDR2 having a sequence set forth as SEQ ID NO: 19;
  a H-CDR3 having a sequence set forth as SEQ ID NO: 20;

(b) a light chain wherein the variable domain comprises:
  a L-CDR1 having a sequence set forth as SEQ ID NO: 22;
  a L-CDR2 having a sequence set forth as SEQ ID NO: 23;
  a L-CDR3 having a sequence set forth as SEQ ID NO: 24;

H2 mab, has:

(a) a heavy chain wherein the variable domain comprises:
  a H-CDR1 having a sequence set forth as SEQ ID NO: 26;
  a H-CDR2 having a sequence set forth as SEQ ID NO: 27;
  a H-CDR3 having a sequence set forth as SEQ ID NO: 28;

(b) a light chain wherein the variable domain comprises:
  a L-CDR1 having a sequence set forth as SEQ ID NO: 30;
  a L-CDR2 having a sequence set forth as SEQ ID NO: 31;
  a L-CDR3 having a sequence set forth as SEQ ID NO: 32;

The inventors selected these antibodies for their intrinsic anti-metastatic properties. They showed that the antibodies C6 mAb and H2 mAb having specificity to anti-HER4 can promote the cleavage of the 4ICD of JMaCYT1, but not of JMaCYT2. 4ICD is then involved in the tumor suppressor pathways and in the apoptosis of cancer cells. In contrast antibodies D5 mAb and F4 mAb did not promote 4ICD cleavage.

As used herein, the term "HER" or "ErbB" relates to a family of four structurally related receptor tyrosine kinases (RTK). In human, the family includes Her1 (also known as EGFR, ErbB1), Her2 (also known as Neu, ErbB2), Her3 (also known as ErbB3), and Her4 (also known as ErbB4). The four HER receptors are transmembrane receptors composed of extracellular region or ectodomain or ligand binding region, a single transmembrane-spanning region and an intracellular cytoplasmic tyrosine kinase domain. They share an overall structure of two cysteine rich regions in their extracellular region, and a kinase domain flanked by a carboxy-terminal tail with tyrosine auto-phosphorylation sites.

As used herein, the term "HER4" has its general meaning in the art and includes human HER4, in particular the native-sequence polypeptide, isoforms, chimeric polypeptides, all homologs, fragments, and precursors of human HER4. HER4 binds to and is activated by neuregulins-2 and -3, heparin-binding EGF-like growth factor and betacellulin. HER4 has the UniProtKB accession number: Q15303. mRNA of HER4 undergoes alternative splicing which leads to membrane addressing of four isoforms called JMaCYT1, JMaCYT2, JMbCYT1 and JMbCYT2, which differ in their both ExtraCellular Domain (ECD, including JMa or JMb) and IntraCellular Domain (ICD, including CYT1 or CYT2). The sequence of HER4 can be found under the Uniprot accession number Q15303.

As used herein the term "antibody" or "immunoglobulin" have the same meaning, and will be used equally in the present invention. The term "antibody" as used herein refers to immunoglobulin molecules and immunologically active portions of immunoglobulin molecules, i.e., molecules that contain an antigen binding site that immunospecifically binds an antigen. As such, the term antibody encompasses not only whole antibody molecules, but also antibody fragments as well as variants (including derivatives) of antibodies and antibody fragments. In natural antibodies, two heavy chains are linked to each other by disulfide bonds and each heavy chain is linked to a light chain by a disulfide bond. There are two types of light chain, lambda (l) and kappa (k). There are five main heavy chain classes (or isotypes) which determine the functional activity of an antibody molecule: IgM, IgD, IgG, IgA and IgE. Each chain contains distinct sequence domains. The light chain includes two domains, a variable domain (VL) and a constant domain (CL). The heavy chain includes four domains, a variable domain (VH) and three constant domains (CHI, CH2 and CH3, collectively referred to as CH). The variable regions of both light (VL) and heavy (VH) chains determine binding recognition and specificity to the antigen. The constant region domains of the light (CL) and heavy (CH) chains confer important biological properties such as antibody chain association, secretion, trans-placental mobility, complement binding, and binding to Fc receptors (FcR). The Fv fragment is the N-terminal part of the Fab fragment of an immunoglobulin and consists of the variable portions of one light chain and one heavy chain. The specificity of the antibody resides in the structural complementarity between the antibody combining site and the antigenic determinant. Antibody combining sites are made up of residues that are primarily from the hypervariable or complementarity determining regions (CDRs). Occasionally, residues from nonhypervariable or framework regions (FR) can participate to the antibody binding site or influence the overall domain structure and hence the combining site. Complementarity Determining Regions or CDRs refer to amino acid sequences which together define the binding affinity and specificity of the natural Fv region of a native immunoglobulin binding site. The light and heavy chains of an immunoglobulin each have three CDRs, designated L-CDR1, L-CDR2, L-CDR3 and H-CDR1, H-CDR2, H-CDR3, respectively. An antigen-binding site, therefore, typically includes six CDRs, comprising the CDR set from each of a heavy and a light chain V region. Framework Regions (FRs) refer to amino acid sequences interposed between CDRs. In one embodiment, the antibodies of the invention are monoclonal antibodies.

In the context of the invention, the amino acid residues of the antibodies of the invention are numbered according to the IMGT numbering system. The IMGT unique numbering has been defined to compare the variable domains whatever the antigen receptor, the chain type, or the species (Lefranc M.-P., "Unique database numbering system for immunogenetic analysis" Immunology Today, 18, 509 (1997); Lefranc M.-P., "The IMGT unique numbering for Immunoglobulins, T cell receptors and Ig-like domains" The Immunologist, 7, 132-136 (1999).; Lefranc, M.-P., Pommié, C., Ruiz, M., Giudicelli, V., Foulquier, E., Truong, L., Thouvenin-Contet, V. and Lefranc, G., "IMGT unique numbering for immuno-globulin and T cell receptor variable domains and Ig superfamily V-like domains" Dev. Comp. Immunol., 27, 55-77 (2003).). In the IMGT unique numbering, the conserved amino acids always have the same position, for instance cysteine 23, tryptophan 41, hydrophobic amino acid 89, cysteine 104, phenylalanine or tryptophan 118. The IMGT unique numbering provides a standardized delimitation of the framework regions (FR1-IMGT: positions 1 to 26, FR2-IMGT: 39 to 55, FR3-IMGT: 66 to 104 and FR4-IMGT: 118 to 128) and of the complementarity determining regions: CDR1-IMGT: 27 to 38, CDR2-IMGT: 56 to 65 and CDR3-IMGT: 105 to 117. If the CDR3-IMGT length is less than 13 amino acids, gaps are created from the top of the loop, in the following order 111, 112, 110, 113, 109, 114, etc. If the CDR3-IMGT length is more than 13 amino acids, additional positions are created between positions 111 and 112 at the top of the CDR3-IMGT loop in the following order 112.1, 111.1, 112.2, 111.2, 112.3, 111.3, etc.

As used herein, the term "specificity" refers to the ability of an antibody to detectably bind an epitope presented on an antigen, such as HER4, while having relatively little detectable reactivity with non-HER4 proteins or structures (such as other proteins presented on cancerous cell, or on other cell types). Specificity can be relatively determined by binding or competitive binding assays, using, e.g., Biacore instruments, as described elsewhere herein. Specificity can be exhibited by, e.g., an about 10:1, about 20:1, about 50:1, about 100:1, 10.000:1 or greater ratio of affinity/avidity in binding to the specific antigen versus nonspecific binding to other irrelevant molecules (in this case the specific antigen is HER4). The term "affinity", as used herein, means the strength of the binding of an antibody to an epitope. The affinity of an antibody is given by the dissociation constant Kd, defined as [Ab]×[Ag]/[Ab-Ag], where [Ab-Ag] is the molar concentration of the antibody-antigen complex, [Ab] is the molar concentration of the unbound antibody and [Ag] is the molar concentration of the unbound antigen. The affinity constant Ka is defined by 1/Kd. Preferred methods for determining the affinity of mAbs can be found in Harlow, et al., Antibodies: A Laboratory Manual, Cold Spring Harbor Laboratory Press, Cold Spring Harbor, N.Y., 1988), Coligan et al., eds., Current Protocols in Immunology, Greene Publishing Assoc. and Wiley Interscience, N.Y., (1992, 1993), and Muller, Meth. Enzymol. 92:589-601 (1983), which references are entirely incorporated herein by reference. One preferred and standard method well known in the art for determining the affinity of mAbs is the use of Biacore instruments.

The present invention provides for anti-HER4 antibodies, particularly in a purified form or in an isolated form.

In some embodiments, the antibodies of the present invention are antibodies having a heavy chain comprising i) the H-CDR1 of C6 mAb, D5 mAb, F4 mAb or H2 mAb, ii) the H-CDR2 of C6 mAb, D5 mAb, F4 mAb or H2 mAb and iii) the H-CDR3 of C6 mAb, D5 mAb, F4 mAb or H2 mAb.

In some embodiments, the antibodies of the present invention are antibodies having a light chain comprising i) the L-CDR1 of C6 mAb, D5 mAb, F4 mAb or H2 mAb, ii) the L-CDR2 of C6 mAb, D5 mAb, F4 mAb or H2 mAb and iii) the L-CDR3 of C6 mAb, D5 mAb, F4 mAb or H2 mAb.

In some embodiments, the antibodies of the present invention are antibodies having a heavy chain comprising i) the H-CDR1 of C6 mAb, D5 mAb, F4 mAb or H2 mAb, ii) the H-CDR2 of C6 mAb, D5 mAb, F4 mAb or H2 mAb and iii) the H-CDR3 of C6 mAb, D5 mAb, F4 mAb or H2 mAb and a light chain i) the L-CDR1 of C6 mAb, D5 mAb, F4 mAb or H2 mAb, ii) the L-CDR2 of C6 mAb, D5 mAb, F4 mAb or H2 mAb and iii) the L-CDR3 of C6 mAb, D5 mAb, F4 mAb or H2 mAb.

More particularly, the antibodies of the present invention are antibodies having a heavy chain having at least 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or 100% of identity with SEQ ID NO: 1, SEQ ID NO: 9, SEQ ID NO: 17 or SEQ ID NO: 25.

In some embodiments, the antibodies of the present invention are antibodies having a light chain having at least 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or 100% of identity with SEQ ID NO: 5, SEQ ID NO: 13, SEQ ID NO: 21 or SEQ ID NO: 29.

In some embodiments, the antibodies of the present invention are antibodies having a heavy chain having at least 70, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or 100% of identity with SEQ ID NO: 1, SEQ ID NO: 9, SEQ ID NO: 17 or SEQ ID NO: 25 and a light chain having at least 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or 100% of identity with SEQ ID NO: 5, SEQ ID NO: 13, SEQ ID NO: 21 or SEQ ID NO: 29.

In some embodiments, the antibodies of the present invention are antibodies having a heavy chain which is identical to SEQ ID NO: 1, SEQ ID NO: 9, SEQ ID NO: 17 or SEQ ID NO: 25.

In some embodiments, the antibodies of the present invention are antibodies having a light chain identical to SEQ ID NO: 5, SEQ ID NO: 13, SEQ ID NO: 21 or SEQ ID NO: 29.

In some embodiments, the antibodies of the present invention are antibodies having a heavy chain identical to SEQ ID NO:1, SEQ ID NO: 9, SEQ ID NO: 17 or SEQ ID NO: 25 and a light chain identical to SEQ ID NO: 5, SEQ ID NO: 13, SEQ ID NO: 21 or SEQ ID NO: 29.

In another embodiment, the antibodies of the present invention are antibodies comprising:

a heavy chain comprising i) a H-CDR1 having at least 90% of identity with SEQ ID NO: 2, SEQ ID NO: 10, SEQ ID NO: 18 or SEQ ID NO: 26, ii) a H-CDR2 having at least 90% of identity with SEQ ID NO: 3, SEQ ID NO: 11, SEQ ID NO: 19 or SEQ ID NO: 27 and iii) a H-CDR3 having at least 90% of identity with SEQ ID NO: 4, SEQ ID NO: 12, SEQ ID NO: 20 or SEQ ID NO: 28 and a light chain comprising i) a L-CDR1 having at least 90% of identity with SEQ ID NO: 6, SEQ ID NO: 14, SEQ ID NO: 22 or SEQ ID NO: 30, ii) a L-CDR2 having at least 90% of identity with SEQ ID NO: 7, SEQ ID NO: 15, SEQ ID NO: 23 or SEQ ID NO: 31 and iii) a L-CDR3 having at least 90% of identity with SEQ ID NO: 8, SEQ ID NO: 16, SEQ ID NO: 24 or SEQ ID NO: 32.

The sequences of interest in the present application are indicated in the following Table 1:

TABLE 1

| Sequences of C6 mAb, D5 mAb, F4 mAb and H2 mAb | | | |
|---|---|---|---|
| Antibodies | Domains | SEQ ID NO: | Sequences |
| C6 mAb | VH | SEQ ID NO: 1 | EVQLVESGGSLVKPGGSLRLSCAASG FTFSNYYMNWVRQAPGKGLEWISSIS GSSRYIDYADFVKGRFTISRDNATNS LYLQMNSLRAEDTAVYYCVRSSSDY FGGGMDVWGRGTLVTVSS |
| | H-CDR1 | SEQ ID NO: 2 | GFTFSNYY |
| | H-CDR2 | SEQ ID NO: 3 | ISGSSRYI |
| | H-CDR3 | SEQ ID NO: 4 | VRSSSDYFGGGMDV |
| | VL | SEQ ID NO: 5 | QSVLTQPASVSGSPGQSITISCAGTSS DVGGSYYVSWYQQHPGKAPKLMIY YDSYRPSGVSNRFSGSKSGNTASLTIS GLQAEDEADYYCSSSTYNSTRVFGG GTKLAVLG |
| | L-CDR1 | SEQ ID NO: 6 | SSDVGGSYY |
| | L-CDR2 | SEQ ID NO: 7 | YDS |
| | L-CDR3 | SEQ ID NO: 8 | SSSTYNSTRV |
| D5 mAb | VH | SEQ ID NO: 9 | EVQLVESGGSLVKPGGSLRLSCAASG FTFSNYYMNWVRQAPGKGLEWISSI DGSSRYIDYADFVKGRFTISRDNATN SLYLQMNSLRAEDTAVYYCVRSSSD YFGGGMDVWGRGTLVTVSS |
| | H-CDR1 | SEQ ID NO: 10 | GFTFSNYY |
| | H-CDR2 | SEQ ID NO: 11 | IDGSSRYI |
| | H-CDR3 | SEQ ID NO: 12 | VRSSSDYFGGGMDV |
| | VL | SEQ ID NO: 13 | QSVLTQPASVSGSPGQSITISCAGTSS DVGGSYVSWYQQHPGKAPKLMIYY DSYRPSGVSNRFSGSKSGNTASLTISG LQAEDEADYYCSSNTYYSTRVFGGG TKLAVLG |

TABLE 1-continued

| Antibodies | Domains | SEQ ID NO: | Sequences |
|---|---|---|---|
| | L-CDR1 | SEQ ID NO: 14 | SSDVGGSSY |
| | L-CDR2 | SEQ ID NO: 15 | YDS |
| | L-CDR3 | SEQ ID NO: 16 | SSNTYYSTRV |
| F4 mAb | VH | SEQ ID NO: 17 | EVQLVESGGSLVKPGGSLRLSCAASG<br>FTFSNNDMNWVRQAPGKGLEWISSIS<br>GSSRYINYADFVKGRFTISRDNATNS<br>LYLQMNSLRAEDTAVYYCVRSSDDY<br>FGGGMDVWGRGTLVTVSS |
| | H-CDR1 | SEQ ID NO: 18 | GFTFSNND |
| | H-CDR2 | SEQ ID NO: 19 | ISGSSRYI |
| | H-CDR3 | SEQ ID NO: 20 | VRSSDDYFGGGMDV |
| | VL | SEQ ID NO: 21 | QSVLTQPASVSGSPGQSITISCAGTSS<br>DVGGYSGVSWYQQHPGKAPKLMIY<br>NDSYRPSGVSNRFSGSKSGNTASLTIS<br>GLQAEDEADYYCSSYTNNSTRVFGG<br>GTKLAVLG |
| | L-CDR1 | SEQ ID NO: 22 | SSDVGGYSG |
| | L-CDR2 | SEQ ID NO: 23 | NDS |
| | L-CDR3 | SEQ ID NO: 24 | SSYTNNSTRV |
| H2 mAb | VH | SEQ ID NO: 25 | EVQLVESGGSLVKPGGSLRLSCAASG<br>FTFSNNDMNWVRQAPGKGLEWISDI<br>NGSSRYIYYADFVKGRFTISRDNATN<br>SLYLQMNSLRAEDTAVYYCVRSSDD<br>YFGGGMDVWGRGTLVTVSS |
| | H-CDR1 | SEQ ID NO: 26 | GFTFSNND |
| | H-CDR2 | SEQ ID NO: 27 | INGSSRYI |
| | H-CDR3 | SEQ ID NO: 28 | VRSSDDYFGGGMDV |
| | VL | SEQ ID NO: 29 | QSVLTQPASVSGSPGQSITISCAGTSS<br>DVGGYYSVSWYQQHPGKAPKLMIY<br>NDSYRPSGVSNRFSGSKSGNTASLTIS<br>GLQAEDEADYYCSSSTYYSTRVFGG<br>GTKLAVLG |
| | L-CDR1 | SEQ ID NO: 30 | SSDVGGYYS |
| | L-CDR2 | SEQ ID NO: 31 | NDS |
| | L-CDR3 | SEQ ID NO: 32 | SSTYYSTRV |

The terms "monoclonal antibody", "monoclonal Ab", "monoclonal antibody composition", "mAb", or the like, as used herein refer to a preparation of antibody molecules of single molecular composition. A monoclonal antibody composition displays a single binding specificity and affinity for a particular epitope.

As used herein, the term "epitope" refers to a specific arrangement of amino acids located on a protein or proteins to which an antibody binds. Epitopes often consist of a chemically active surface grouping of molecules such as amino acids or sugar side chains, and have specific three-dimensional structural characteristics as well as specific charge characteristics. Epitopes can be linear or conformational, i.e., involving two or more sequences of amino acids in various regions of the antigen that may not necessarily be contiguous.

The antibodies of the present invention are produced by any technique known in the art, such as, without limitation, any chemical, biological, genetic or enzymatic technique, either alone or in combination. Typically, knowing the amino acid sequence of the desired sequence, one skilled in the art can readily produce said antibodies, by standard techniques for production of polypeptides. For instance, they can be synthesized using well-known solid phase method, preferably using a commercially available peptide synthesis apparatus (such as that made by Applied Biosystems, Foster City, Calif.) and following the manufacturer's instructions. Alternatively, antibodies of the present invention can be synthesized by recombinant DNA techniques well-known in the art. For example, antibodies can be obtained as DNA expression products after incorporation of DNA sequences encoding the antibodies into expression vectors and introduction of such vectors into suitable eukaryotic or prokaryotic hosts that will express the desired antibodies, from which they can be later isolated using well-known techniques.

In one embodiment, the monoclonal antibodies of the invention is chimeric antibodies, particularly chimeric mouse/human antibodies.

According to the invention, the term "chimeric antibody" refers to an antibody which comprises a VH domain and a VL domain of a non-human antibody, and a CH domain and a CL domain of a human antibody.

In some embodiments, the human chimeric antibodies of the present invention can be produced by obtaining nucleic sequences encoding VL and VH domains as previously described, constructing a human chimeric antibody expression vector by inserting them into an expression vector for animal cell having genes encoding human antibody CH and human antibody CL, and expressing the coding sequence by introducing the expression vector into an animal cell. As the CH domain of a human chimeric antibody, it may be any region which belongs to human immunoglobulin, but those of IgG class are suitable and any one of subclasses belonging to IgG class, such as IgG1, IgG2, IgG3 and IgG4, can also be used. Also, as the CL of a human chimeric antibody, it may be any region which belongs to Ig, and those of kappa class or lambda class can be used. Methods for producing chimeric antibodies involve conventional recombinant DNA and gene transfection techniques are well known in the art (See Morrison S L. et al. (1984) and patent documents U.S. Pat. Nos. 5,202,238; and 5,204,244). In another embodiment, the monoclonal antibodies of the invention is humanized antibodies. In particular, in said humanized antibodies, the variable domain comprises human acceptor frameworks regions, and optionally human constant domain where present, and non-human donor CDRs, such as mouse CDRs.

In one embodiment, the humanized antibodies can be derived from chimeric antibodies (obtained from the antibodies of the invention).

In another embodiment, the monoclonal antibodies of the invention is a caninized or primatized based on the same methods of humanization.

According to the invention, the term "humanized antibodies" refers to antibodies having variable region framework and constant regions from human antibodies but retains the CDRs of previous non-human antibodies.

The humanized antibodies of the present invention may be produced by obtaining nucleic acid sequences encoding CDR domains, as previously described, constructing humanized antibodies expression vector by inserting them into an expression vector for animal cell having genes encoding (i) a heavy chain constant region identical to that of a human antibody and (ii) a light chain constant region identical to that of a human antibody, and expressing the genes by introducing the expression vector into an animal cell. The humanized antibody expression vector may be either of a type in which a gene encoding an antibody heavy chain and a gene encoding an antibody light chain exists on separate vectors or of a type in which both genes exist on the same vector (tandem type). In respect of easiness of construction of a humanized antibody expression vector, easiness of introduction into animal cells, and balance between the expression levels of antibody H and L chains in animal cells, humanized antibody expression vector of the tandem type is preferred. Examples of tandem type humanized antibody expression vector include pKANTEX93 (WO 97/10354), pEE18 and the like. Methods for producing humanized antibodies based on conventional recombinant DNA and gene transfection techniques are well known in the art (See, e. g., Riechmann L. et al. 1988; Neuberger M S. et al. 1985). Antibodies can be humanized using a variety of techniques known in the art including, for example, CDR-grafting (EP 239,400; PCT publication WO91/09967; U.S. Pat. Nos. 5,225,539; 5,530,101; and 5,585,089), veneering or resurfacing (EP 592,106; EP 519,596; Padlan E A (1991); Studnicka G M et al. (1994); Roguska M A. et al. (1994)), and chain shuffling (U.S. Pat. No. 5,565,332). The general recombinant DNA technology for preparation of such antibodies is also known (see European Patent Application EP 125023 and International Patent Application WO 96/02576).

In one embodiment, the antibodies of the invention are antigen biding fragment selected from the group consisting of a Fab, a F(ab)'2, a single domain antibody, a ScFv, a Sc(Fv)2, a diabody, a triabody, a tetrabody, an unibody, a minibody, a maxibody, a small modular immunopharmaceutical (SMIP), minimal recognition units consisting of the amino acid residues that mimic the hypervariable region of an antibody as an isolated complementary determining region (CDR), and fragments which comprise or consist of the VH or VL chains as well as amino acid sequence having at least 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or 100% of identity with SEQ ID NO: 1, SEQ ID NO: 9, SEQ ID NO: 17, or SEQ ID NO: 25 or SEQ ID NO: 5, SEQ ID NO: 13, SEQ ID NO: 21, SEQ ID NO: 29.

The term "antigen binding fragment" of an antibody, as used herein, refers to one or more fragments of an intact antibody that retain the ability to specifically binds to a given antigen (e.g., [HER4]). Antigen biding functions of an antibody can be performed by fragments of an intact antibody. Examples of biding fragments encompassed within the term antigen biding fragment of an antibody include a Fab fragment, a monovalent fragment consisting of the VL,VH,CL and CH1 domains; a Fab' fragment, a monovalent fragment consisting of the VL,VH,CL,CH1 domains and hinge region; a F(ab')2 fragment, a bivalent fragment comprising two Fab' fragments linked by a disulfide bridge at the hinge region; an Fd fragment consisting of VH domains of a single arm of an antibody; a single domain antibody (sdAb) fragment (Ward et al., 1989 Nature 341: 544-546), which consists of a VH domain or a VL domain; and an isolated complementary determining region (CDR). Furthermore, although the two domains of the Fv fragment, VL and VH, are coded for by separate genes, they can be joined, using recombinant methods, by an artificial peptide linker that enables them to be made as a single protein chain in which the VL and VH regions pair to form monovalent molecules (known as single chain Fv (ScFv); see, e.g., Bird et al., 1989 Science 242:423-426; and Huston et al., 1988 proc. Natl. Acad. Sci. 85:5879-5883). "dsFv" is a VH::VL heterodimer stabilised by a disulfide bond. Divalent and multivalent antibody fragments can form either spontaneously by association of monovalent scFvs, or can be generated by coupling monovalent scFvs by a peptide linker, such as divalent sc(Fv)2. Such single chain antibodies include one or more antigen biding portions or fragments of an antibody. These antibody fragments are obtained using conventional techniques known to those skilled in the art, and the fragments are screened for utility in the same manner as are intact antibodies. A unibody is another type of antibody fragment lacking the hinge region of IgG4 antibodies. The deletion of the hinge region results in a molecule that is essentially half the size of traditional IgG4 antibodies and has a univalent binding region rather than the bivalent biding region of IgG4 antibodies. Antigen binding fragments can be incorporated into single domain antibodies, SMIP, maxibodies, minibodies, intrabodies, diabodies, triabodies and tetrabodies (see, e.g., Hollinger and Hudson, 2005, Nature Biotechnology, 23, 9, 1126-1136). The term "diabodies" "tribodies" or "tetrabodies" refers to small antibody fragments with multivalent antigen-binding sites (2, 3 or four), which fragments comprise a heavy-chain variable domain (VH) connected to a light-chain variable domain (VL) in the same polypeptide chain (VH-VL). By using a linker that is too short to allow pairing between the two domains on the same chain, the domains are forced to pair with the complementary domains of another chain and create two antigen-binding sites. Antigen biding fragments can be incorporated into single chain molecules comprising a pair of tandem Fv segments (VH-CH1-VH-CH1) Which, together with complementary light chain polypeptides, form a pair of antigen binding regions (Zapata et al., 1995 Protein Eng. 8(10); 1057-1062 and U.S. Pat. No. 5,641,870).

The Fab of the present invention can be obtained by treating antibodies which specifically reacts with HER4 with a protease, papaine. Also, the Fab can be produced by inserting DNA encoding Fab of the antibody into a vector for prokaryotic expression system, or for eukaryotic expression system, and introducing the vector into a procaryote or eucaryote (as appropriate) to express the Fab.

The F(ab')2 of the present invention can be obtained treating antibodies which specifically reacts with HER4 with a protease, pepsin. Also, the F(ab')2 can be produced by binding Fab' described below via a thioether bond or a disulfide bond.

The Fab' of the present invention can be obtained treating F(ab')2 which specifically reacts with HER4 with a reducing agent, dithiothreitol. Also, the Fab' can be produced by inserting DNA encoding Fab' fragment of the antibody into an expression vector for prokaryote, or an expression vector for eukaryote, and introducing the vector into a prokaryote or eukaryote (as appropriate) to perform its expression.

The scFv of the present invention can be produced by obtaining cDNA encoding the VH and VL domains as previously described, constructing DNA encoding scFv, inserting the DNA into an expression vector for prokaryote, or an expression vector for eukaryote, and then introducing the expression vector into a prokaryote or eukaryote (as appropriate) to express the scFv. To generate a humanized scFv fragment, a well known technology called CDR grafting may be used, which involves selecting the complementary determining regions (CDRs) from a donor scFv fragment, and grafting them onto a human scFv fragment framework of known three dimensional structure (see, e. g., WO98/45322; WO 87/02671; U.S. Pat. Nos. 5,859,205; 5,585,089; 4,816,567; EP0173494).

Domain Antibodies (dAbs) are the smallest functional binding units of antibodies—molecular weight approximately 13 kDa—and correspond to the variable regions of either the heavy (VH) or light (VL) chains of antibodies. Further details on domain antibodies and methods of their production are found in U.S. Pat. Nos. 6,291,158; 6,582,915; 6,593,081; 6,172,197; and 6,696,245; US 2004/0110941; EP 1433846, 0368684 and 0616640; WO 2005/035572, 2004/101790, 2004/081026, 2004/058821, 2004/003019 and 2003/002609, each of which is herein incorporated by reference in its entirety.

UniBodies are another antibody fragment technology, based upon the removal of the hinge region of IgG4 antibodies. The deletion of the hinge region results in a molecule that is essentially half the size of a traditional IgG4 antibody and has a univalent binding region rather than a bivalent binding region. Furthermore, because UniBodies are about smaller, they may show better distribution over larger solid tumors with potentially advantageous efficacy. Further details on UniBodies may be obtained by reference to WO 2007/059782, which is incorporated by reference in its entirety.

Nucleic Acid Sequence, Vectors and Host Cells

Accordingly, a further object of the invention relates to a nucleic acid molecule encoding antibodies according to the invention. More particularly the nucleic acid molecule encodes a heavy chain or a light chain of an antibody of the present invention.

Typically, said nucleic acid is a DNA or RNA molecule, which may be included in any suitable vector, such as a plasmid, cosmid, episome, artificial chromosome, phage or a viral vector. As used herein, the terms "vector", "cloning vector" and "expression vector" mean the vehicle by which a DNA or RNA sequence (e.g. a foreign gene) can be introduced into a host cell, so as to transform the host and promote expression (e.g. transcription and translation) of the introduced sequence. So, a further aspect of the invention relates to a vector comprising a nucleic acid of the invention. Such vectors may comprise regulatory elements, such as a promoter, enhancer, terminator and the like, to cause or direct expression of said antibody upon administration to a subject. Examples of promoters and enhancers used in the expression vector for animal cell include early promoter and enhancer of SV40 (Mizukami T. et al. 1987), LTR promoter and enhancer of Moloney mouse leukemia virus (Kuwana Y et al. 1987), promoter (Mason J O et al. 1985) and enhancer (Gillies S D et al. 1983) of immunoglobulin H chain and the like. Any expression vector for animal cell can be used, so long as a gene encoding the human antibody C region can be inserted and expressed. Examples of suitable vectors include pAGE107 (Miyaji H et al. 1990), pAGE103 (Mizukami T et al. 1987), pHSG274 (Brady G et al. 1984), pKCR (O'Hare K et al. 1981), pSG1 beta d2-4-(Miyaji H et al. 1990) and the like. Other examples of plasmids include replicating plasmids comprising an origin of replication, or integrative plasmids, such as for instance pUC, pcDNA, pBR, and the like. Other examples of viral vector include adenoviral, retroviral, herpes virus and AAV vectors. Such recombinant viruses may be produced by techniques known in the art, such as by transfecting packaging cells or by transient transfection with helper plasmids or viruses. Typical examples of virus packaging cells include PA317 cells, PsiCRIP cells, GPenv+ cells, 293 cells, etc. Detailed protocols for producing such replication-defective recombinant viruses may be found for instance in WO 95/14785, WO 96/22378, U.S. Pat. Nos. 5,882,877, 6,013,516, 4,861,719, 5,278,056 and WO 94/19478.

A further aspect of the invention relates to a host cell which has been transfected, infected or transformed by a nucleic acid and/or a vector according to the invention.

The term "transformation" means the introduction of a "foreign" (i.e. extrinsic or extracellular) gene, DNA or RNA sequence to a host cell, so that the host cell will express the introduced gene or sequence to produce a desired substance, typically a protein or enzyme coded by the introduced gene or sequence. A host cell that receives and expresses introduced DNA or RNA has been "transformed".

The nucleic acids of the invention may be used to produce an antibody of the present invention in a suitable expression system. The term "expression system" means a host cell and compatible vector under suitable conditions, e.g. for the expression of a protein coded for by foreign DNA carried by the vector and introduced to the host cell. Common expression systems include E. coli host cells and plasmid vectors, insect host cells and Baculovirus vectors, and mammalian host cells and vectors. Other examples of host cells include, without limitation, prokaryotic cells (such as bacteria) and eukaryotic cells (such as yeast cells, mammalian cells, insect cells, plant cells, etc.). Specific examples include E. coli, Kluyveromyces or Saccharomyces yeasts, mammalian cell lines (e.g., Vero cells, CHO cells, 3T3 cells, COS cells, etc.) as well as primary or established mammalian cell cultures (e.g., produced from lymphoblasts, fibroblasts, embryonic cells, epithelial cells, nervous cells, adipocytes, etc.). Examples also include mouse 5P2/0-Ag14 cell (ATCC CRL1581), mouse P3X63-Ag8.653 cell (ATCC CRL1580), CHO cell in which a dihydrofolate reductase gene (hereinafter referred to as "DHFR gene") is defective (Urlaub G et al; 1980), rat YB2/3HL.P2.G11.16Ag.20 cell (ATCC CRL1662, hereinafter referred to as "YB2/0 cell"), and the like. The present invention also relates to a method of producing a recombinant host cell expressing an antibody according to the invention, said method comprising the steps of: (i) introducing in vitro or ex vivo a recombinant nucleic acid or a vector as described above into a competent host cell, (ii) culturing in vitro or ex vivo the recombinant host cell obtained and (iii), optionally, selecting the cells which express and/or secrete said antibody. Such recombinant host cells can be used for the production of antibodies of the present invention.

Antibodies of the present invention are suitably separated from the culture medium by conventional immunoglobulin purification procedures such as, for example, protein A-Sepharose, hydroxylapatite chromatography, gel electrophoresis, dialysis, or affinity chromatography.

Functional Variants

The present invention thus provides antibodies comprising functional variants of the VL region, VH region, or one or more CDRs of C6 mab, D5 mab, F4 mab or H2 mab. A functional variant of a VL, VH, or CDR used in the context of a monoclonal antibody of the present invention still allows the antibody to retain at least a substantial proportion (at least about 50%, 60%, 70%, 80%, 90%, 95% or more) of the affinity/avidity and/or the specificity/selectivity of the parents antibodies (i.e. C6 mab, D5 mab, F4 mab or H2 mab antibodies) and in some cases such monoclonal antibodies of the present invention may be associated with greater affinity, selectivity and/or specificity than the parent Ab. Such variants can be obtained by a number of affinity maturation protocols including mutating the CDRs (Yang et al., J. Mol. Biol., 254, 392-403, 1995), chain shuffling (Marks et al., Bio/Technology, 10, 779-783, 1992), use of mutator strains of E. coli (Low et al., J. Mol. Biol., 250, 359-368, 1996), DNA shuffling (Patten et al., Curr. Opin. Biotechnol., 8, 724-733, 1997), phage display (Thompson et al., J. Mol. Biol., 256, 77-88, 1996) and sexual PCR (Crameri et al., Nature, 391, 288-291, 1998). Vaughan et al. (supra) discusses these methods of affinity maturation. Such functional variants typically retain significant sequence identity to the parent Ab. The sequence of CDR variants may differ from the sequence of the CDR of the parents antibodies sequences through mostly conservative substitutions; for instance at least about 35%, about 50% or more, about 60% or more, about 70% or more, about 75% or more, about 80% or more, about 85% or more, about 90% or more, (e.g., about 65-95%, such as about 92%, 93% or 94%) of the substitutions in the variant are conservative amino acid residue replacements. The sequences of CDR variants may differ from the sequence of the CDRs of the parents antibodies sequences through mostly conservative substitutions; for instance at least 10, such as at least 9, 8, 7, 6, 5, 4, 3, 2 or 1 of the substitutions in the variant are conservative amino acid residue replacements. In the context of the present invention, conservative substitutions may be defined by substitutions within the classes of amino acids reflected as follows:

Aliphatic residues I, L, V, and M

Cycloalkenyl-associated residues F, H, W, and Y

Hydrophobic residues A, C, F, G, H, I, L, M, R, T, V, W, and Y

Negatively charged residues D and E

Polar residues C, D, E, H, K, N, Q, R, S, and T

Positively charged residues H, K, and R

Small residues A, C, D, G, N, P, S, T, and V

Very small residues A, G, and S

Residues involved in turn A, C, D, E, G, H, K, N, Q, R, S, P, and formation T

Flexible residues Q, T, K, S, G, P, D, E, and R

More conservative substitutions groupings include: valine-leucine-isoleucine, phenylalanine-tyrosine, lysine-arginine, alanine-valine, and asparagine-glutamine. Conservation in terms of hydropathic/hydrophilic properties and residue weight/size also is substantially retained in a variant CDR as compared to a CDR of C6 mab, D5 mab, F4 mab or H2 mab antibodies. The importance of the hydropathic amino acid index in conferring interactive biologic function on a protein is generally understood in the art. It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like. Each amino acid has been assigned a hydropathic index on the basis of their hydrophobicity and charge characteristics these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophane (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5). The retention of similar residues may also or alternatively be measured by a similarity score, as determined by use of a BLAST program (e.g., BLAST 2.2.8 available through the NCBI using standard settings BLOSUM62, Open Gap=11 and Extended Gap=1). Suitable variants typically exhibit at least about 70% of identity to the parent peptide. According to the present invention a first amino acid sequence having at least 70% of identity with a second amino acid sequence means that the first sequence has 70; 71; 72; 73; 74; 75; 76; 77; 78; 79; 80; 81; 82; 83; 84; 85; 86; 87; 88; 89; 90; 91; 92; 93; 94; 95; 96; 97; 98; 99; or 100% of identity with the second amino acid sequence. According to the present invention a first amino acid sequence having at least 90% of identity with a second amino acid sequence means that the first sequence has 90; 91; 92; 93; 94; 95; 96; 97; 98; 99; or 100% of identity with the second amino acid sequence.

Antibody which Compete with the Antibody of the Invention

In another aspect, the invention provides an antibody that competes for binding to HER4 with the antibodies of the invention.

As used herein, the term "binding" in the context of the binding of an antibody to a predetermined antigen or epitope typically is a binding with an affinity corresponding to a $K_D$ of about $10^{-7}$ M or less, such as about $10^{-8}$ M or less, such as about $10^{-9}$ M or less, about $10^{-10}$ M or less, or about $10^{-11}$ M or even less when determined by for instance surface plasmon resonance (SPR) technology in a BIAcore 3000 instrument using a soluble form of the antigen as the ligand and the antibody as the analyte. BIACORE® (GE Healthcare, Piscaataway, N.J.) is one of a variety of surface plasmon resonance assay formats that are routinely used to epitope bin panels of monoclonal antibodies. Typically, an antibody binds to the predetermined antigen with an affinity corresponding to a $K_D$ that is at least ten-fold lower, such as at least 100-fold lower, for instance at least 1,000-fold lower, such as at least 10,000-fold lower, for instance at least 100,000-fold lower than its $K_D$ for binding to a non-specific antigen (e.g., BSA, casein), which is not identical or closely related to the predetermined antigen. When the $K_D$ of the antibody is very low (that is, the antibody has a high affinity), then the $K_D$ with which it binds the antigen is typically at least 10,000-fold lower than its $K_D$ for a non-specific antigen. An antibody is said to essentially not bind an antigen or epitope if such binding is either not detectable (using, for example, plasmon resonance (SPR) technology in a BIAcore 3000 instrument using a soluble form of the antigen as the ligand and the antibody as the analyte), or is 100 fold, 500 fold, 1000 fold or more than 1000 fold less than the binding detected by that antibody and an antigen or epitope having a different chemical structure or amino acid sequence.

Additional antibodies can be identified based on their ability to cross-compete (e.g., to competitively inhibit the binding of, in a statistically significant manner) with other antibodies of the invention in standard HER4 binding assays. The ability of a test antibody to inhibit the binding of antibodies of the present invention to HER4 demonstrates that the test antibody can compete with that antibody for binding to HER4; such an antibody may, according to non-limiting theory, bind to the same or a related (e.g., a structurally similar or spatially proximal) epitope on HER4 as the antibody with which it competes. Thus, another aspect of the invention provides antibodies that bind to the same antigen as, and compete with, the antibodies disclosed herein. As used herein, an antibody "competes" for binding when the competing antibody inhibits HER4 binding of an antibody or antigen binding fragment of the invention by more than 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98 or 99% in the presence of an equimolar concentration of competing antibody.

In other embodiments the antibodies or antigen binding fragments of the invention bind to one or more epitopes of HER4. In some embodiments, the epitopes to which the present antibodies or antigen binding fragments bind are linear epitopes. In other embodiments, the epitopes to which the present antibodies or antigen binding fragments bind are non-linear, conformational epitopes.

Accordingly, a further object of the invention relates to an antibody according to the invention which binds to HER4 protein.

Accordingly, a further object of the invention relates to an antibody according to the invention which binds to JMa-CYT1 isoform.

In one embodiment, the present invention relates to an antibody which binds to an epitope comprising region P1 at position 606-623 of SEQ ID NO: 33 and/or region P2 at position 573-593 of SEQ ID NO: 33.

In one embodiment the present invention relates to an antibody which binds to an epitope comprising part of P1 area at position 605-620 of SEQ ID NO: 33 and/or part of P2 area at position 575-592 of SEQ ID NO: 33.

In one embodiment, the present invention relates to an antibody which binds to an epitope comprising amino acid at position 613 of SEQ ID NO: 33 (residue E613), amino acid at position 611 of SEQ ID NO: 33 (residue D611) and/or amino acid at position 615 of SEQ ID NO: 33 (residue H615).

In one embodiment, the present invention relates to the antibody of invention which binds to an epitope comprising region P1 at position 606-623 of SEQ ID NO: 33 and/or region P2 at position 573-593 of SEQ ID NO: 33.

In one embodiment, the present invention relates to the antibody of invention which binds to an epitope comprising part of P1 area at position 605-620 of SEQ ID NO: 33 and/or part of P2 area at position 575-592 of SEQ ID NO: 33.

In one embodiment, the present invention relates to the antibody of invention which binds to an epitope comprising amino acid at position 613 of SEQ ID NO: 33 (residue E613), amino acid at position 611 of SEQ ID NO: 33 (residue D611) and/or amino acid at position 615 of SEQ ID NO: 33 (residue H615).

The term "$k_d$" ($sec^{-1}$), as used herein, refers to the dissociation rate constant of a particular Ab-antigen interaction ([Ab] [antigen]/[Ab-antigen complex]). Said value is also referred to as the kw value.

The term "$k_a$" ($M^{-1} \times sec^{-1}$), as used herein, refers to the association rate constant of a particular Ab-antigen interaction and is the reciprocal of the $k_d$.

The term "$K_D$" (M), as used herein, refers to the dissociation equilibrium constant of a particular Ab-antigen interaction and is obtained by dividing the $k_d$ by the $k_a$.

The term "$K_A$" ($M^{-1}$), as used herein, refers to the association equilibrium constant of a particular Ab-antigen interaction and is obtained by dividing the $k_a$ by the $k_d$.

As used herein, the terms "neutralizing antibody" refers to an antibody that blocks or reduces at least one activity of a polypeptide comprising the epitope to which the antibody specifically binds. A neutralizing antibody reduces an activity in vitro and/or in vivo.

As used herein "residue E613" refers to the glutamic acid at position 613 in the SEQ ID NO 33

As used herein "residue D611" refers to the aspartic acid at position 611 in the SEQ ID NO 33.

As used herein "residue H615" refers to the histine at position 615 in the SEQ ID NO 33.

The antibodies of the invention may be assayed for specific binding by any method known in the art. Many different competitive binding assay format(s) can be used for epitope binding. The immunoassays which can be used include, but are not limited to, competitive assay systems using techniques such western blots, radioimmunoassays, ELISA, "sandwich" immunoassays, immunoprecipitation assays, precipitin assays, gel diffusion precipitin assays, immunoradiometric assays, fluorescent immunoassays, protein A immunoassays, and complement-fixation assays. Such assays are routine and well known in the art (see, e.g., Ausubel et al., eds, 1994 Current Protocols in Molecular Biology, Vol. 1, John Wiley & sons, Inc., New York).

Antibody Engineering

Engineered antibodies of the invention include those in which modifications have been made to framework residues within VH and/or VL, e.g. to improve the properties of the antibody. Typically such framework modifications are made to decrease the immunogenicity of the antibody. For example, one approach is to "backmutate" one or more framework residues to the corresponding germline sequence. More specifically, an antibody that has undergone somatic mutation may contain framework residues that differ from the germline sequence from which the antibody is derived. Such residues can be identified by comparing the antibody framework sequences to the germline sequences from which the antibody is derived. To return the framework region sequences to their germline configuration, the somatic mutations can be "backmutated" to the germline sequence by, for example, site-directed mutagenesis or PCR-mediated mutagenesis. Such "backmutated" antibodies are also intended to be encompassed by the invention. Another type of framework modification involves mutating one or more residues within the framework region, or even within one or more CDR regions, to remove T cell-epitopes to thereby reduce the potential immunogenicity of the antibody. This approach is also referred to as "deimmunization" and is described in further detail in U.S. Patent Publication No. 20030153043 by Carr et al.

In some embodiments, the glycosylation of an antibody is modified. Glycosylation can be altered to, for example, increase the affinity of the antibody for the antigen. Such carbohydrate modifications can be accomplished by, for example, altering one or more sites of glycosylation within the antibody sequence. For example, one or more amino acid substitutions can be made that result in elimination of one or more variable region framework glycosylation sites to thereby eliminate glycosylation at that site. Such aglycosylation may increase the affinity of the antibody for antigen.

Such an approach is described in further detail in U.S. Pat. Nos. 5,714,350 and 6,350,861 by Co et al.

In some embodiments, some mutations are made to the amino acids localized in aggregation "hotspots" within and near the first CDR (CDR1) to decrease the antibodies susceptibility to aggregation (see Joseph M. Perchiacca et al., Proteins 2011; 79:2637-2647).

The antibodies of the present invention may be of any isotype. The choice of isotype typically will be guided by the desired effector functions. IgG1 and IgG3 are isotypes that mediate such effectors functions as ADCC or CDC, when IgG2 and IgG4 don't or in a lower manner. Either of the human light chain constant regions, kappa or lambda, may be used. If desired, the class of a monoclonal antibody of the present invention may be switched by known methods. Typical, class switching techniques may be used to convert one IgG subclass to another, for instance from IgG1 to IgG2. Thus, the effector function of the monoclonal antibodies of the present invention may be changed by isotype switching to, e.g., an IgG1, IgG2, IgG3, IgG4, IgD, IgA, IgE, or IgM antibody for various therapeutic uses.

In some embodiments, the antibodies of the present invention are full-length antibodies. In some embodiments, the full-length antibodies are IgG1 antibodies. In some embodiments, the full-length antibodies are an IgG3 antibodies.

In some embodiments, the antibodies of the present invention are antibodies of a non-IgG2/4 type, e.g. IgG1 or IgG3 which has been mutated such that the ability to mediate effector functions, such as ADCC, has been reduced or even eliminated. Such mutations have e.g. been described in Dall'Acqua W F et al., J Immunol. 177(2): 1129-1138 (2006) and Hezareh M, J Virol. 75(24): 12161-12168 (2001).

In some embodiments, the hinge region of CH1 is modified such that the number of cysteine residues in the hinge region is altered, e.g., increased or decreased. This approach is described further in U.S. Pat. No. 5,677,425 by Bodmer et al. The number of cysteine residues in the hinge region of CH1 is altered to, for example, facilitate assembly of the light and heavy chains or to increase or decrease the stability of the antibody.

In some embodiments, the Fc region is altered by replacing at least one amino acid residue with a different amino acid residue to alter the effector functions of the antibody. For example, one or more amino acids can be replaced with a different amino acid residue such that the antibody has an altered affinity for an effector ligand but retains the antigen-binding ability of the parent antibody. The effector ligand to which affinity is altered can be, for example, an Fc receptor or the C1 component of complement. This approach is described in further detail in U.S. Pat. Nos. 5,624,821 and 5,648,260, both by Winter et al.

In some embodiments, one or more amino acids selected from amino acid residues can be replaced with a different amino acid residue such that the antibody has altered Clq binding and/or reduced or abolished complement dependent cytotoxicity (CDC). This approach is described in further detail in U.S. Pat. No. 6,194,551 by ldusogie et al.

In some embodiments, one or more amino acid residues are altered to thereby alter the ability of the antibody to fix complement. This approach is described further in PCT Publication WO 94/29351 by Bodmer et al.

In some embodiments, the Fc region is modified to increase the ability of the antibodies to mediate antibody dependent cellular cytotoxicity (ADCC) and/or to increase the affinity of the antibodies for an Fc receptor by modifying one or more amino acids. This approach is described further in PCT Publication WO 00/42072 by Presta. Moreover, the binding sites on human IgGl for FcγRI, FcγRII, FcγRIII and FcRn have been mapped and variants with improved binding have been described (see Shields, R. L. et al., 2001 J. Biol. Chen. 276:6591-6604, WO2010106180).

The term "antibody-dependent cell-mediated cytotoxicity" or "ADCC" is a term well understood in the art, and refers to a cell-mediated reaction in which non-specific cytotoxic cells that express Fc receptors (FcRs) recognize bound antibody on a target cell and subsequently cause lysis of the target cell. Non-specific cytotoxic cells that mediate ADCC include natural killer (NK) cells, macrophages, monocytes, neutrophils, and eosinophils.

"Effector functions" refer to those biological activities attributable to the Fc region of an antibody, which vary with the antibody isotype. Examples of antibody effector functions include: Clq binding and complement dependent cytotoxicity (CDC); Fc receptor binding; antibody-dependent cell-mediated cytotoxicity (ADCC); phagocytosis; down regulation of cell surface receptors (e.g. B cell receptor); and B cell activation.

Additionally or alternatively, an antibody can be made that has an altered type of glycosylation, such as a hypofucosylated or non-fucosylated antibody having reduced amounts of or no fucosyl residues or an antibody having increased bisecting GlcNac structures. Such altered glycosylation patterns have been demonstrated to increase the ADCC ability of antibodies. Such carbohydrate modifications can be accomplished by, for example, expressing the antibody in a host cell with altered glycosylation machinery. Cells with altered glycosylation machinery have been described in the art and can be used as host cells in which to express recombinant antibodies of the present invention to thereby produce an antibody with altered glycosylation. For example, EP1,176,195 by Hang et al. describes a cell line with a functionally disrupted FUT8 gene, which encodes a fucosyl transferase, such that antibodies expressed in such a cell line exhibit hypofucosylation or are devoid of fucosyl residues. Therefore, in some embodiments, the monoclonal antibodies of the present invention may be produced by recombinant expression in a cell line which exhibit hypofucosylation or non-fucosylation pattern, for example, a mammalian cell line with deficient expression of the FUT8 gene encoding fucosyltransferase. PCT Publication WO 03/035835 by Presta describes a variant CHO cell line, Lec13 cells, with reduced ability to attach fucose to Asn (297)-linked carbohydrates, also resulting in hypofucosylation of antibodies expressed in that host cell (see also Shields, R. L. et al, 2002 J. Biol. Chem. 277:26733-26740). PCT Publication WO 99/54342 by Umana et al. describes cell lines engineered to express glycoprotein-modifying glycosyl transferases (e.g., beta(1,4)-N acetylglucosaminyltransferase III (GnTIII)) such that antibodies expressed in the engineered cell lines exhibit increased bisecting GlcNac structures which results in increased ADCC activity of the antibodies (see also Umana et al, 1999 Nat. Biotech. 17: 176-180). Eureka Therapeutics further describes genetically engineered CHO mammalian cells capable of producing antibodies with altered mammalian glycosylation pattern devoid of fucosyl residues. Alternatively, the monoclonal antibodies of the present invention can be produced in yeasts or filamentous fungi engineered for mammalian-like glycosylation pattern and capable of producing antibodies lacking fucose as glycosylation pattern (see for example EP1297172B1).

In another embodiment, the antibodies are modified to increase its biological half-life. Various approaches are possible. For example, one or more of the following mutations can be introduced: T252L, T254S, T256F, as described in U.S. Pat. No. 6,277,375 by Ward. Alternatively, to increase the biological half life, the antibodies can be altered within the CH1 or CL region to contain a salvage receptor binding epitope taken from two loops of a CH2 domain of an Fc region of an IgG, as described in U.S. Pat. Nos. 5,869,046 and 6,121,022 by Presta et al. Antibodies with increased half lives and improved binding to the neonatal Fc receptor (FcRn), which is responsible for the transfer of maternal IgGs to the foetus (Guyer et al., J. Immunol. 117:587 (1976) and Kim et al., J. immunol. 24:249 (1994)), are described in US2005/0014934A1 (Hinton et al.). Those antibodies comprise an Fc region with one or more substitutions therein which improve binding of the Fc region to FcRn. Such Fc variants include those with substitutions at one or more of Fc region residues: 238, 256, 265, 272, 286, 303, 305, 307, 311,312, 317, 340, 356, 360, 362, 376, 378, 380, 382, 413, 424, or 434, e.g., substitutions of Fc region residue 434 (U.S. Pat. No. 7,371,826).

Another modification of the antibodies herein that are contemplated by the invention is pegylation. An antibody can be pegylated to, for example, increase the biological (e.g., serum) half-life of the antibody. To pegylate an antibody, the antibody, or fragment thereof, typically is reacted with polyethylene glycol (PEG), such as a reactive ester or aldehyde derivative of PEG, under conditions in which one or more PEG groups become attached to the antibody or antibody fragment. The pegylation can be carried out by an acylation reaction or an alkylation reaction with a reactive PEG molecule (or an analogous reactive water-soluble polymer). As used herein, the term "polyethylene glycol" is intended to encompass any of the forms of PEG that have been used to derivatize other proteins, such as mono (C1-C10) alkoxy- or aryloxy-polyethylene glycol or polyethylene glycol-maleimide. In certain embodiments, the antibody to be pegylated is an aglycosylated antibody. Methods for pegylating proteins are known in the art and can be applied to the antibodies of the invention. See for example, EP0154316 by Nishimura et al. and EP0401384 by Ishikawa et al.

Another modification of the antibodies that is contemplated by the invention is a conjugate or a protein fusion of at least the antigen-binding region of the antibody of the invention to serum protein, such as human serum albumin or a fragment thereof to increase half-life of the resulting molecule. Such approach is for example described in Ballance et al. EP0322094. Another possibility is a fusion of at least the antigen-binding region of the antibody of the invention to proteins capable of binding to serum proteins, such human serum albumin to increase half-life of the resulting molecule. Such approach is for example described in Nygren et al., EP 0 486 525.

Polysialytion is another technology, which uses the natural polymer polysialic acid (PSA) to prolong the active life and improve the stability of therapeutic peptides and proteins. PSA is a polymer of sialic acid (a sugar). When used for protein and therapeutic peptide drug delivery, polysialic acid provides a protective microenvironment on conjugation. This increases the active life of the therapeutic protein in the circulation and prevents it from being recognized by the immune system. The PSA polymer is naturally found in the human body. It was adopted by certain bacteria which evolved over millions of years to coat their walls with it. These naturally polysialylated bacteria were then able, by virtue of molecular mimicry, to foil the body's defense system. PSA, nature's ultimate stealth technology, can be easily produced from such bacteria in large quantities and with predetermined physical characteristics. Bacterial PSA is completely non-immunogenic, even when coupled to proteins, as it is chemically identical to PSA in the human body.

Another technology includes the use of hydroxyethyl starch ("HES") derivatives linked to antibodies. HES is a modified natural polymer derived from waxy maize starch and can be metabolized by the body's enzymes. HES solutions are usually administered to substitute deficient blood volume and to improve the rheological properties of the blood. Hesylation of an antibody enables the prolongation of the circulation half-life by increasing the stability of the molecule, as well as by reducing renal clearance, resulting in an increased biological activity. By varying different parameters, such as the molecular weight of HES, a wide range of HES antibody conjugates can be customized.

In another embodiment, the Fc hinge region of an antibody is mutated to decrease the biological half-life of the antibody. More specifically, one or more amino acid mutations are introduced into the CH2-CH3 domain interface region of the Fc-hinge fragment such that the antibody has impaired Staphylococcyl protein A (SpA) binding relative to native Fc-hinge domain SpA binding. This approach is described in further detail in U.S. Pat. No. 6,165,745 by Ward et al.

In certain embodiments of the invention the antibodies have been engineered to remove sites of deamidation. Deamidation is known to cause structural and functional changes in a peptide or protein. Deamidation can result in decreased bioactivity, as well as alterations in pharmacokinetics and antigenicity of the protein pharmaceutical. (Anal Chem. 2005 Mar. 1; 77(5):1432-9).

In certain embodiments of the invention the antibodies have been engineered to increase pI and improve their drug-like properties. The pI of a protein is a key determinant of the overall biophysical properties of a molecule. Antibodies that have low pIs have been known to be less soluble, less stable, and prone to aggregation. Further, the purification of antibodies with low pI is challenging and can be problematic especially during scale-up for clinical use. Increasing the pI of the anti-HER4 antibodies of the invention or fragments thereof improved their solubility, enabling the antibodies to be formulated at higher concentrations (>100 mg/ml). Formulation of the antibodies at high concentrations (e.g. >100 mg/ml) offers the advantage of being able to administer higher doses of the antibodies into eyes of patients via intravitreal injections, which in turn may enable reduced dosing frequency, a significant advantage for treatment of chronic diseases including cardiovascular disorders. Higher pIs may also increase the FcRn-mediated recycling of the IgG version of the antibody thus enabling the drug to persist in the body for a longer duration, requiring fewer injections. Finally, the overall stability of the antibodies is significantly improved due to the higher pi resulting in longer shelf-life and bioactivity in vivo. Preferably, the pI is greater than or equal to 8.2.

Glycosylation modifications can also induce enhanced anti-inflammatory properties of the antibodies by addition of sialylated glycans. The addition of terminal sialic acid to the Fc glycan reduces FcγR binding and converts IgG antibodies to anti-inflammatory mediators through the acquisition of novel binding activities (see Robert M. Anthony et al., J Clin Immunol (2010) 30 (Suppl 1): S9-S14; Kai-Ting C et al., Antibodies 2013, 2, 392-414).

Minetics Antibody

In some embodiments, the heavy and light chains, variable regions domains and CDRs that are disclosed can be used to prepare polypeptides that contain antigen binding region that can specifically bind to HER4. For example, one or more of the CDRs listed in Table 1 can be incorporated into a molecule (e.g., a polypeptide) covalently or noncovalently to make an immunoadhesion. An immunoadhesion may incorporate the CDR(s) as part of a larger polypeptide chain, may covalently link the CDR(s) to another polypeptide chain, or may incorporate the CDR(s) noncovalently. The CDR(s) enable the immunoadhesion to bind specifically to a particular antigen of interest (e.g., anti-HER4 or epitope thereof).

The terms "polypeptide" and "protein" are used interchangeably herein to refer to a polymer of amino acid residues. The terms apply to amino acid polymers in which one or more amino acid residues is an artificial chemical mimetic of a corresponding naturally occurring amino acid, as well to naturally occurring amino acids polymers and non-naturally occurring amino acid polymers. Unless otherwise indicated, a particular polypeptide sequence also implicitly encompasses conservatively modified variants thereof.

In some embodiments, the antigen biding fragment of the invention is grafted into non-immunoglobulin based antibodies also called antibody mimetics selected from the group consisting of an affibody, an affilin, an affitin, an adnectin, an atrimer, an evasin, a DARPin, an anticalin, an avimer, a fynomer, and a versabody.

The term "antibody mimetic" is intended to refer to molecules capables of mimicking an antibody's ability to bind an antigen, but which are not limited to native antibody structures. Examples of such antibody mimetics include, but are not limited to, Adnectins, Affibodies, DARPins, Anticalins, Avimers, and versabodies, all of which employ binding structures that, while they mimic traditional antibody binding, are generated from and function via distinct mechanisms. Antigen biding fragments of antibodies can be grafted into scaffolds based on polypeptides such as Fibronectin type III (Fn3) (see U.S. Pat. No. 6,703,199, which describes fibronectin polypeptide monobodies). An affibody is well known in the art and refers to affinity proteins based on a 58 amino acid residue protein domain, derived from one of the IgG binding domain of staphylococcal protein A. DARPins (Designed Ankyrin Repeat Proteins) are well known in the art and refer to an antibody mimetic DRP (designed repeat protein) technology developed to exploit the binding abilities of non-antibody proteins. Anticalins are well known in the art and refer to another antibody mimetic technology, wherein the binding specificity is derived from lipocalins. Anticalins may also be formatted as dual targeting protein, called Duocalins. Avimers are well known in the art and refer to another antibody mimetic technology, Avimers are derived from natural A-domain containing protein. Versabodies are well known in the art and refer to another antibody mimetic technology, they are small proteins of 3-5 kDa with >15% cysteines, which form a high disulfide density scaffold, replacing the hydrophobic core the typical proteins have. Such antibody mimetic can be comprised in a scaffold. The term "scaffold" refers to a polypeptide platform for the engineering of new products with tailored functions and characteristics.

In one aspect, the invention pertains to generating non-immunoglobulin based antibodies also called antibody mimetics using non-immunoglobulins scaffolds onto which CDRs of the invention can be grafted. Known or future non-immunoglobulin frameworks and scaffolds may be employed, as long as they comprise a binding region specific for the target anti-HER4 protein.

The fibronectin scaffolds are based on fibronectin type III domain (e.g., the tenth module of the fibronectin type III (10 Fn3 domain)). The fibronectin type III domain has 7 or 8 beta strands which are distribued between two beta sheets, which themselves pack against each other to form the core of the protein, and further containing loops (analogous to CDRs) which connect the beta strands to each other and are solvent exposed. There are at least three such loops at each edge of the beta sheet sandwich, where the edge is the boundary of the protein perpendicular to the direction of the beta strands (see U.S. Pat. No. 6,818,418). These fibronectin-based scaffolds are not an immunoglobulin, although the overall fold is closely related to that of the smallest functional antibody fragment, the variable region of the heavy chain, which comprise the entire antigen recognition unit in camel and llama IgG. Because of this structure, the non-immunoglobulin antibody mimics antigen binding properties that are similar in nature and affinity to those of antibodies. These scaffolds can be used in a loop randomisation and shuffling strategy in vitro that is similar to the process of affinity maturation of antibodies in vivo. These fibronectin-based molecules can be used as scaffolds where the loop regions of the molecule can be replaced with CDRs of the invention using standard cloning techniques.

The Ankyrin technology is based on using proteins with Ankyrin derived repeat modules as scaffolds for bearing variable regions which can be used for binding to different targets. The Ankyrin repeat module is a 33 amino acid polypeptide consisting of two anti-parallel $\alpha$-helices and a $\beta$-turn. Binding of the variable regions is mostly optimized by using ribosome display.

Avimers are derived from natural A-domain containing protein such as LRP-1. These domains are used by nature for protein-protein interactions and in human over 250 proteins are structurally based on "A-domains" monomers (2-10) linked via amino acids linkers. Avimers can be created that can bind to the target antigen using the methodology described in, for example, U.S. patent Application publication Nos. 20040175756; 20050053973; 20050048512; and 20060008844.

Affibody affinity ligands are small, simple proteins composed of a three-helix bundle based on the scaffold of one of the IgG-binding domains of protein A. protein A is a surface protein form the bacterium Staphylococcus aureus. This scaffold domain consist of 58 amino acids, 13 of which are randomized to generate affibody libraries with a large number of ligand variants (See e.g., U.S. Pat. No. 5,831,012). Affibody molecules mimic antibodies, they have a molecular weight of 6 kDa. In spite of its small size, the binding site of affibody molecules is similar to that of an antibody.

Anticalins are products developed by the company Pieris ProteoLab AG. They are derived from lipocalins, a widespread group of small and robust proteins that are usually involved in the physiological transport or storage of chemically sensitive or insoluble compounds. Several natural lipocalins occur in human tissues or body liquids. The protein architecture is reminiscent of immunoglobulins, with hypervariable loops on top of a rigid framework. However, in contrast with antibodies or their recombinant fragments, lipocalins are composed of a single polypeptide chain with 160 to 180 amino acids residues, being just marginally bigger than a single immunoglobulin domain. The set of four loops, which makes up the binding pocket, shows pronounced structural plasticity and tolerates a variety of side chains. The binding site can can thus be reshaped in a proprietary process in order to recognize prescribed target molecules of different shape with high affinity and specificity. One protein of lipocalin family, the bilin-binding protein (BBP) of *Pieris Brassicae* has been used to develop anticalins by mutagenizing the set of four loops. One example of a patent application describing anticalins is in PCT Publication No. WO 199916873.

Affilin molecules are small non-immunoglobulin proteins which are designed for specific affinities towards proteins and small molecules. New affilin molecules can be very quickly selected from two libraries, each of which is based on a different human derived scaffold protein. Affilin molecules do not show any structural homology to immunoglobulin proteins. Currently, two affilin scaffolds are employed, one of which is gamma crystalline, a human structural eye lens protein and the other is "ubiquitin" superfamily proteins. Both human scaffolds are very small, show high temperature stability and are almost resistant to pH changes and denaturing agents. This high stability is mainly due to the expanded beta sheet structure of the proteins. Examples of "ubiquitin-like" proteins are described in WO2004106368.

Versabodies are highly soluble and can be formulated to high concentrations. Versabodies are exceptionally heat stable and offer extended shelf-life. Additional information regarding Versabodies can be found in US 2007/0191272, which is hereby incorporated by reference in its entirety.

The above descriptions of antibody fragment and mimetic technologies is not intended to be comprehensive. A variety of additional technologies including alternative polypeptide-based technologies, such as fusions of complementarity determining regions as outlined in Qui et al., Nature Biotechnology, 25(8) 921-929 (2007), as well as nucleic acid-based technologies, such as the RNA aptamer technologies described in U.S. Pat. Nos. 5,789,157; 5,864,026; 5,712,375; 5,763,566; 6,013,443; 6,376,474; 6,613,526; 6,114,120; 6,261,774; and 6,387,620; all of which are hereby incorporated by reference, could be used in the context of the instant invention.

CAR-T Cells

The present invention also provides chimeric antigen receptors (CARs) comprising an antigen binding domain of the antibodies of the present invention. Typically, said chimeric antigen receptor comprises at least one VH and/or VL sequence of the antibodies of the present invention. The chimeric antigen receptor of the present invention also comprises an extracellular hinge domain, a transmembrane domain, and an intracellular T cell signaling domain.

As used herein, the term "chimeric antigen receptor" or "CAR" has its general meaning in the art and refers to an artificially constructed hybrid protein or polypeptide containing the antigen binding domains of an antibody (e.g., scFv) linked to T-cell signaling domains. Characteristics of CARS include their ability to redirect T-cell specificity and reactivity toward a selected target in a non-MHC-restricted manner, exploiting the antigen-binding properties of monoclonal antibodies. The non-MHC-restricted antigen recognition gives T cells expressing CARS the ability to recognize antigen independent of antigen processing, thus bypassing a major mechanism of tumor escape. Moreover, when expressed in T-cells, CARS advantageously do not dimerize with endogenous T cell receptor (TCR) alpha and beta chains.

In some embodiments, the invention provides CARs comprising an antigen-binding domain comprising, consisting of, or consisting essentially of, a single chain variable fragment (scFv) of the C6 mAb, D5 mAb, F4 mAb and H2 mAb. In some embodiments, the antigen binding domain comprises a linker peptide. The linker peptide may be positioned between the light chain variable region and the heavy chain variable region.

In some embodiments, the CAR comprises an extracellular hinge domain, a transmembrane domain, and an intracellular T cell signaling domain selected from the group consisting of CD28, 4-1BB, and CD3ζ intracellular domains. CD28 is a T cell marker important in T cell co-stimulation. 4-1BB transmits a potent costimulatory signal to T cells, promoting differentiation and enhancing long-term survival of T lymphocytes. CD3ζ associates with TCRs to produce a signal and contains immunoreceptor tyrosine-based activation motifs (ITAMs).

In some embodiments, the chimeric antigen receptor of the present invention can be glycosylated, amidated, carboxylated, phosphorylated, esterified, N-acylated, cyclized via, e.g., a disulfide bridge, or converted into an acid addition salt and/or optionally dimerized or polymerized.

The invention also provides a nucleic acid encoding for a chimeric antigen receptor of the present invention. In some embodiments, the nucleic acid is incorporated in a vector as such as described above.

The present invention also provides a host cell comprising a nucleic acid encoding for a chimeric antigen receptor of the present invention. While the host cell can be of any cell type, can originate from any type of tissue, and can be of any developmental stage; the host cell is a T cell, e.g. isolated from peripheral blood lymphocytes (PBL) or peripheral blood mononuclear cells (PBMC). In some embodiments, the T cell can be any T cell, such as a cultured T cell, e.g., a primary T cell, or a T cell from a cultured T cell line, e.g., Jurkat, SupTl, etc., or a T cell obtained from a mammal. If obtained from a mammal, the T cell can be obtained from numerous sources, including but not limited to blood, bone marrow, lymph node, the thymus, or other tissues or fluids. T cells can also be enriched for or purified. The T cell can be any type of T cell and can be of any developmental stage, including but not limited to, CD4+/CD8+ double positive T cells, CD4+ helper T cells, e.g., Th2 cells, CD8+ T cells (e.g., cytotoxic T cells), tumor infiltrating cells, memory T cells, naive T cells, and the like. The T cell may be a CD8+ T cell or a CD4+ T cell.

The population of those T cells prepared as described above can be utilized in methods and compositions for adoptive immunotherapy in accordance with known techniques, or variations thereof that will be apparent to those skilled in the art based on the instant disclosure. See, e.g., US Patent Application Publication No. 2003/0170238 to Gruenberg et al; see also U.S. Pat. No. 4,690,915 to Rosenberg. Adoptive immunotherapy of cancer refers to a therapeutic approach in which immune cells with an antitumor reactivity are administered to a tumor-bearing host, with the aim that the cells mediate either directly or indirectly, the regression of an established tumor. Transfusion of lymphocytes, particularly T lymphocytes, falls into this category. Currently, most adoptive immunotherapies are autolymphocyte therapies (ALT) directed to treatments using the patient's own immune cells. These therapies involve processing the patient's own lymphocytes to either enhance the immune cell mediated response or to recognize specific antigens or foreign substances in the body, including the cancer cells. The treatments are accomplished by removing the patient's lymphocytes and exposing these cells in vitro to biologics and drugs to activate the immune function of the cells. Once the autologous cells are activated, these ex vivo activated cells are reinfused into the patient to enhance the immune system to treat cancer. In some embodiments, the cells are formulated by first harvesting them from their culture medium, and then washing and concentrating the cells in a medium and container system suitable for administration (a "pharmaceutically acceptable" carrier) in a treatment-effective amount. Suitable infusion medium can be any isotonic medium formulation, typically normal saline, Normosol R (Abbott) or Plasma-Lyte A (Baxter), but also 5% dextrose in water or Ringer's lactate can be utilized. The infusion medium can be supplemented with human serum albumin. A treatment-effective amount of cells in the composition is dependent on the relative representation of the T cells with the desired specificity, on the age and weight of the recipient, on the severity of the targeted condition and on the immunogenicity of the targeted Ags. These amount of cells can be as low as approximately $10^3$/kg, preferably $5 \times 10^3$/kg; and as high as $10^7$/kg, preferably $10^8$/kg. The number of cells will depend upon the ultimate use for which the composition is intended, as will the type of cells included therein. For example, if cells that are specific for a particular Ag are desired, then the population will contain greater than 70%, generally greater than 80%, 85% and 90-95% of such cells. For uses provided herein, the cells are generally in a volume of a liter or less, can be 500 ml or less, even 250 ml or 100 ml or less. The clinically relevant number of immune cells can be apportioned into multiple infusions that cumulatively equal or exceed the desired total amount of cells.

In particular the cells of the present invention are particularly suitable for the treatment of cancer. Accordingly, a further object of the present invention relates to a method of treating cancer in a subject in need thereof comprising administering to the subject a therapeutically effective amount of a population of cells of the present invention.

Multispecific Antibodies

In some embodiments, the invention provides multispecific antibodies comprising a first antigen binding site from antibodies of the present invention molecule described herein above and at least one second antigen binding site.

In some embodiments, the second antigen-binding site is used for recruiting a killing mechanism such as, for example, by binding an antigen on a human effector cell as a BiTE (Bispecific T-Cell engager) antibody which is a bispecific scFv2 directed against target antigen and CD3 on T cells described in U.S. Pat. No. 7,235,641, or by binding a cytotoxic agent or a second therapeutic agent. As used herein, the term "effector cell" refers to an immune cell which is involved in the effector phase of an immune response, as opposed to the cognitive and activation phases of an immune response. Exemplary immune cells include a cell of a myeloid or lymphoid origin, for instance lymphocytes (such as B cells and T cells including cytolytic T cells (CTLs)), killer cells, natural killer cells, macrophages, monocytes, mast cells and granulocytes, such as neutrophils, eosinophils and basophils. Some effector cells express specific Fc receptors (FcRs) and carry out specific immune functions. In some embodiments, an effector cell is capable of inducing ADCC, such as a natural killer cell. For example, monocytes, macrophages, which express FcRs, are involved in specific killing of target cells and presenting antigens to other components of the immune system. In some embodiments, an effector cell may phagocytose a target antigen or target cell. The expression of a particular FcR on an effector cell may be regulated by humoral factors such as cytokines. An effector cell can phagocytose a target antigen or phagocytose or lyse a target cell. Suitable cytotoxic agents and second therapeutic agents are exemplified below, and include toxins (such as radiolabeled peptides), chemotherapeutic agents and prodrugs In some embodiments, the second antigen-binding site binds to an antigen on a human B cell, such as, e.g., CD19, CD20, CD21, CD22, CD23, CD46, CD80, CD138 and HLA-DR.

In some embodiments, the second antigen-binding site binds a tissue-specific antigen, promoting localization of the bispecific antibody to a specific tissue.

In some embodiments, the second antigen-binding site binds to an antigen located on the same type of cell as the HER4-expressing cell, typically a tumor-associated antigen (TAA), but has a binding specificity different from that of the first antigen-binding site. Such multi- or bispecific antibodies can enhance the specificity of the tumor cell binding and/or engage multiple effector pathways. Exemplary TAAs include carcinoembryonic antigen (CEA), prostate specific antigen (PSA), RAGE (renal antigen), a-fetoprotein, CAMEL (CTL-recognized antigen on melanoma), CT antigens (such as MAGE-B5, -B6, -C2, -C3, and D; Mage-12; CT10; NY-ESO-1, SSX-2, GAGE, BAGE, MAGE, and SAGE), mucin antigens (e.g., MUC1, mucin-CA125, etc.), ganglioside antigens, tyrosinase, gp75, c-Met, Marti, MelanA, MUM-1, MUM-2, MUM-3, HLA-B7, Ep-CAM or a cancer-associated integrin, such as $\alpha 5\beta 3$ integrin. Alternatively, the second antigen-binding site binds to a different epitope of HER4. The second antigen-binding site may alternatively bind an angiogenic factor or other cancer-associated growth factor, such as a vascular endothelial growth factor, a fibroblast growth factor, epidermal growth factor, angiogenin or a receptor of any of these, particularly receptors associated with cancer progression.

In some embodiments, the second antigen-binding site is from a second antibody or ADC of the invention, such as the antibodies of the present invention.

Exemplary formats for the multispecific antibodies molecules of the invention include, but are not limited to (i) two antibodies cross-linked by chemical heteroconjugation, one with a specificity to HER4 and another with a specificity to a second antigen; (ii) a single antibody that comprises two different antigen-binding regions; (iii) a single-chain antibody that comprises two different antigen-binding regions, e.g., two scFvs linked in tandem by an extra peptide linker; (iv) a dual-variable-domain antibody (DVD-Ig), where each light chain and heavy chain contains two variable domains in tandem through a short peptide linkage (Wu et al., Generation and Characterization of a Dual Variable Domain Immunoglobulin (DVD-Ig™) Molecule, In: Antibody Engineering, Springer Berlin Heidelberg (2010)); (v) a chemically-linked bispecific (Fab')2 fragment; (vi) a Tandab, which is a fusion of two single chain diabodies resulting in a tetravalent bispecific antibody that has two binding sites for each of the target antigens; (vii) a flexibody, which is a combination of scFvs with a diabody resulting in a multivalent molecule; (viii) a so called "dock and lock" molecule, based on the "dimerization and docking domain" in Protein Kinase A, which, when applied to Fabs, can yield a trivalent bispecific binding protein consisting of two identical Fab fragments linked to a different Fab fragment; (ix) a so-called Scorpion molecule, comprising, e.g., two scFvs fused to both termini of a human Fab-arm; and (x) a diabody. Another exemplary format for bispecific antibodies is IgG-like molecules with complementary CH3 domains to force heterodimerization. Such molecules can be prepared using known technologies, such as, e.g., those known as Triomab/ Quadroma (Trion Pharma/Fresenius Biotech), Knob-into-Hole (Genentech), CrossMAb (Roche) and electrostaticallymatched (Amgen), LUZ-Y (Genentech), Strand Exchange Engineered Domain body (SEEDbody)(EMD Serono), Biclonic (Merus) and DuoBody (Genmab A/S) technologies.

In some embodiments, the bispecific antibodies are obtained or obtainable via a controlled Fab-arm exchange, typically using DuoBody technology. In vitro methods for producing bispecific antibodies by controlled Fab-arm exchange have been described in WO2008119353 and WO 2011131746 (both by Genmab A/S). In one exemplary method, described in WO 2008119353, a bispecific antibody is formed by "Fab-arm" or "half-molecule" exchange (swapping of a heavy chain and attached light chain) between two monospecific antibodies, both comprising IgG4-like CH3 regions, upon incubation under reducing conditions. The resulting product is bispecific antibodies having a heavy chain having at least 70, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or 100% of identity with SEQ ID NO: 1, SEQ ID NO: 9, SEQ ID NO: 17 or SEQ ID NO: 25 and a light chain having at least 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or 100% of identity with SEQ ID NO: 5, SEQ ID NO: 13, SEQ ID NO: 21 or SEQ ID NO: 29 antibodies having two Fab arms which may comprise different sequences. In another exemplary method, described in WO 2011131746, bispecific antibodies of the present invention are prepared by a method comprising the following steps, wherein at least one of the first and second antibodies is the antibody of the present invention: a) providing a first antibody comprising an Fc region of an immunoglobulin, said Fc region comprising a first CH3 region; b) providing a second antibody comprising an Fc region of an immunoglobulin, said Fc region comprising a second CH3 region; wherein the sequences of said first and second CH3 regions are different and are such that the heterodimeric interaction between said first and second CH3 regions is stronger than each of the homodimeric interactions of said first and second CH3 regions; c) incubating said first antibody together with said second antibody under reducing conditions; and d) obtaining said bispecific antibody, wherein the first antibody is the antibody of the present invention and the second antibody has a different binding specificity, or vice versa. The reducing conditions may, for example, be provided by adding a reducing agent, e.g. selected from 2-mercaptoethylamine, dithiothreitol and tris(2-carboxyethyl)phosphine. Step d) may further comprise restoring the conditions to become non-reducing or less reducing, for example by removal of a reducing agent, e.g. by desalting. Preferably, the sequences of the first and second CH3 regions are different, comprising only a few, fairly conservative, asymmetrical mutations, such that the heterodimeric interaction between said first and second CH3 regions is stronger than each of the homodimeric interactions of said first and second CH3 regions. More details on these interactions and how they can be achieved are provided in WO 2011131746, which is hereby incorporated by reference in its entirety. The following are exemplary embodiments of combinations of such assymetrical mutations, optionally wherein one or both Fc-regions are of the IgG1 isotype.

In some embodiments, the first Fc region has an amino acid substitution at a position selected from the group consisting of: 366, 368, 370, 399, 405, 407 and 409, and the second Fc region has an amino acid substitution at a position selected from the group consisting of: 366, 368, 370, 399, 405, 407 and 409, and wherein the first and second Fc regions are not substituted in the same positions.

In some embodiments, the first Fc region has an amino acid substitution at position 405, and said second Fc region has an amino acid substitution at a position selected from the group consisting of: 366, 368, 370, 399, 407 and 409, optionally 409.

In some embodiments, the first Fc region has an amino acid substitution at position 409, and said second Fc region has an amino acid substitution at a position selected from the group consisting of: 366, 368, 370, 399, 405, and 407, optionally 405 or 368.

In some embodiments, both the first and second Fc regions are of the IgG1 isotype, with the first Fc region having a Leu at position 405, and the second Fc region having an Arg at position 409.

VHH

In some embodiments, the polypeptide comprises at least one single domain antibody of the invention and at least one other binding unit (i.e. directed against another epitope, antigen, target, protein or polypeptide), which is typically also a single domain antibody. Such a polypeptide is referred to herein as "multispecific" polypeptide; in opposition to a polypeptide comprising the same single domain antibodies ("monospecific" polypeptide). Thus, in some embodiments, the polypeptide of the invention may also provide at least one further binding site directed against any desired protein, polypeptide, antigen, antigenic determinant or epitope. Said binding site is directed against to the same protein, polypeptide, antigen, antigenic determinant or epitope for which the single domain antibody of the invention is directed against, or may be directed against a different protein, polypeptide, antigen, antigenic determinant or epitope) from the single domain antibodies of the invention.

Typically, the one or more further binding site may comprise one or more parts, fragments or domains of conventional chain antibodies (and in particular human antibodies) and/or of heavy chain antibodies. For example, a single domain antibody of the invention may be linked to a conventional (typically human) VH or VL optionally via a linker sequence.

A "bispecific" polypeptide of the invention is a polypeptide that comprises at least one single domain antibody directed against a first antigen (i.e. anti-HER4) and at least one further binding site directed against a second antigen (i.e. different from anti-HER4), whereas a "trispecific" polypeptide of the invention is a polypeptide that comprises at least one single domain antibody directed against a first antigen (i.e. anti-HER4), at least one further binding site directed against a second antigen (i.e. different from anti-HER4) and at least one further binding site directed against a third antigen (i.e. different from both i.e. first and second antigen); etc.

In some embodiments, the further binding site is directed against an activating trigger molecule on an effector cell. Typically, said activating trigger molecule is selected from the group consisting of CD3, CD4, CD8, CD25, CD28, CD26, CTLA-4, ICOS, or CD11a. Other suitable antigens include but are not limited to those associated with immune cells including T cell-associated molecules, such as TCR/CD3 or CD2; NK cell-associated targets such as NKG2D, FcγRIIIa (CD16), CD38, CD44, CD56, or CD69; granulocyte-associated targets such as FcγRI (CD64), FcaRI (CD89), and CR3 (CD11b/CD18); monocyte/macrophage-associated targets (such as FcγRI (CD64), FcaRI (CD89), CD3 (CD11b/CD18), or mannose receptor; dendritic cell-associated targets such as FcγRI (CD64) or mannose receptor; and erythrocyte-associated targets such as CRI (CD35).

In some embodiments, the polypeptide is as described in WO2006064136. In particular the polypeptide may consist of i) a first fusion protein wherein the CL constant domain of an antibody is fused by its N-terminal end to the C-terminal end to single domain antibodies according to the invention (i.e. a single antibody directed against anti-HER4) and ii) a second fusion protein wherein the CH1 constant domain of an antibody is fused by its N-terminal end to the C-terminal end of a single domain antibody directed against an antigen different from anti-HER4. In another particular embodiment, the polypeptide consists of a first fusion protein wherein the CH1 constant domain of an antibody is fused by its N-terminal end to the C-terminal end of a single domain antibody directed against a an activating trigger molecule on an effector cell (e.g. CD16) and a second fusion protein wherein the CL constant domain of an antibody is fused by its N-terminal end to the C-terminal end to single domain antibodies of the invention (i.e. EGFR).

In some embodiments, the polypeptide is a biparatopic polypeptide. As used herein, the term "biparatopic" polypeptide means a polypeptide comprising a single domain antibody and a second single domain antibody as herein defined, wherein these two single domain antibodies are capable of binding to two different epitopes of one antigen (e.g. anti-HER4), which epitopes are not normally bound at the same time by one monospecific immunoglobulin, such as e.g. a conventional antibody or one single domain antibody. The biparatopic polypeptides according to the invention are composed of single domain antibodies which have different epitope specificities, and do not contain mutually complementary variable domain pairs which bind to the same epitope. They do therefore not compete with each other for binding to anti-HER4.

In some embodiments, the biparatopic polypeptides of the present invention comprises C6, D5, F4 or H2 mab derivatives as defined above. In some embodiments, the biparatopic polypeptides of the present invention comprises i) a first single domain antibody comprising a CDR1 having least 70% of identity with sequences set forth as SEQ ID NO:6, SEQ ID NO:14, SEQ ID NO:22 or SEQ ID NO:30, a CDR2 having at least 70% of identity with sequences set forth as SEQ ID NO:7, SEQ ID NO:15, SEQ ID NO:23 or SEQ ID NO:31 and a CDR3 having at least 70% of identity with sequence set forth as SEQ ID NO:8, SEQ ID NO:16, SEQ ID NO: 24 or SEQ ID NO:32 and ii) a second single domain antibody ("C6, D5, F4 or H2 mab derivatives") comprising a CDR1 having least 70% of identity with sequences set forth as SEQ ID NO:2, SEQ ID NO:10, SEQ ID NO:18 or SEQ ID NO:26, a CDR2 having at least 70% of identity with sequences set forth as SEQ ID NO:3, SEQ ID NO:11, SEQ ID NO:19 or SEQ ID NO:27 and a CDR3 having at least 70% of identity with sequence set forth as SEQ ID NO:4, SEQ ID NO:12, SEQ ID NO:20 or SEQ ID NO:28. In some embodiments, the biparatopic antibodies of the present invention comprises i) a first single domain antibody comprising a CDR1 having sequences set forth as SEQ ID NO:6, SEQ ID NO:14, SEQ ID NO:22 or SEQ ID NO:30, a CDR2 having sequences set forth as SEQ ID NO:7, SEQ ID NO:15, SEQ ID NO:23 or SEQ ID NO:31 and a CDR3 having sequences set forth as SEQ ID NO:8, SEQ ID NO:16, SEQ ID NO: 24 or SEQ ID NO:32 and ii) a second single domain antibody comprising a CDR1 having a sequence set forth as SEQ ID NO:2, SEQ ID NO:10, SEQ ID NO:18 or SEQ ID NO:26, a CDR2 having sequences set forth as SEQ ID NO:3, SEQ ID NO:11, SEQ ID NO:19 or SEQ ID NO:27 and a CDR3 having sequence set forth as SEQ ID NO:4, SEQ ID NO:12, SEQ ID NO:20 or SEQ ID NO:28. In some embodiments, the biparatopic polypeptides of the present invention comprises i) a first single domain antibody having the sequence set forth as SEQ ID NO: 1, SEQ ID NO: 9, SEQ ID NO: 17 or SEQ ID NO: 25 and ii) a second single domain antibody having the sequence set forth as SEQ ID NO: 5 SEQ ID NO: 13, SEQ ID NO: 21 or SEQ ID NO: 29.

In some embodiments, the two single domain antibodies of the biparatopic polypeptides of the present invention can be linked to each other directly (i.e. without use of a linker) or via a linker. The linker is typically a linker peptide and will, according to the invention, be selected so as to allow binding of the two single domain antibodies to each of their at least two different epitopes of anti-HER4. Suitable linkers inter alia depend on the epitopes and, specifically, the distance between the epitopes on anti-HER4 to which the single domain antibodies bind, and will be clear to the skilled person based on the disclosure herein, optionally after some limited degree of routine experimentation. Also, when the two single domain antibodies that bind to anti-HER4 may also be linked to each other via a third single domain antibody (in which the two single domain antibodies may be linked directly to the third domain antibody or via suitable linkers). Such a third single domain antibody may for example be a single domain antibody that provides for an increased half-life. For example, the latter single domain antibody may be a single domain antibody that is capable of binding to a (human) serum protein such as (human) serum albumin or (human) transferrin, as further described herein. In some embodiments, two or more single domain antibodies that bind to anti-HER4 are linked in series (either directly or via a suitable linker) and the third (single) single domain antibody (which may provide for increased half-life, as decribed above) is connected directly or via a linker to one of these two or more aforementioned single domain antibodies. Suitable linkers are described herein in connection with specific polypeptides of the invention and may—for example and without limitation—comprise an amino acid sequence, which amino acid sequence preferably has a length of 9 or more amino acids, more preferably at least 17 amino acids, such as about 20 to 40 amino acids. However, the upper limit is not critical but is chosen for reasons of convenience regarding e.g. biopharmaceutical production of such polypeptides. The linker sequence may be a naturally occurring sequence or a non-naturally occurring sequence. If used for therapeutical purposes, the linker is preferably non-immunogenic in the subject to which the anti-HER4 polypeptides of the invention are administered. One useful group of linker sequences are linkers derived from the hinge region of heavy chain antibodies as described in WO 96/34103 and WO 94/04678. Other examples are poly-alanine linker sequences such as Ala-Ala-Ala. Further preferred examples of linker sequences are Gly/Ser linkers of different length including (gly4ser)3, (gly4ser)4, (gly4ser), (gly3ser), gly3, and (gly3ser2)3.

In some embodiments, the biparatopic polypeptides have a sequence selected from the group consisting of SEQ ID NO: 1, SEQ ID NO: 9, SEQ ID NO: 17 or SEQ ID NO: 25 and SEQ ID NO: 5 SEQ ID NO: 13, SEQ ID NO: 21 or SEQ ID NO: 29.

Immunoconjugates

The antibodies of the invention can be conjugated with a detectable label to form an anti-HER4 immunoconjugate. Suitable detectable labels include, for example, a radioisotope, a fluorescent label, a chemiluminescent label, an enzyme label, a bioluminescent label or colloidal gold. Methods of making and detecting such detectably-labeled immunoconjugates are well-known to those of ordinary skill in the art, and are described in more detail below. The detectable label can be a radioisotope that is detected by autoradiography. Isotopes that are particularly useful for the purpose of the invention are $^3$H, $^{125}$I, $^{131}$I, $^{35}$S and $^{14}$C.

Anti-HER4 immunoconjugates can also be labeled with a fluorescent compound. The presence of a fluorescently-labeled antibody is determined by exposing the immunoconjugate to light of the proper wavelength and detecting the resultant fluorescence. Fluorescent labeling compounds include fluorescein isothiocyanate, rhodamine, phycoerytherin, phycocyanin, allophycocyanin, o-phthaldehyde and fluorescamine.

Alternatively, anti-HER4 immunoconjugates can be detectably labeled by coupling an antibody to a chemiluminescent compound. The presence of the chemiluminescent-tagged immunoconjugate is determined by detecting the presence of luminescence that arises during the course of a chemical reaction. Examples of chemiluminescent labeling compounds include luminol, isoluminol, an aromatic acridinium ester, an imidazole, an acridinium salt and an oxalate ester.

Similarly, a bioluminescent compound can be used to label anti-HER4 immunoconjugates of the invention. Bioluminescence is a type of chemiluminescence found in biological systems in which a catalytic protein increases the efficiency of the chemiluminescent reaction. The presence of a bioluminescent protein is determined by detecting the presence of luminescence. Bioluminescent compounds that are useful for labeling include luciferin, luciferase and aequorin.

Alternatively, anti-HER4 immunoconjugates can be detectably labeled by linking an anti-HER4 antibody to an enzyme. When the anti-HER4-enzyme conjugate is incubated in the presence of the appropriate substrate, the enzyme moiety reacts with the substrate to produce a chemical moiety which can be detected, for example, by spectrophotometric, fluorometric or visual means. Examples of enzymes that can be used to detectably label polyspecific immunoconjugates include β-galactosidase, glucose oxidase, peroxidase and alkaline phosphatase.

Those of skill in the art will know of other suitable labels which can be employed in accordance with the invention. The binding of marker moieties to anti-HER4 monoclonal antibodies can be accomplished using standard techniques known to the art. Typical methodology in this regard is described by Kennedy et al., *Clin. Chim. Acta* 70:1, 1976; Schurs et al., *Clin. Chim. Acta* 81:1, 1977; Shih et al., *Int'l J. Cancer* 46:1101, 1990; Stein et al., *Cancer Res.* 50:1330, 1990; and Coligan, supra.

Moreover, the convenience and versatility of immunochemical detection can be enhanced by using anti-HER4 monoclonal antibodies that have been conjugated with avidin, streptavidin, and biotin. (See, e.g., Wilchek et al. (eds.), "Avidin-Biotin Technology," *Methods In Enzymology* (Vol. 184) (Academic Press 1990); Bayer et al., "Immunochemical Applications of Avidin-Biotin Technology," in *Methods In Molecular Biology* (Vol. 10) 149-162 (Manson, ed., The Humana Press, Inc. 1992).)

Methods for performing immunoassays are well-established. (See, e.g., Cook and Self, "Monoclonal Antibodies in Diagnostic Immunoassays," in *Monoclonal Antibodies: Production, Engineering, and Clinical Application* 180-208 (Ritter and Ladyman, eds., Cambridge University Press 1995); Perry, "The Role of Monoclonal Antibodies in the Advancement of Immunoassay Technology," in *Monoclonal Antibodies: Principles and Applications* 107-120 (Birch and Lennox, eds., Wiley-Liss, Inc. 1995); Diamandis, *Immunoassay* (Academic Press, Inc. 1996).)

In some embodiments, the antibodies of the present invention are conjugated to a therapeutic moiety, i.e. a drug. The therapeutic moiety can be, e.g., a cytotoxin, a chemotherapeutic agent, a cytokine, an immunosuppressant, an immune stimulator, a lytic peptide, or a radioisotope. Such conjugates are referred to herein as an "antibody-drug conjugates" or "ADCs".

In some embodiments, the antibodies are conjugated to a cytotoxic moiety. The cytotoxic moiety may, for example, be selected from the group consisting of TAXOL® (paclitaxel); cytochalasin B; gramicidin D; ethidium bromide; emetine; mitomycin; etoposide; tenoposide; vincristine; vinblastine; colchicin; doxorubicin; daunorubicin; dihydroxy anthracin dione; a tubulin-inhibitor such as maytansine or an analog or derivative thereof; an antimitotic agent such as monomethyl auristatin E or F or an analog or derivative thereof; dolastatin 10 or 15 or an analogue thereof; irinotecan or an analogue thereof; mitoxantrone; mithramycin; actinomycin D; 1-dehydrotestosterone; a glucocorticoid; procaine; tetracaine; lidocaine; propranolol; puromycin; calicheamicin or an analog or derivative thereof; an antimetabolite such as methotrexate, 6 mercaptopurine, 6 thioguanine, cytarabine, fludarabin, 5 fluorouracil, decarbazine, hydroxyurea, asparaginase, gemcitabine, or cladribine; an alkylating agent such as mechlorethamine, thioepa, chlorambucil, melphalan, carmustine (BSNU), lomustine (CCNU), cyclophosphamide, busulfan, dibromomannitol, streptozotocin, dacarbazine (DTIC), procarbazine, mitomycin C; a platinum derivative such as cisplatin or carboplatin; duocarmycin A, duocarmycin SA, rachelmycin (CC-1065), or an analog or derivative thereof; an antibiotic such as dactinomycin, bleomycin, daunorubicin, doxorubicin, idarubicin, mithramycin, mitomycin, mitoxantrone, plicamycin, anthramycin (AMC)); pyrrolo[2,1-c][1,4]-benzodiazepines (PDB); diphtheria toxin and related molecules such as diphtheria A chain and active fragments thereof and hybrid molecules, ricin toxin such as ricin A or a deglycosylated ricin A chain toxin, cholera toxin, a Shiga-like toxin such as SLT I, SLT II, SLT IIV, LT toxin, C3 toxin, Shiga toxin, pertussis toxin, tetanus toxin, soybean Bowman-Birk protease inhibitor, Pseudomonas exotoxin, alorin, saporin, modeccin, gelanin, abrin A chain, modeccin A chain, alpha-sarcin, *Aleurites fordii* proteins, dianthin proteins, *Phytolacca americana* proteins such as PAPI, PAPII, and PAP-S, *Momordica charantia* inhibitor, curcin, crotin, *Sapaonaria officinalis* inhibitor, gelonin, mitogellin, restrictocin, phenomycin, and enomycin toxins; ribonuclease (RNase); DNase I, Staphylococcal enterotoxin A; pokeweed antiviral protein; diphtherin toxin; and Pseudomonas endotoxin.

In some embodiments, the antibodies are conjugated to a nucleic acid or nucleic acid-associated molecule. In one such embodiment, the conjugated nucleic acid is a cytotoxic ribonuclease (RNase) or deoxy-ribonuclease (e.g., DNase I), an antisense nucleic acid, an inhibitory RNA molecule (e.g., a siRNA molecule) or an immunostimulatory nucleic acid (e.g., an immunostimulatory CpG motif-containing DNA molecule). In some embodiments, the antibody is conjugated to an aptamer or a ribozyme.

In some embodiments, the antibodies are conjugated, e.g., as a fusion protein, to a lytic peptide such as CLIP, Magainin 2, mellitin, Cecropin and P18.

In some embodiments, the antibodies are conjugated to a cytokine, such as, e.g., IL-2, IL-4, IL-6, IL-7, IL-10, IL-12, IL-13, IL-15, IL-18, IL-23, IL-24, IL-27, IL-28a, IL-28b, IL-29, KGF, IFNa, IFN3, IFNy, GM-CSF, CD40L, Flt3 ligand, stem cell factor, ancestim, and TNFa.

In some embodiments, the antibodies are conjugated to a radioisotope or to a radioisotope-containing chelate. For example, the antibodies can be conjugated to a chelator linker, e.g. DOTA, DTPA or tiuxetan, which allows for the antibody to be complexed with a radioisotope. The antibodies may also or alternatively comprise or be conjugated to one or more radiolabeled amino acids or other radiolabeled moleculesNon-limiting examples of radioisotopes include $^3$H, $^{14}$C, $^{15}$N, $^{35}$S, $^{90}$Y, $^{99}$Tc, $^{125}$I, $^{131}$I, $^{186}$Re, $^{213}$Bi, $^{225}$Ac and $^{227}$Th. For therapeutic purposes, a radioisotope emitting beta- or alpha-particle radiation can be used, e.g., 1311, 90Y, 211At, 212Bi, 67Cu, 186Re, 188Re, and 212Pb.

In certain embodiments, antibodies-drug conjugate comprise an anti-tubulin agent. Examples of anti-tubulin agents include, for example, taxanes (e.g., Taxol® (paclitaxel), Taxotere® (docetaxel)), T67 (Tularik), *vinca* alkyloids (e.g., vincristine, vinblastine, vindesine, and vinorelbine), and dolastatins (e.g., auristatin E, AFP, MMAF, MMAE, AEB, AEVB). Other antitubulin agents include, for example, baccatin derivatives, taxane analogs (e.g., epothilone A and B), nocodazole, colchicine and colcimid, estramustine, cryptophysins, cemadotin, maytansinoids, combretastatins, discodermolide, and eleutherobin. In some embodiments, the cytotoxic agent is a maytansinoid, another group of anti-tubulin agents. For example, in specific embodiments, the maytansinoid is maytansine or DM-1 (ImmunoGen, Inc.; see also Chari et al., *Cancer Res.* 52:127-131, 1992).

In other embodiments, the cytotoxic agent is an antimetabolite. The antimetabolite can be, for example, a purine antagonist (e.g., azothioprine or mycophenolate mofetil), a dihydrofolate reductase inhibitor (e.g., methotrexate), acyclovir, gangcyclovir, zidovudine, vidarabine, ribavarin, azidothymidine, cytidine arabinoside, amantadine, dideoxyuridine, iododeoxyuridine, poscarnet, or trifluridine.

In other embodiments, anti-HER4 antibodies are conjugated to a pro-drug converting enzyme. The pro-drug converting enzyme can be recombinantly fused to the antibody or chemically conjugated thereto using known methods. Exemplary pro-drug converting enzymes are carboxypeptidase G2, β-glucuronidase, penicillin-V-amidase, penicillin-G-amidase, β-lactamase, β-glucosidase, nitroreductase and carboxypeptidase A.

Typically, the antibody-drug conjugate compounds comprise a linker unit between the drug unit and the antibody unit. In some embodiments, the linker is cleavable under intracellular conditions, such that cleavage of the linker releases the drug unit from the antibody in the intracellular environment. In yet other embodiments, the linker unit is not cleavable and the drug is released, for example, by antibody degradation.

In some embodiments, the linker is cleavable by a cleaving agent that is present in the intracellular environment (e.g., within a lysosome or endosome or caveolea). The linker can be, e.g., a peptidyl linker that is cleaved by an intracellular peptidase or protease enzyme, including, but not limited to, a lysosomal or endosomal protease. In some embodiments, the peptidyl linker is at least two amino acids long or at least three amino acids long. Cleaving agents can include cathepsins B and D and plasmin, all of which are known to hydrolyze dipeptide drug derivatives resulting in the release of active drug inside target cells (see, e.g., Dubowchik and Walker, 1999, Pharm. Therapeutics 83:67-123).

Most typical are peptidyl linkers that are cleavable by enzymes that are present in 191P4D12-expressing cells.

Examples of such linkers are described, e.g., in U.S. Pat. No. 6,214,345, incorporated herein by reference in its entirety and for all purposes. In a specific embodiment, the peptidyl linker cleavable by an intracellular protease is a Val-Cit linker or a Phe-Lys linker (see, e.g., U.S. Pat. No. 6,214,345, which describes the synthesis of doxorubicin with the Val-Cit linker). One advantage of using intracellular proteolytic release of the therapeutic agent is that the agent is typically attenuated when conjugated and the serum stabilities of the conjugates are typically high.

In other embodiments, the cleavable linker is pH-sensitive, i.e., sensitive to hydrolysis at certain pH values. Typically, the pH-sensitive linker hydrolyzable under acidic conditions. For example, an acid-labile linker that is hydrolyzable in the lysosome (e.g., a hydrazone, semicarbazone, thiosemicarbazone, cis-aconitic amide, orthoester, acetal, ketal, or the like) can be used. (See, e.g., U.S. Pat. Nos. 5,122,368; 5,824,805; 5,622,929; Dubowchik and Walker, 1999, Pharm. Therapeutics 83:67-123; Neville et al., 1989, Biol. Chem. 264:14653-14661.) Such linkers are relatively stable under neutral pH conditions, such as those in the blood, but are unstable at below pH 5.5 or 5.0, the approximate pH of the lysosome. In certain embodiments, the hydrolyzable linker is a thioether linker (such as, e.g., a thioether attached to the therapeutic agent via an acylhydrazone bond (see, e.g., U.S. Pat. No. 5,622,929).

In yet other embodiments, the linker is cleavable under reducing conditions (e.g., a disulfide linker). A variety of disulfide linkers are known in the art, including, for example, those that can be formed using SATA (N-succinimidyl-S-acetylthioacetate), SPDP (N-succinimidyl-3-(2-pyridyldithio)propionate), SPDB (N-succinimidyl-3-(2-pyridyldithio)butyrate) and SMPT (N-succinimidyl-oxycarbonyl-alpha-methyl-alpha-(2-pyridyl-dithio) toluene), SPDB and SMPT. (See, e.g., Thorpe et al., 1987, Cancer Res. 47:5924-5931; Wawrzynczak et al., In Immunoconjugates: Antibody Conjugates in Radioimagery and Therapy of Cancer (C. W. Vogel ed., Oxford U. Press, 1987. See also U.S. Pat. No. 4,880,935.)

In yet other specific embodiments, the linker is a malonate linker (Johnson et al., 1995, Anticancer Res. 15:1387-93), a maleimidobenzoyl linker (Lau et al., 1995, Bioorg-Med-Chem. 3(10):1299-1304), or a 3'-N-amide analog (Lau et al., 1995, Bioorg-Med-Chem. 3(10):1305-12).

In yet other embodiments, the linker unit is not cleavable and the drug is released by antibody degradation.

Typically, the linker is not substantially sensitive to the extracellular environment. As used herein, "not substantially sensitive to the extracellular environment," in the context of a linker, means that no more than about 20%, typically no more than about 15%, more typically no more than about 10%, and even more typically no more than about 5%, no more than about 3%, or no more than about 1% of the linkers, in a sample of antibody-drug conjugate compound, are cleaved when the antibody-drug conjugate compound is present in an extracellular environment (e.g., in plasma). Whether a linker is not substantially sensitive to the extracellular environment can be determined, for example, by incubating with plasma the antibody-drug conjugate compound for a predetermined time period (e.g., 2, 4, 8, 16, or 24 hours) and then quantitating the amount of free drug present in the plasma.

Techniques for conjugating molecules to antibodies, are well-known in the art (See, e.g., Arnon et al., "Monoclonal Antibodies For Immunotargeting Of Drugs In Cancer Therapy," in Monoclonal Antibodies And Cancer Therapy (Reisfeld et al. eds., Alan R. Liss, Inc., 1985); Hellstrom et al., "Antibodies For Drug Delivery," in Controlled Drug Delivery (Robinson et al. eds., Marcel Deiker, Inc., 2nd ed. 1987); Thorpe, "Antibody Carriers Of Cytotoxic Agents In Cancer Therapy: A Review," in Monoclonal Antibodies '84: Biological And Clinical Applications (Pinchera et al. eds., 1985); "Analysis, Results, and Future Prospective of the Therapeutic Use of Radiolabeled Antibody In Cancer Therapy," in Monoclonal Antibodies For Cancer Detection And Therapy (Baldwin et al. eds., Academic Press, 1985); and Thorpe et al., 1982, Immunol. Rev. 62:119-58. See also, e.g., PCT publication WO 89/12624.) Typically, the nucleic acid molecule is covalently attached to lysines or cysteines on the antibody, through N-hydroxysuccinimide ester or maleimide functionality respectively. Methods of conjugation using engineered cysteines or incorporation of unnatural amino acids have been reported to improve the homogeneity of the conjugate (Axup, J. Y., Bajjuri, K. M., Ritland, M., Hutchins, B. M., Kim, C. H., Kazane, S. A., Halder, R., Forsyth, J. S., Santidrian, A. F., Stafin, K., et al. (2012). Synthesis of site-specific antibody-drug conjugates using unnatural amino acids. Proc. Natl. Acad. Sci. USA 109, 16101-16106; Junutula, J. R., Flagella, K. M., Graham, R. A., Parsons, K. L., Ha, E., Raab, H., Bhakta, S., Nguyen, T., Dugger, D. L., Li, G., et al. (2010). Engineered thio-trastuzumab-DM1 conjugate with an improved therapeutic index to target humanepidermal growth factor receptor 2-positive breast cancer. Clin. Cancer Res. 16, 4769-4778.). Junutula et al. (2008) developed cysteine-based site-specific conjugation called "THIOMABs" (TDCs) that are claimed to display an improved therapeutic index as compared to conventional conjugation methods. Conjugation to unnatural amino acids that have been incorporated into the antibody is also being explored for ADCs; however, the generality of this approach is yet to be established (Axup et al., 2012). In particular the one skilled in the art can also envisage Fc-containing polypeptide engineered with an acyl donor glutamine-containing tag (e.g., Gin-containing peptide tags or Q-tags) or an endogenous glutamine that are made reactive by polypeptide engineering (e.g., via amino acid deletion, insertion, substitution, or mutation on the polypeptide). Then a transglutaminase, can covalently cross-link with an amine donor agent (e.g., a small molecule comprising or attached to a reactive amine) to form a stable and homogenous population of an engineered Fc-containing polypeptide conjugate with the amine donor agent being site-specifically conjugated to the Fc-containing polypeptide through the acyl donor glutamine-containing tag or the accessible/exposed/reactive endogenous glutamine (WO 2012059882).

Therapeutic Uses

Antibodies, fragments or immunoconjugates of the invention may be useful for treating any diseases associated with HER4 overexpression particularly cancers and metastatic cancers.

Thus, the invention also relates to antibodies, fragments or immunoconjugates of the invention for use in the treatment of any diseases associated with HER4 overexpression particularly cancers and metastatic cancers.

The antibodies of the invention may be used alone or in combination with any suitable agent.

In each of the embodiments of the treatment methods described herein, the anti-HER4 antibody or anti-HER4 antibody-drug conjugate is delivered in a manner consistent with conventional methodologies associated with management of the disease or disorder for which treatment is sought. In accordance with the disclosure herein, an effective amount of the antibody or antibody-drug conjugate is administered to a patient in need of such treatment for a time and under conditions sufficient to prevent or treat the disease or disorder.

As used herein, the terms "treatment" and "treat" refer to both prophylactic or preventive treatment as well as curative or disease modifying treatment, including treatment of subjects at risk of contracting the disease or suspected to have contracted the disease as well as subjects who are ill or have been diagnosed as suffering from a disease or medical condition, and includes suppression of clinical relapse. The treatment may be administered to a subject having a medical disorder or who ultimately may acquire the disorder, in order to prevent, cure, delay the onset of, reduce the severity of, or ameliorate one or more symptoms of a disorder or recurring disorder, or in order to prolong the survival of a subject beyond that expected in the absence of such treatment. By "therapeutic regimen" is meant the pattern of treatment of an illness, e.g., the pattern of dosing used during therapy. A therapeutic regimen may include an induction regimen and a maintenance regimen. The phrase "induction regimen" or "induction period" refers to a therapeutic regimen (or the portion of a therapeutic regimen) that is used for the initial treatment of a disease. The general goal of an induction regimen is to provide a high level of drug to a subject during the initial period of a treatment regimen. An induction regimen may employ (in part or in whole) a "loading regimen", which may include administering a greater dose of the drug than a physician would employ during a maintenance regimen, administering a drug more frequently than a physician would administer the drug during a maintenance regimen, or both. The phrase "maintenance regimen" or "maintenance period" refers to a therapeutic regimen (or the portion of a therapeutic regimen) that is used for the maintenance of a subject during treatment of an illness, e.g., to keep the subject in remission for long periods of time (months or years). A maintenance regimen may employ continuous therapy (e.g., administering a drug at a regular intervals, e.g., weekly, monthly, yearly, etc.) or intermittent therapy (e.g., interrupted treatment, intermittent treatment, treatment at relapse, or treatment upon achievement of a particular predetermined criteria [e.g., disease manifestation, etc.]).

As used herein, the term "therapeutically effective amount" or "effective amount" refers to an amount effective, at dosages and for periods of time necessary, to achieve a desired therapeutic result. A therapeutically effective amount of the antibodies of the present invention may vary according to factors such as the disease state, age, sex, and weight of the individual, and the ability of the antibodies of the present invention to elicit a desired response in the individual. A therapeutically effective amount is also one in which any toxic or detrimental effects of the antibodies or antibodies portion are outweighed by the therapeutically beneficial effects. The efficient dosages and dosage regimens for the antibodies of the present invention depend on the disease or condition to be treated and may be determined by the persons skilled in the art. A physician having ordinary skill in the art may readily determine and prescribe the effective amount of the pharmaceutical composition required. For example, the physician could start doses of the antibodies of the present invention employed in the pharmaceutical composition at levels lower than that required in order to achieve the desired therapeutic effect and gradually increase the dosage until the desired effect is achieved. In general, a suitable dose of a composition of the present invention will be that amount of the compound which is the lowest dose effective to produce a therapeutic effect according to a particular dosage regimen. Such an effective dose will generally depend upon the factors described above. For example, a therapeutically effective amount for therapeutic use may be measured by its ability to stabilize the progression of disease. Typically, the ability of a compound to inhibit cancer may, for example, be evaluated in an animal model system predictive of efficacy in human tumors. Alternatively, this property of a composition may be evaluated by examining the ability of the compound to induce cytotoxicity by in vitro assays known to the skilled practitioner. A therapeutically effective amount of a therapeutic compound may decrease tumor size, or otherwise ameliorate symptoms in a subject. One of ordinary skill in the art would be able to determine such amounts based on such factors as the subject's size, the severity of the subject's symptoms, and the particular composition or route of administration selected. An exemplary, non-limiting range for a therapeutically effective amount of an antibody of the present invention is about 0.1-100 mg/kg, such as about 0.1-50 mg/kg, for example about 0.1-20 mg/kg, such as about 0.1-10 mg/kg, for instance about 0.5, about such as 0.3, about 1, about 3 mg/kg, about 5 mg/kg or about 8 mg/kg. An exemplary, non-limiting range for a therapeutically effective amount of an antibody of the present invention is 0.02-100 mg/kg, such as about 0.02-30 mg/kg, such as about 0.05-10 mg/kg or 0.1-3 mg/kg, for example about 0.5-2 mg/kg. Administration may e.g. be intravenous, intramuscular, intraperitoneal, or subcutaneous, and for instance administered proximal to the site of the target. Dosage regimens in the above methods of treatment and uses are adjusted to provide the optimum desired response (e.g., a therapeutic response). For example, a single bolus may be administered, several divided doses may be administered over time or the dose may be proportionally reduced or increased as indicated by the exigencies of the therapeutic situation. In some embodiments, the efficacy of the treatment is monitored during the therapy, e.g. at predefined points in time. In some embodiments, the efficacy may be monitored by visualization of the disease area, or by other diagnostic methods described further herein, e.g. by performing one or more PET-CT scans, for example using labeled antibodies of the present invention, fragment or mini-antibodies derived from the antibodies of the present invention. If desired, an effective daily dose of a pharmaceutical composition may be administered as two, three, four, five, six or more sub-doses administered separately at appropriate intervals throughout the day, optionally, in unit dosage forms. In some embodiments, the monoclonal antibodies of the present invention are administered by slow continuous infusion over a long period, such as more than 24 hours, in order to minimize any unwanted side effects. An effective dose of antibodies of the present invention may also be administered using a weekly, biweekly or triweekly dosing period. The dosing period may be restricted to, e.g., 8 weeks, 12 weeks or until clinical progression has been established. As non-limiting examples, treatment according to the present invention may be provided as a daily dosage of antibodies of the present invention in an amount of about 0.1-100 mg/kg, such as 0.2, 0.5, 0.9, 1.0, 1.1, 1.5, 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 45, 50, 60, 70, 80, 90 or 100 mg/kg, per day, on at least one of days 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40, or alternatively, at least one of weeks 1, 2, 3, 4, 5, 6, 7, 8, 9, 10, 11, 12, 13, 14, 15, 16, 17, 18, 19 or 20 after initiation of treatment, or any combination thereof, using single or divided doses every 24, 12, 8, 6, 4, or 2 hours, or any combination thereof.

Accordingly, one object of the present invention relates to a method of treating cancers and metastatic cancers in a subject in need thereof comprising administering to the subject a therapeutically effective amount of the antibodies of the present invention.

In another aspect, the present invention relates to the antibodies of the present invention, as defined in any aspect or embodiment herein, for use as a medicament.

In some embodiments, the subject suffers from a cancer. Accordingly, a further object of the present invention relates to a method of treating a cancer in a subject in need thereof comprising administering to the subject a therapeutically effective amount of the antibodies of the present invention.

As used herein, the term "cancer" has its general meaning in the art and includes, but is not limited to, solid tumors and blood borne tumors The term cancer includes diseases of the skin, tissues, organs, bone, cartilage, blood and vessels. The term "cancer" further encompasses both primary and metastatic cancers. Examples of cancers that may treated by methods and compositions of the invention include, but are not limited to, cancer cells from the bladder, blood, bone, bone marrow, brain, breast, colon, esophagus, gastrointestinal, gum, head, kidney, liver, lung, nasopharynx, neck, ovary, prostate, skin, stomach, testis, tongue, or uterus. In addition, the cancer may specifically be of the following histological type, though it is not limited to these: neoplasm, malignant; carcinoma; carcinoma, undifferentiated; giant and spindle cell carcinoma; small cell carcinoma; papillary carcinoma; squamous cell carcinoma; lymphoepithelial carcinoma; basal cell carcinoma; pilomatrix carcinoma; transitional cell carcinoma; papillary transitional cell carcinoma; adenocarcinoma; gastrinoma, malignant; cholangiocarcinoma; hepatocellular carcinoma; combined hepatocellular carcinoma and cholangiocarcinoma; trabecular adenocarcinoma; adenoid cystic carcinoma; adenocarcinoma in adenomatous polyp; adenocarcinoma, familial polyposis coli; solid carcinoma; carcinoid tumor, malignant; branchioloalveolar adenocarcinoma; papillary adenocarcinoma; chromophobe carcinoma; acidophil carcinoma; oxyphilic adenocarcinoma; basophil carcinoma; clear cell adenocarcinoma; granular cell carcinoma; follicular adenocarcinoma; papillary and follicular adenocarcinoma; nonencapsulating sclerosing carcinoma; adrenal cortical carcinoma; endometroid carcinoma; skin appendage carcinoma; apocrine adenocarcinoma; sebaceous adenocarcinoma; ceruminous; adenocarcinoma; mucoepidermoid carcinoma; cystadenocarcinoma; papillary cystadenocarcinoma; papillary serous cystadenocarcinoma; mucinous cystadenocarcinoma; mucinous adenocarcinoma; signet ring cell carcinoma; infiltrating duct carcinoma; medullary carcinoma; lobular carcinoma; inflammatory carcinoma; paget's disease, mammary; acinar cell carcinoma; adenosquamous carcinoma; adenocarcinoma w/squamous metaplasia; thymoma, malignant; ovarian stromal tumor, malignant; thecoma, malignant; granulosa cell tumor, malignant; and roblastoma, malignant; Sertoli cell carcinoma; leydig cell tumor, malignant; lipid cell tumor, malignant; paraganglioma, malignant; extramammary paraganglioma, malignant; pheochromocytoma; glomangiosarcoma; malignant melanoma; amelanotic melanoma; superficial spreading melanoma; malign melanoma in giant pigmented nevus; epithelioid cell melanoma; blue nevus, malignant; sarcoma; fibrosarcoma; fibrous histiocytoma, malignant; myxosarcoma; liposarcoma; leiomyosarcoma; rhabdomyosarcoma; embryonal rhabdomyosarcoma;

alveolar rhabdomyosarcoma; stromal sarcoma; mixed tumor, malignant; mullerian mixed tumor; nephroblastoma; hepatoblastoma; carcinosarcoma; mesenchymoma, malignant; brenner tumor, malignant; phyllodes tumor, malignant; synovial sarcoma; mesothelioma, malignant; dysgerminoma; embryonal carcinoma; teratoma, malignant; struma ovarii, malignant; choriocarcinoma; mesonephroma, malignant; hemangiosarcoma; hemangioendothelioma, malignant; kaposi's sarcoma; hemangiopericytoma, malignant; lymphangiosarcoma; osteosarcoma; juxtacortical osteosarcoma; chondrosarcoma; chondroblastoma, malignant; mesenchymal chondrosarcoma; giant cell tumor of bone; ewing's sarcoma; odontogenic tumor, malignant; ameloblastic odontosarcoma; ameloblastoma, malignant; ameloblastic fibrosarcoma; pinealoma, malignant; chordoma; glioma, malignant; ependymoma; astrocytoma; protoplasmic astrocytoma; fibrillary astrocytoma; astroblastoma; glioblastoma; medulloblastoma; Ewing sarcoma; cervical cancer, oligodendroglioma; oligodendroblastoma; primitive neuroectodermal; cerebellar sarcoma; ganglioneuroblastoma; neuroblastoma; retinoblastoma; olfactory neurogenic tumor; meningioma, malignant; neurofibrosarcoma; neurilemmoma, malignant; granular cell tumor, malignant; malignant lymphoma; Hodgkin's disease; Hodgkin's lymphoma; paragranuloma; malignant lymphoma, small lymphocytic; malignant lymphoma, large cell, diffuse; malignant lymphoma, follicular; mycosis fungoides; other specified non-Hodgkin's lymphomas; malignant histiocytosis; multiple myeloma; mast cell sarcoma; immunoproliferative small intestinal disease; leukemia; lymphoid leukemia; plasma cell leukemia; erythroleukemia; lymphosarcoma cell leukemia; myeloid leukemia; basophilic leukemia; eosinophilic leukemia; monocytic leukemia; mast cell leukemia; megakaryoblastic leukemia; myeloid sarcoma; and hairy cell leukemia.

More particularly, the invention is suitable to treat medulloblastoma, Ewing sarcoma, cervical, breast, ovarian, lung, urothelial and pancreatic cancers. In one embodiment, the breast cancer is a triple negative breast cancer.

In some embodiment, the anti-HER4 antibodies of the present invention are used in combination.

In some embodiment, the C6 mAb of the present invention and the D5 mAb of the present invention are used in combination. In some embodiment, the C6 mAb of the present invention and the F4 mAb of the present invention are used in combination. In some embodiment, the C6 mAb of the present invention and the H2 mAb of the present invention are used in combination. In some embodiment, the D5 mAb of the present invention and the H2 mAb of the present invention are used in combination. In some embodiment, the F4 mAb of the present invention and the H2 mAb of the present invention are used in combination. In some embodiment, the F4 mAb of the present invention and the D5 mAb of the present invention are used in combination.

In certain embodiments, anti-HER4 antibodies or antibodies-drug conjugates are used in combination with a second agent for treatment of a disease or disorder. When used for treating cancer, anti-HER4 antibodies or antibodies-drug conjugates of the invention may be used in combination with conventional cancer therapies such as, e.g., surgery, radiotherapy, chemotherapy, or combinations thereof.

The present invention also provides for therapeutic applications where antibodies of the present invention is used in combination with at least one further therapeutic agent, e.g. for treating cancers and metastatic cancers. Such administration may be simultaneous, separate or sequential. For simultaneous administration the agents may be administered as one composition or as separate compositions, as appropriate. The further therapeutic agent is typically relevant for the disorder to be treated. Exemplary therapeutic agents include other anti-cancer antibodies, cytotoxic agents, chemotherapeutic agents, anti-angiogenic agents, anti-cancer immunogens, cell cycle control/apoptosis regulating agents, hormonal regulating agents, and other agents described below.

In some embodiments, the antibodies of the present invention is used in combination with a chemotherapeutic agent. The term "chemotherapeutic agent" refers to chemical compounds that are effective in inhibiting tumor growth. Examples of chemotherapeutic agents include alkylating agents such as thiotepa and cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaorarnide and trimethylolomelamine; acetogenins (especially bullatacin and bullatacinone); a carnptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CBI-TMI); eleutherobin; pancratistatin; a sarcodictyin; spongistatin; nitrogen mustards such as chlorambucil, chlornaphazine, cholophosphamide, estrarnustine, ifosfamide, mechlorethamine, mechlorethamine oxide hydrochloride, melphalan, novembichin, phenesterine, prednimus tine, trofosfamide, uracil mustard; nitrosureas such as carmustine, chlorozotocin, fotemustine, lomustine, nimustine, ranimustine; antibiotics such as the enediyne antibiotics (e.g. calicheamicin, especially calicheamicin (11 and calicheamicin 211, see, e.g., Agnew Chem Intl. Ed. Engl. 33:183-186 (1994); dynemicin, including dynemicin A; an esperamicin; as well as neocarzinostatin chromophore and related chromoprotein enediyne antiobiotic chromomophores), aclacinomysins, actinomycin, authramycin, azaserine, bleomycins, cactinomycin, carabicin, canninomycin, carzinophilin, chromomycins, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin and deoxydoxorubicin), epirubicin, esorubicin, idanrbicin, marcellomycin, mitomycins, mycophenolic acid, nogalarnycin, olivomycins, peplomycin, potfiromycin, puromycin, quelamycin, rodorubicin, streptomgrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, 5-FU; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophospharnide glycoside; aminolevulinic acid; amsacrine; bestrabucil; bisantrene; edatraxate; defofamine; demecolcine; diaziquone; elfornithine; elliptinium acetate; an epothilone; etoglucid; gallium nitrate; hydroxyurea; lentinan; lonidamine; maytansinoids such as maytansine and ansamitocins; mitoguazone; mitoxantrone; mopidamol; nitracrine; pento statin; phenamet; pirarubicin; podophyllinic acid; 2-ethylhydrazide; procarbazine; PSK®; razoxane; rhizoxin; sizofiran; spirogennanium; tenuazonic acid; triaziquone; 2,2', 2"-trichlorotriethylarnine; trichothecenes (especially T-2 toxin, verracurin A, roridinA and anguidine); urethan; vindesine; dacarbazine; mannomustine; mitobromtol; mitolactol; pipobroman; gacytosine; arabinoside ("Ara-C"); cyclophosphamide; thiotepa; taxoids, e.g. paclitaxel (TAXOL®, Bristol-Myers Squibb Oncology, Princeton, N.J.) and doxetaxel (TAXOTERE®, Rhone-Poulenc Rorer, Antony, France); chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; CPT-1 1; topoisomerase inhibitor RFS 2000; difluoromethylornithine (DMFO); retinoic acid; capecitabine; and phannaceutically acceptable salts, acids or derivatives of any of the above. Also included in this definition are antihormonal agents that act to regulate or inhibit honnone action on tumors such as anti-estrogens including for example tamoxifen, raloxifene, aromatase inhibiting 4(5)-imidazoles, 4-hydroxytamoxifen, trioxifene, keoxifene, LY117018, onapristone, and toremifene (Fareston); and anti-androgens such as flutamide, nilutamide, bicalutamide, leuprolide, and goserelin; and phannaceutically acceptable salts, acids or derivatives of any of the above.

In some embodiments, the antibodies of the present invention are used in combination with a targeted cancer therapy. Targeted cancer therapies are drugs or other substances that block the growth and spread of cancer by interfering with specific molecules ("molecular targets") that are involved in the growth, progression, and spread of cancer. Targeted cancer therapies are sometimes called "molecularly targeted drugs," "molecularly targeted therapies," "precision medicines," or similar names. In some embodiments, the targeted therapy consists of administering the subject with a tyrosine kinase inhibitor. The term "tyrosine kinase inhibitor" refers to any of a variety of therapeutic agents or drugs that act as selective or non-selective inhibitors of receptor and/or non-receptor tyrosine kinases. Tyrosine kinase inhibitors and related compounds are well known in the art and described in U.S Patent Publication 2007/0254295, which is incorporated by reference herein in its entirety. It will be appreciated by one of skill in the art that a compound related to a tyrosine kinase inhibitor will recapitulate the effect of the tyrosine kinase inhibitor, e.g., the related compound will act on a different member of the tyrosine kinase signaling pathway to produce the same effect as would a tyrosine kinase inhibitor of that tyrosine kinase. Examples of tyrosine kinase inhibitors and related compounds suitable for use in methods of embodiments of the present invention include, but are not limited to, dasatinib (BMS-354825), PP2, BEZ235, saracatinib, gefitinib (Iressa), sunitinib (Sutent; SU11248), erlotinib (Tarceva; OSI-1774), lapatinib (GW572016; GW2016), canertinib (CI 1033), semaxinib (SU5416), vatalanib (PTK787/ZK222584), sorafenib (BAY 43-9006), imatinib (Gleevec; STI571), leflunomide (SU101), vandetanib (Zactima; ZD6474), MK-2206 (8-[4-aminocyclobutyl)phenyl]-9-phenyl-1,2,4-triazolo[3,4-f][1,6]naphthyridin-3(2H)-one hydrochloride) derivatives thereof, analogs thereof, and combinations thereof. Additional tyrosine kinase inhibitors and related compounds suitable for use in the present invention are described in, for example, U.S Patent Publication 2007/0254295, U.S. Pat. Nos. 5,618,829, 5,639,757, 5,728,868, 5,804,396, 6,100,254, 6,127,374, 6,245,759, 6,306,874, 6,313,138, 6,316,444, 6,329,380, 6,344,459, 6,420,382, 6,479,512, 6,498,165, 6,544,988, 6,562,818, 6,586,423, 6,586,424, 6,740,665, 6,794,393, 6,875,767, 6,927,293, and 6,958,340, all of which are incorporated by reference herein in their entirety. In some embodiments, the tyrosine kinase inhibitor is a small molecule kinase inhibitor that has been orally administered and that has been the subject of at least one Phase I clinical trial, more preferably at least one Phase II clinical, even more preferably at least one Phase III clinical trial, and most preferably approved by the FDA for at least one hematological or oncological indication. Examples of such inhibitors include, but are not limited to, Gefitinib, Erlotinib, Lapatinib, Canertinib, BMS-599626 (AC-480), Neratinib, KRN-633, CEP-11981, Imatinib, Nilotinib, Dasatinib, AZM-475271, CP-724714, TAK-165, Sunitinib, Vatalanib, CP-547632, Vandetanib, Bosutinib, Lestaurtinib, Tandutinib, Midostaurin, Enzastaurin, AEE-788, Pazopanib, Axitinib, Motasenib, OSI-930, Cediranib, KRN-951, Dovitinib, Seliciclib, SNS-032, PD-0332991, MKC-I (Ro-317453; R-440), Sorafenib, ABT-869, Brivanib (BMS-582664), SU-14813, Telatinib, SU-6668, (TSU-68), L-21649, MLN-8054, AEW-541, and PD-0325901.

In some embodiments, the antibodies of the present invention are used in combination with an immunotherapeutic agent. The term "immunotherapeutic agent," as used herein, refers to a compound, composition or treatment that indirectly or directly enhances, stimulates or increases the body's immune response against cancer cells and/or that decreases the side effects of other anticancer therapies. Immunotherapy is thus a therapy that directly or indirectly stimulates or enhances the immune system's responses to cancer cells and/or lessens the side effects that may have been caused by other anti-cancer agents. Immunotherapy is also referred to in the art as immunologic therapy, biological therapy biological response modifier therapy and biotherapy. Examples of common immunotherapeutic agents known in the art include, but are not limited to, cytokines, cancer vaccines, monoclonal antibodies and non-cytokine adjuvants. Alternatively the immunotherapeutic treatment may consist of administering the subject with an amount of immune cells (T cells, NK, cells, dendritic cells, B cells . . . ). Immunotherapeutic agents can be non-specific, i.e. boost the immune system generally so that the human body becomes more effective in fighting the growth and/or spread of cancer cells, or they can be specific, i.e. targeted to the cancer cells themselves immunotherapy regimens may combine the use of non-specific and specific immunotherapeutic agents. Non-specific immunotherapeutic agents are substances that stimulate or indirectly improve the immune system. Non-specific immunotherapeutic agents have been used alone as a main therapy for the treatment of cancer, as well as in addition to a main therapy, in which case the non-specific immunotherapeutic agent functions as an adjuvant to enhance the effectiveness of other therapies (e.g. cancer vaccines). Non-specific immunotherapeutic agents can also function in this latter context to reduce the side effects of other therapies, for example, bone marrow suppression induced by certain chemotherapeutic agents. Non-specific immunotherapeutic agents can act on key immune system cells and cause secondary responses, such as increased production of cytokines and immunoglobulins. Alternatively, the agents can themselves comprise cytokines. Non-specific immunotherapeutic agents are generally classified as cytokines or non-cytokine adjuvants. A number of cytokines have found application in the treatment of cancer either as general non-specific immunotherapies designed to boost the immune system, or as adjuvants provided with other therapies. Suitable cytokines include, but are not limited to, interferons, interleukins and colony-stimulating factors. Interferons (IFNs) contemplated by the present invention include the common types of IFNs, IFN-alpha (IFN-α), IFN-beta (IFN-β) and IFN-gamma (IFN-γ). IFNs can act directly on cancer cells, for example, by slowing their growth, promoting their development into cells with more normal behavior and/or increasing their production of antigens thus making the cancer cells easier for the immune system to recognise and destroy. IFNs can also act indirectly on cancer cells, for example, by slowing down angiogenesis, boosting the immune system and/or stimulating natural killer (NK) cells, T cells and macrophages. Recombinant IFN-alpha is available commercially as Roferon (Roche Pharmaceuticals) and Intron A (Schering Corporation). Interleukins contemplated by the present invention include IL-2, IL-4, IL-11 and IL-12. Examples of commercially available recombinant interleukins include Proleukin® (IL-2; Chiron Corporation) and Neumega® (IL-12; Wyeth Pharmaceuticals). Zymogenetics, Inc. (Seattle, Wash.) is currently testing a recombinant form of IL-21, which is also contemplated for use in the combinations of the present invention. Colony-stimulating factors (CSFs) contemplated by the present invention include granulocyte colony stimulating factor (G-CSF or filgrastim), granulocyte-macrophage colony stimulating factor (GM-CSF or sargramostim) and erythropoietin (epoetin alfa, darbepoietin). Treatment with one or more growth factors can help to stimulate the generation of new blood cells in subjects undergoing traditional chemotherapy. Accordingly, treatment with CSFs can be helpful in decreasing the side effects associated with chemotherapy and can allow for higher doses of chemotherapeutic agents to be used. Various-recombinant colony stimulating factors are available commercially, for example, Neupogen® (G-CSF; Amgen), Neulasta (pelfilgrastim; Amgen), Leukine (GM-CSF; Berlex), Procrit (erythropoietin; Ortho Biotech), Epogen (erythropoietin; Amgen), Arnesp (erytropoietin). Combination compositions and combination administration methods of the present invention may also involve "whole cell" and "adoptive" immunotherapy methods. For instance, such methods may comprise infusion or re-infusion of immune system cells (for instance tumor-infiltrating lymphocytes (TILs), such as CC2+ and/or CD8+ T cells (for instance T cells expanded with tumor-specific antigens and/or genetic enhancements), antibody-expressing B cells or other antibody-producing or -presenting cells, dendritic cells (e.g., dendritic cells cultured with a DC-expanding agent such as GM-CSF and/or Flt3-L, and/or tumor-associated antigen-loaded dendritic cells), anti-tumor NK cells, so-called hybrid cells, or combinations thereof. Cell lysates may also be useful in such methods and compositions. Cellular "vaccines" in clinical trials that may be useful in such aspects include Canvaxin™, APC-8015 (Dendreon), HSPPC-96 (Antigenics), and Melacine® cell lysates. Antigens shed from cancer cells, and mixtures thereof (see for instance Bystryn et al., Clinical Cancer Research Vol. 7, 1882-1887, July 2001), optionally admixed with adjuvants such as alum, may also be components in such methods and combination compositions. In some embodiments, the antibodies of the present invention are used in combination with radiotherapy. Radiotherapy may comprise radiation or associated administration of radiopharmaceuticals to a patient. The source of radiation may be either external or internal to the patient being treated (radiation treatment may, for example, be in the form of external beam radiation therapy (EBRT) or brachytherapy (BT)). Radioactive elements that may be used in practicing such methods include, e.g., radium, cesium- 137, iridium-192, americium-241, gold-198, cobalt-57, copper-67, technetium-99, iodide-123, iodide-131, and indium-111.

In some embodiments, the antibodies of the present invention are used in combination with the Neuregulin-1 beta (NRG1β1). NRG1β1 refers to a cell adhesion molecule. Accordingly, a further object of the present invention relates to a method of treating a cancer in a subject in need there of comprising administering to the subject a therapeutically effective amount of the antibodies of the present invention and of NRG1β1.

In some embodiments, the antibodies of the present invention are used in combination with an antibody that is specific for a costimulatory molecule. Examples of antibodies that are specific for a costimulatory molecule include but are not limited to anti-CTLA4 antibodies (e.g. Ipilimumab), anti-PD1 antibodies, anti-PDL1 antibodies, anti-TIMP3 antibodies, anti-LAG3 antibodies, anti-B7H3 antibodies, anti-B7H4 antibodies or anti-B7H6 antibodies.

In some embodiments, the second agent is an agent that induces, via ADCC, the death a cell expressing an antigen to which the second agent binds. In some embodiments, the agent is an antibody (e.g. of IgG1 or IgG3 isotype) whose mode of action involves induction of ADCC toward a cell to which the antibody binds. NK cells have an important role in inducing ADCC and increased reactivity of NK cells can be directed to target cells through use of such a second agent. In some embodiments, the second agent is an antibody specific for a cell surface antigens, e.g., membrane antigens. In some embodiments, the second antibody is specific for a tumor antigen as described above (e.g., molecules specifically expressed by tumor cells), such as CD20, CD52, ErbB2 (or HER2/Neu), CD33, CD22, CD25, MUC-1, CEA, KDR, αVβ3, etc., particularly lymphoma antigens (e.g., CD20). Accordingly, the present invention also provides methods to enhance the anti-tumor effect of monoclonal antibodies directed against tumor antigen(s). In the methods of the invention, ADCC function is specifically augmented, which in turn enhances target cell killing, by sequential administration of an antibody directed against one or more tumor antigens, and an antibody of the present invention.

Accordingly, a further object relates to a method of enhancing NK cell antibody-dependent cellular cytotoxicity (ADCC) of an antibody in a subject in need thereof comprising administering to the subject the antibody, and administering to the subject antibodies of the present invention.

A further object of the present invention relates to a method of treating cancer in a subject in need thereof comprising administering to the subject a first antibody selective for a cancer cell antigen, and administering to the subject antibodies of the present invention.

A number of antibodies are currently in clinical use for the treatment of cancer, and others are in varying stages of clinical development. Antibodies of interest for the methods of the invention act through ADCC, and are typically selective for tumor cells, although one of skill in the art will recognize that some clinically useful antibodies do act on non-tumor cells, e.g. CD20. There are a number of antigens and corresponding monoclonal antibodies for the treatment of B cell malignancies. One popular target antigen is CD20, which is found on B cell malignancies. Rituximab is a chimeric unconjugated monoclonal antibody directed at the CD20 antigen. CD20 has an important functional role in B cell activation, proliferation, and differentiation. The CD52 antigen is targeted by the monoclonal antibody alemtuzumab, which is indicated for treatment of chronic lymphocytic leukemia. CD22 is targeted by a number of antibodies, and has recently demonstrated efficacy combined with toxin in chemotherapy-resistant hairy cell leukemia. Monoclonal antibodies targeting CD20, also include tositumomab and ibritumomab. Monoclonal antibodies useful in the methods of the invention, which have been used in solid tumors, include without limitation edrecolomab and trastuzumab (herceptin). Edrecolomab targets the 17-1 A antigen seen in colon and rectal cancer, and has been approved for use in Europe for these indications. Its antitumor effects are mediated through ADCC, CDC, and the induction of an anti-idiotypic network. Trastuzumab targets the HER-2/neu antigen. This antigen is seen on 25% to 35% of breast cancers. Trastuzumab is thought to work in a variety of ways: downregulation of HER-2 receptor expression, inhibition of proliferation of human tumor cells that overexpress HER-2 protein, enhancing immune recruitment and ADCC against tumor cells that overexpress HER-2 protein, and downregulation of angiogenesis factors. Alemtuzumab (Campath) is used in the treatment of chronic lymphocytic leukemia; colon cancer and lung cancer; Gemtuzumab (Mylotarg) finds use in the treatment of acute myelogenous leukemia; Ibritumomab (Zevalin) finds use in the treatment of non-Hodgkin's lymphoma; Panitumumab (Vectibix) finds use in the treatment of colon cancer. Cetuximab (Erbitux) is also of interest for use in the methods of the invention. The antibody binds to the EGF receptor (EGFR), and has been used in the treatment of solid tumors including colon cancer and squamous cell carcinoma of the head and neck (SCCHN).

In another embodiment, the antibodies of the invention promote the cleavage of the 4ICD of the isoform JMaCYT1 but not isoform JMaCYT2. Accordingly, a further object of the invention relates to the use of the antibodies which promote the cleavage of the 4ICD of the isoform JMaCYT1 or isoform JMaCYT2 in the treatment of cancer.

Diagnostic Uses

A further aspect of the invention relates to the HER4 antibodies of the invention for diagnosing and/or monitoring and/or staging a cancer and particularly a cancer in which HER4 is overexpressed.

According to the invention, a cancer in which HER4 is overexpressed denotes a cancer with a level of HER4 at the surface of the cancerous cells superior to the level of HER4 expressed by normal cells (non tumoral cells).

According to the invention, cancers in which HER4 is overexpression are modified can be breast, ovarian, lung, urothelial and pancreatic cancers.

In a preferred embodiment, antibodies of the invention may be labelled with a detectable molecule or substance, such as a fluorescent molecule, a radioactive molecule or any others labels known in the art as above described. For example, antibodies of the invention may be labelled with a radioactive molecule by any method known to the art. For example radioactive molecules include but are not limited radioactive atom for scintigraphic studies such as I123, I124, In111, Re186, Re188. Antibodies of the invention may be also labelled with a spin label for nuclear magnetic resonance (NMR) imaging (also known as magnetic resonance imaging, MRI), such as iodine-123, iodine-131, indium-111, fluorine-19, carbon-13, nitrogen-15, oxygen-17, gadolinium, manganese or iron. Following administration of the antibody, the distribution of the antibody within the patient is detected. Methods for detecting distribution of any specific label are known to those skilled in the art and any appropriate method can be used. Some non-limiting examples include, computed tomography (CT), position emission tomography (PET), magnetic resonance imaging (MRI), fluorescence, chemiluminescence and sonography.

Typically, said diagnostic methods involve the use of a biological sample obtained from the patient. As used herein the term "biological sample" encompasses a variety of sample types obtained from a subject and can be used in a diagnostic or monitoring assay. Biological samples include but are not limited to blood and other liquid samples of biological origin, solid tissue samples such as a biopsy specimen or tissue cultures or cells derived therefrom, and the progeny thereof. For example, biological samples include cells obtained from a tissue sample collected from an individual suspected of having a cancer associated with HER4 overexpression, and in a preferred embodiment from breast, ovarian, lung, urothelial and pancreatic cancers.

Therefore, biological samples encompass clinical samples, cancer samples, cells in culture, cell supernatants, cell lysates, serum, plasma, biological fluid, and tissue samples.

Pharmaceutical Compositions

Typically, the antibodies of the present invention are administered to the subject in the form of a pharmaceutical composition which comprises a pharmaceutically acceptable carrier. Pharmaceutically acceptable carriers that may be used in these compositions include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. For use in administration to a patient, the composition will be formulated for administration to the patient. The compositions of the present invention may be administered orally, parenterally, by inhalation spray, topically, rectally, nasally, buccally, vaginally or via an implanted reservoir. The used herein includes subcutaneous, intravenous, intramuscular, intraarticular, intra-synovial, intrasternal, intrathecal, intrahepatic, intralesional and intracranial injection or infusion techniques. Sterile injectable forms of the compositions of this invention may be aqueous or an oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation. The compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include, e.g., lactose. When aqueous suspensions are required for oral use, the active ingredient is combined with emulsifying and suspending agents. If desired, certain sweetening, flavoring or coloring agents may also be added. Alternatively, the compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols. The compositions of this invention may also be administered topically, especially when the target of treatment includes areas or organs readily accessible by topical application, including diseases of the eye, the skin, or the lower intestinal tract. Suitable topical formulations are readily prepared for each of these areas or organs. For topical applications, the compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water. Topical application for the lower intestinal tract can be effected in a rectal suppository formulation (see above) or in a suitable enema formulation. Patches may also be used. The compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents. For example, antibodies present in a pharmaceutical composition of this invention can be supplied at a concentration of 10 mg/mL in either 100 mg (10 mL) or 500 mg (50 mL) single-use vials. The product is formulated for IV administration in 9.0 mg/mL sodium chloride, 7.35 mg/mL sodium citrate dihydrate, 0.7 mg/mL polysorbate 80, and Sterile Water for Injection. The pH is adjusted to 6.5. An exemplary suitable dosage range for an antibody in a pharmaceutical composition of this invention may between about 1 mg/m$^2$ and 500 mg/m$^2$. However, it will be appreciated that these schedules are exemplary and that an optimal schedule and regimen can be adapted taking into account the affinity and tolerability of the particular antibody in the pharmaceutical composition that must be determined in clinical trials. A pharmaceutical composition of the invention for injection (e.g., intramuscular, i.v.) could be prepared to contain sterile buffered water (e.g. 1 ml for intramuscular), and between about 1 ng to about 100 mg, e.g. about 50 ng to about 30 mg or more preferably, about 5 mg to about 25 mg, of an anti-myosin 18A antibodies of the invention.

In certain embodiments, the use of liposomes and/or nanoparticles is contemplated for the introduction of antibodies into host cells. The formation and use of liposomes and/or nanoparticles are known to those of skill in the art.

Nanocapsules can generally entrap compounds in a stable and reproducible way. To avoid side effects due to intracellular polymeric overloading, such ultrafine particles (sized around 0.1 μm) are generally designed using polymers able to be degraded in vivo. Biodegradable polyalkyl-cyanoacrylate nanoparticles that meet these requirements are contemplated for use in the present invention, and such particles may be are easily made.

Liposomes are formed from phospholipids that are dispersed in an aqueous medium and spontaneously form multilamellar concentric bilayer vesicles (also termed multilamellar vesicles (MLVs)). MLVs generally have diameters of from 25 nm to 4 μm. Sonication of MLVs results in the formation of small unilamellar vesicles (SUVs) with diameters in the range of 200 to 500 Å, containing an aqueous solution in the core. The physical characteristics of liposomes depend on pH, ionic strength and the presence of divalent cations.

Kits

Finally, the invention also provides kits comprising at least one antibody of the invention. Kits containing antibodies of the invention find use in detecting anti-HER4 expression (increase or decrease), or in therapeutic or diagnostic assays. Kits of the invention can contain antibodies coupled to a solid support, e.g., a tissue culture plate or beads (e.g., sepharose beads). Kits can be provided which contain antibodies for detection and quantification of anti-HER4 in vitro, e.g. in an ELISA or a Western blot. Such antibodies useful for detection may be provided with a label such as a fluorescent or radiolabel.

The invention will be further illustrated by the following figures and examples. However, these examples and figures should not be interpreted in any way as limiting the scope of the present invention.

FIGURES

Figure 1:
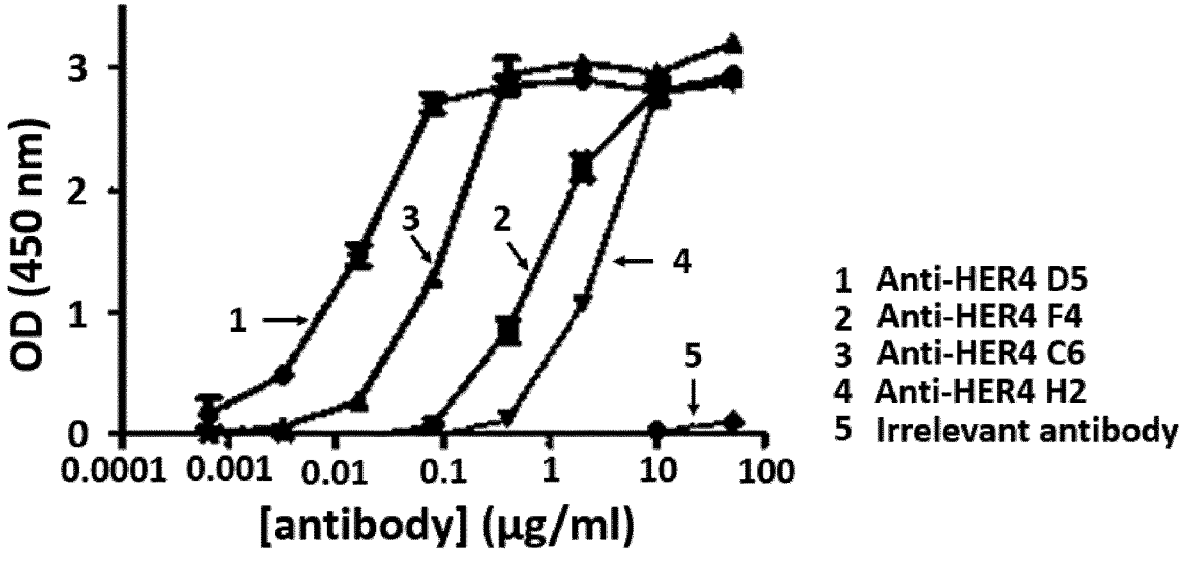
FIG. 1 shows ELISA binding of ten-fold dilutions of antibodies on human HER4.

FIG. 3. Agonist Ab C6 reduces in vivo tumor growth of human epidermal growth factor receptor 4 (HER4)+ ovarian cancer and triple negative breast cancer (TNBC) cells. Nude mice (n=10/condition) were xenografted with COV434 ovarian cancer cells (A, upper panels), C-33A cervical cancer cells (B), or HCC1187 TNBC cells (C). When tumors reached a volume of 150 mm3, mice were treated by i.p. injection of 20 mg/kg D5 (open white circles) and C6 (open white triangles) (anti-HER4 Abs), or irrelevant control Ab (Ctrl, solid black squares), twice per week for 4 wk. Carboplatin (CarboP, solid black triangles; positive control) was used at 60 mg/kg, once per week for 4 wk. Tumor growth data are presented as the mean tumor volume±SEM for each group (left panels). The tumor size of each individual mouse is indicated at the end of treatment (right panel). n.s., non-significant. For each condition, formalin-fixed, paraffinembedded (FFPE) tissue sections prepared from 5 extracted xenografts were stained independently and representative staining are shown.

(A, bottom panel) For each treatment, cleaved caspase 3 intensity was quantified with Image Scope in the whole stained FFPE tissue section (n=5/condition).

EXAMPLES

Example 1: HER4-Specific Human Monoclonal Antibody Selection by Phage Display Phage Display Selection The HUSCL library uses a single framework optimized for high level expression. The diversity was restricted to five amino acids (Y,N,D,G,S) and introduced in the six CDRs at the positions corresponding to the most contributing residues of the paratope. The antigen used was commercial human HER4-Fc (ref 1131-ER-50; RD Systems) or NRG1β1-stimulated EGFR/HER4 JMaCYT1-transfected NIH3T3 cells. The negative antigen was BSA or EGFR-transfected NIH3T3 cells. Two strategies of scFv selection from the HUSCL library were performed.

In the first strategy, HER4-Fc or BSA was coated at 100 ng/well in PBS (pH 7.4) on 96-well plates (Nunc Maxisorp, Paisley, UK) overnight at 4° C. After washing in PBS/tween 0.1% (PBS-T), non-specific binding sites were blocked with 1% gelatin/PBS-T, and $10^{10}$ scFv phages/ml were applied to each well for 2 h at room temperature as described previously. Revelation was done using anti-M13 antibody conjugated to peroxidase. To enrich the polyclonal scFv population in HER4-binders, this experiment was repeated in four successive selection rounds. Polyclonal scFv enriched in HER4-binders were transformed into BL21 (DE3)/pLysS bacteria. BL21 (DE3)/pLysS colonies (total 400) were picked into the 96-well microtiter plates to produce scFv by auto-induction and lysed. Human HER4-Fc or BSA was coated at 100 ng/well on 96-well plate overnight at 4° C. After washing (PBS/tween 0.1%), and blocking (1% gelatin/PBS-T), whole bacterial lysate containing monoclonal scFv was applied for 2 h at 4° C. Revelation was done using anti-c-Myc antibody conjugated to peroxidase.

In the second strategy, $10^{7}$ EGFR-transfected NIH3T3 cells were saturated in PBS-2% BSA for 2 h at 4° C., and subsequently pre-incubated with $10^{10}$ scFv phages/ml for 2 h at 4° C., to remove non-specific binders. The scFv phage supernatant was then applied for 2 h with 50 ng/ml NRG1β1-pre-stimulated EGFR/HER4 JMaCYT1-transfected NIH3T3 cells ($10^{7}$ cells) at 4° C. To enrich the population of HER4-binders, this experiment was repeated in three successive selection rounds, alternating with saturation in PBS-2% BSA or PBS-2% non-fat dry milk buffers. scFv populations enriched in HER4-binders were transformed in HB2151 bacteria, and picked colonies were further produced following 9 mM IPTG induction step for 16-30 h at 4° C. After centrifugation, scFv-containing supernatants were screened by flow cytometry towards wild-type or HER4 JMaCYT1-transfected NIH3T3 cells (see above) for 3 h at 4° C. After washings in PBS-2% FCS, cell-bound scFv were incubated with FITC-conjugated anti-Myc antibody for 45 min at 4° C.

From the 1st selection strategy, the 10 scFvs selected showed binding to EGFR/HER4 JMaCYT1-transfected NIH3T3 cells by flow cytometry (Data not shown), but no binding was evidenced to EGFR-transfected NIH3T3 cells. In this experiment, scFvs C2, C6, D5, E1, F4 and G4 demonstrated the stronger binding. From the 2nd selection strategy, the 9 scFvs selected were profiled by flow cytometry towards wild-type NIH3T3 cells, EGFR-vs EGFR/HER4 JMaCYT1-transfected NIH3T3 cells, and NRG1β1-stimulated EGFR/HER4 JMaCYT1-transfected NIH3T3 cells. scFv H2 bound to EGFR/HER4-transfected cells stimulated or not with NRG1β1, whereas scFvs C11 and D5 only targeted NRG1β1-stimulated EGFR/HER4 JMaCYT1-transfected cells. In contrast, scFvs G2 and G6 showed binding to EGFR-transfected cells, and unstimulated or NRG1β1-stimulated EGFR/HER4 JMaCYT1-transfected cells. F1 and H12 only bound to EGFR-transfected cells. scFv D12 targeted both wild-type and transfected cells, whereas scFv E7 showed no binding.

HER4-specific scFv selected from the 1st strategy (C6, D5 and F4) and the 2nd strategy (H2) were sub-cloned in human IgG1, κ format and were transiently expressed in HEK293T cells, and purified on HiTrap protein-A column (GE Healthcare).

ELISA Binding onto HER4-Fc Protein

Ninety six-well enzyme immunoassay plates (Nunc Maxisorp) were coated overnight at 4° C. with HER4-Fc antigen at a concentration of 250 ng/ml in PBS pH 7.4. After four washes in PBS, containing 0.1% Tween 20 (PBS-T), plates were saturated with a 2% solution of bovine serum albumin (BSA) in PBS-T buffer for 2 h at 37° C. Two-fold or ten-fold serial dilutions of purified HER4-specific mAbs were added after four washes in PBS-T and plates were incubated at 37° C. for 2 h. Following four washes in PBS-T, 100 μl of a peroxidase-conjugated goat anti-human F(ab')2 antibody (Jackson Immunoresearch) were added to each well. The conjugate was used at a 1:5000 dilution in PBS-T-2% BSA. The plates were incubated at 37° C. for 1 h and then washed three times in PBS-T and once in PBS. Finally a Tetramethylbenzidine solution (Sigma) was added for 30 min at ambient temperature in the dark. The reaction was stopped by adding 50 μl/well 1M $H_2SO_4$ and the absorbance was measured at 450 nm. We selected four anti-HER4 antibodies which bind in a dose-dependent manner to both human and mouse HER4-Fc by ELISA (Data not shown), but did not bind to EGFR, HER2 and HER3 receptors (data not shown). HER4-specific antibodies D5 and C6, giving 50%-absorbance at concentration of 20 ng/ml and 100 ng/ml respectively, on human HER4-Fc, are more efficient for binding than F4 and H2, which gave a 50%-absorbance at concentration around 1-5 μg/ml (FIG. 1).

Flow Cytometry Binding onto HER4-Positive Cervix Carcinoma Cells C33A

To confirm HER4 specificity, 15 μg/ml antibodies were each incubated with $3 \times 10^{5}$ cervix carcinoma cells C33A (ATCC HTB-31) for 2 h at 4° C. in PBS-1% FCS. After three washings in PBS-1% FCS, cells were probed with 1/100 dilution of FITC-conjugated goat anti-human Fc antibody (Sigma) for 1 h at 4° C. in the dark. After washings in PBS, HER4 binding onto C33A cells was analyzed by flow cytometry. All the anti-HER4 antibodies bind to HER3-negative HER4-positive C33A cells with different intensities, with regard to HER4-specific commercial antibody H4.77.16 (Ab77; Thermo Fisher). In this case, F4 showed similar binding as H4.77.16 whereas the others antibodies C6, D5 and H2 demonstrated a lower positive binding.

Figure 2:
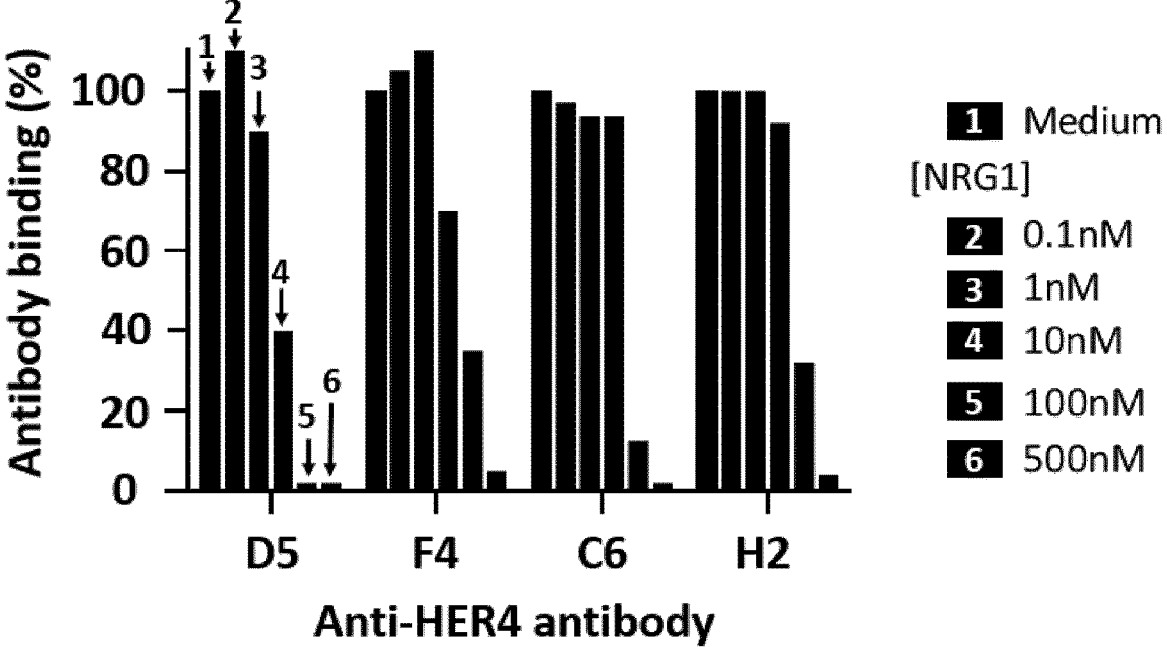
FIG. 2 shows the % binding of anti-HER4 antibodies D5, F4, C6 and H2 using various concentrations (0.1 nM to 500 nM) of NRG1β1. CTRL isotype is an irrelevant IgG1 antibody.

Example 2: Competition with NRG1β1 of the Anti-HER4 Human Antibodies of the Invention Cytometry competition experiments were performed in order to quantify the ability of NRG1β1 to inhibit antibody binding to HER4 in a C33A cell-based assay. To this end, $3 \times 10^5$ C33A cervix carcinoma cells were co-incubated with a non-saturating dose of 15 μg/ml antibody, and various concentrations of the competing NRG1β1 ligand (0.1 nM to 500 nM) for 1.5 h on ice. Cells were then washed and further incubated with a 1:100 dilution of FITC-conjugated goat anti-human Fc antibody (Sigma) for 1 h on ice, before cytometry analysis. Competition experiments by FACS demonstrated that C6 and H2 antibodies did not compete with 10 nM NRG1β1 (Data not shown) thus suggesting that these antibodies did not bind to the NRG1-binding site in physiological conditions. In contrast, antibodies D5 and F4 were partially inhibited by 10 nM NRG1β1, demonstrating that epitopes recognized by these antibodies are closed to or located in the NRG1-binding site, or could be sterically-impaired for antibody binding when NRG1 induces transconformation of active HER4 receptor for dimerization. Lower concentrations of NRG1β1 (0.1-1 nM) did not affect anti-HER4 binding (FIG. 2). Higher "non-physiological" concentrations of NRG1β1 (100-500 nM) inhibited the binding of antibodies to HER4 (FIG. 2). In these cases, F4 and H2 antibodies still demonstrated around 30%-residual binding at 100 nM NRG1β1.

Example 3: Inhibition of Cell Viability by the Anti-HER4 Human Antibodies of the Invention $1 \times 10^4$ C33A cells were cultured in each well of 96-well plates for 24 h in RPMI complete medium. Cells were either incubated with anti-HER4 antibodies at a final concentration of 100 μg/ml, or 1% serum-starved for 18 h at 37° C. before co-incubation of 100 μg/ml antibodies and 0.3 nM (long/ml) NRG1β1. After 5 days of culture, proliferation was measured by adding 20 μl/well of a solution containing the tetrazolium compound MTS [3-(4,5-dimethylthiazol-2-yl)-5-(3-carboxymethoxyphenyl)-2-(4-sulfophenyl)-2H-tetrazolium] and the electron coupling reagent PMS (phenazine methosulfate). MTS is reduced by cells into a formazan product that is soluble in tissue culture medium. The absorbance of the formazan at 490 nm can be measured using a spectrophotometer. Anti-HER4 antibody D5 inhibited 50% viability of the C33A cell line, with or without co-stimulation with NRG1β1. No significant inhibition was observed with untreated cells or after treatment with irrelevant antibody. In contrast, anti-HER4 antibodies C6, F4 and H2, used alone, induced 15% to 25% inhibition of cell viability; this inhibition being increased to 50% when NRG1β1 was added. Finally, the anti-HER4 antibody Ab77, kindly donated by Pr. Y. Yarden (Weizmann Institute) increased the viability of C33A cells, as previously proposed (Chen et al. 1996).

Example 4: Western Blot Analysis of HER4 Phosphorylation in C33A Cervix Cancer Cell Line after Stimulation with NRG1β1 and Treatment with Human Antibodies of the Invention $3 \times 10^5$ C33A cells were seeded in 12-well plates for 24 h in RPMI-10% FCS before 12 h-starvation in RPMI-1% FCS. Cells were then co-incubated with 20 μg/ml HER4-specific human antibodies and 1 nM (30 ng/ml) NRG1β1 in RPMI-1% FCS 1% for various times at 37° C. After washing in cold PBS, cells were scraped from plastic dishes using a rubber policeman in 0.5 ml cold PBS. After centrifugation, cell pellets were lysed in 50 μl of lysis buffer containing 50 mM Hepes pH 7.5, 150 mM NaCl, 1 mM EDTA, 1 mM EGTA, 1% Triton X-100 (v/v), 10% glycerol (v/v), 100 mM sodium fluoride, 1 mM sodium orthovanadate (Sigma), and one complete protease inhibitor mixture tablet (Roche Diagnostics, Meylan, France). After 45 min-incubation, samples were cleared of insoluble fraction by centrifugation and protein concentrations in cell lysates were determined by Bradford colorimetric reaction.

After electrophoresis on 10% SDS-PAGE under reducing conditions, the cell lysates were transferred to polyvinylidene difluoride membranes (Millipore, Molsheim, France) which were saturated in 25 mM Tris pH 7.4, 150 mM NaCl buffer containing 0.1% Tween 20 (TNT) and 5% nonfat dry milk for 2 h at ambient temperature. A 1 μg/ml solution in TNT-2% BSA of antibodies directed to total HER4 (E200, Abcam), HER4 phosphorylated Y1056 (Ab92782, Abcam) or Y1284 (ref. 4757S, CST) were incubated for 18 h at 4° C. GAPDH, as loading control, was detected by a specific antibody (ref. 5174S, CST). After three washes in TNT, blots were incubated with peroxidase-conjugated mouse-specific (1/2000) or rabbit-specific (1/10000) antibodies (Sigma) as appropriate, for 1 h in TNT-2% nonfat dry milk at ambient temperature. After 3 washes in TNT, the blots were visualized using chemiluminescent substrate (Western Lightning Plus-ECL, Perkin Elmer; or SuperSignal West femto, ThermoFisher). Anti-HER4 antibodies D5, F4, C6 and H2 did not affect HER4 expression until 24 h-end of experiment, in contrast to strong HER4 downregulation induced by HER4-specific control antibody Ab77. F4 antibody, but not D5, C6 and H2, increased basal Y1056 phosphorylation on the HER4 receptor. On the other hand, D5, C6 and H2 antibodies, but not F4, inhibited NRG1β1-induced Y1284 phosphorylation on the HER4 receptor after 1 h-post treatment. HER4-specific control antibody Ab77, which has been shown to enhance cell viability of C33A cells, strongly increased NRG1β1-induced Y1284 phosphorylation (Data not shown).

Example 5: Biased Routing/Signaling of 4ICD Induced by Anti-HER4 Human Antibodies of the Invention in JMaCYT1- Vs JMaCYT2-Transfected BT549 Cells HER3-negative HER4-negative BT549 cells were transiently-transfected with JMaCYT1 or JMaCYT2 HER4 isoforms. To this end, BT549 cells were grown in P150 cm2 Petri dishes at 37° C. under 5% CO2. When 80% confluency was reached, cell medium was removed and replaced by 15 ml of fresh cell culture medium (DMEM supplemented with penicillin-streptomycin, 2 mM Hepes and 1×MEM non-essential amino-acids solution). In parallel, a transfection mixture containing 20 μl of JMaCYT1 or JMaCYT2 HER4 plasmid at 1 μg/ml, 30 μl of JetPEI (Polysciences) at 1 mg/ml in 1 ml 150 mM NaCl was prepared and pre-incubated for 30 min at room temperature before the addition to the cells. The Petri dishes were then incubated at 37° C. under 5% CO2 for 6 h in DMEM-10% FCS followed by 12 h-starvation in DMEM-1% FCS before treatment with anti-HER4 antibodies, or control antibody Rituximab (RTX) at 20 μg/ml, with or without 1 nM (30 ng/ml) NRG1β1, for an additional 6 h.

Transfected BT549 cells were scraped from plastic dishes using a rubber policeman as described above and washed twice in cold PBS. For subcellular fractionation, cells were resuspended in lml cold Mitochondrial Isolation Buffer pH7.4 (MIB) containing 200 mM sucrose, 10 mM TRIS/MOPS, 1 mM TRIS/EGTA and proteases inhibitors (Roche). The cell suspension was transferred to a 30 ml Nalgene tube (ref3138-0030, ThermoFisher), and immediately homogenized using Ultraturrax T18 (IKA) for 10-15 sec at 2.5 speed. Cell lysis was checked under microscope. If needed, cells were homogenized one more time to reach 90% cell lysis (similar time and speed as described above). 50 µl cell lysates were saved as Whole Cell Lysates (WCL). Remaining lysates were then centrifuged at 600 g at 4° C. for 10 min.

From the centrifuged lysates, the supernatant containing cytoplasm and mitochondria was saved and further centrifuged at 600 g for 10 min to remove nuclei contamination, before a second centrifugation at 7500 g for 10 min at 4° C. to pellet mitochondria. Mitochondria pellet was resuspended in 50 µl lysis buffer (Mitochondrial Fraction) and supernatant-containing cytoplasm was precipitated for 1 h with 4V cold acetone, centrifuged and dissolved in 50 µl lysis buffer (Cytosolic Fraction). From the centrifuged lysates, the pellet containing nuclei was washed, and centrifuged twice again at 600 g at 4° C. for 10 min (1 ml MIB per wash) to remove all cytoplasm and mitochondria soluble contaminants. The 3-times washed nuclei pellets were pooled in 50 µl lysis buffer as described above.

All collected fractions were dosed using Nanodrop 2000 (ThermoFisher), diluted with 2× Laemmli Buffer and boiled for 10 min at 95° C. 50 µg proteins of each fraction were loaded on SDS-PAGE. After electrophoresis on 10% SDS-PAGE under reducing conditions, the whole cell lysates (WCL), as well as nuclear, mitochondrial and cytosolic subcellular fractions were transferred to polyvinylidene difluoride membranes. Membranes were further probed with anti-HER4 antibody E200 (Abcam), which identifies the whole HER4 receptor and its IntraCellular Domain 4ICD, and with anti-aTubulin (ref. 3873S, CST), anti-VDCA1 (Voltage-Dependent Anion-selective Channel 1; ref. 4661S, CST) or –TIM23 (Mitochondrial Import Inner Membrane translocase subunit; Becton Dickinson, ref. 611223), and anti-Histone H3 (ref. 9715S, CST) antibodies which identify the cytosolic, mitochondrial and nuclear fractions respectively. After three washes in TNT, blots were incubated with peroxidase-conjugated mouse-specific (1/10000) or rabbit-specific (1/10000) antibodies (Sigma) as appropriate, for 1 h in TNT-2% nonfat dry milk at ambient temperature. After 3 washes in TNT, the blots were visualized using chemiluminescent substrate (Western Lightning Plus-ECL, Perkin Elmer). Anti-HER4 antibody C6 biased 4ICD routing towards the mitochondria in JMaCYT1-transfected BT549 cells; this effect being observed either with or without co-stimulation with NRG1β1. H2 antibody induced similar biased 4ICD cell fate towards mitochondria, but only when NRG1β1 was added (Data not shown). This antibody-induced biased signaling of 4ICD was not observed for C6 and H2 antibodies in JMaCYT2-transfected BT549 cells (Data not shown), thus suggesting 4ICD-biased routing is specific to cells expressing the JMaCYT1 HER4 isoform. In contrast, antibodies D5 and F4 did not induce biased 4ICD routing towards mitochondria, but maintained 4ICD into the nucleus, either in JMaCYT1 or JMaCYT2-transfected BT549 cells.

Example 6: Mitochondria Depolarization Induced by Human Anti-HER4 Antibody C6, but not by Antibody D5, in JMaCYT1-Transfected BT549 Cells The antibodies C6, which biased 4ICD cell fate towards mitochondria, and D5, which did not induced 4ICD bias, were produced and purified in CHO cells (outsourcing from Evitria AG, Zurich, Switzerland). BT549 cells were transiently transfected with Mock, JMaCYT1 or JMaCYT2 isoforms in P150 Petri dishes as described above. After 24 h transfection, 2×105 cells originating from the same pool of transfection (to ensure similar transfection conditions) were seeded in 12-well plates for 10 h in DMEM-10% FCS, before starvation in DMEM-1% FCS 1% for additional 12 h. After one PBS wash, cells were treated with 20 µg/ml of anti-HER4 antibodies C6 and D5, or anti-HER4 antibody Ab77 (Chen et al. 1996) in DMEM-1% FCS for 24 h at 37° C., before DioC6 staining for analysis of mitochondria depolarization. To this end, transfected-BT549 cells treated with antibodies were washed in PBS, trypsinized and further incubated with 20 nM of the mitochondria fluorescent dye 3,3'-dihexyloxacarbocyanine iodide (DioC6) in PBS, for 20 min at 37° C. in the dark. As positive control of depolarization, untreated transfected-BT549 cells were incubated with 20 nM DioC6 and 100 µM of the protonophore carboxyl cyanide m-cholophenylhydrazine (CCCP). After centrifugation, cells were resuspended in PBS and analyzed by FL1 flow cytometry. Anti-HER4 antibody C6 induced mitochondria depolarization in JMaCYT1-transfected BT549 cells, but not in Mock- or JMaCYT2-transfected cells. In contrast, antibodies D5 or Ab77 did not induce mitochondria depolarization (Data not shown). As positive control, the protonophore CCCP strongly depolarized mitochondria in Mock-, JMaCYT1- or JMaCYT2-transfected cells. Altogether, the results demonstrated that the human anti-HER4 antibody C6 induced biased 4ICD routing to mitochondria in JMaCYT1 tumor cells, but not in JMaCYT2, leading to membrane mitochondria depolarization. In contrast, D5 antibody triggered neither 4ICD cell fate towards mitochondria nor mitochondria depolarization, but maintained 4ICD into the nucleus.

Example 7: Western Blot Analysis of HER4 Phosphorylation on JMaCYT1- Vs JMaCYT2-Transfected BT549 Cells Treated with C6 and D5 Antibodies BT549 cells were transiently transfected with Mock, JMaCYT1 or JMaCYT2 isoforms in P150 Petri dishes as described above. After 24 h transfection, 2×105 cells originating from the same pool of transfection were seeded in 12-well plates for 10 h in DMEM-10% FCS, before starvation in DMEM-1% FCS for additional 12 h. After one PBS wash, cells were treated with 20 µg/ml human anti-HER4 antibodies C6 and D5, or irrelevant antibodies Rituximab (Rtx) or Ipilimuimab (Ipi), in DMEM-1% FCS for 30 min, 60 min or 90 min at 37° C. After washing twice in cold PBS, cells were scraped from Petri dishes using a rubber policeman in 50 µl of boiled Laemmli extraction buffer containing 60 mM Tris pH6.8, 10% glycerol (v/v), 1% SDS (v/v). Samples were dosed with Nanodrop 2000 (ThermoFisher) and 20 µg of protein were submitted to 10% SDS-PAGE under reducing conditions. The cell lysates were then transferred to polyvinylidene difluoride membranes (Millipore, Molsheim, France) which were saturated in 25 mM Tris pH 7.4, 150 mM NaCl buffer containing 0.1% Tween 20 (TNT) and 5% nonfat dry milk for 2 h at ambient temperature. A 1 µg/ml solution in TNT-2% BSA of antibodies directed to total HER4 (E200, Abcam), HER4 phosphorylated Y1056 (bs-13094R, Bioss Antibodies), Y1284 (ref. 4757S, CST) or Y984 (ref. 3790S, CST) were incubated for 18 h at 4° C. Beta-actin, as loading control, was detected by a specific antibody (ref. 3700, CST). After three washes in TNT, blots were incubated with peroxidase-conjugated mouse-specific (1/2000) or rabbit-specific (1/10000) antibodies (Sigma) as appropriate, for 1 h in TNT-2% nonfat dry milk at ambient temperature. After 3 washes in TNT, the blots were visualized using chemiluminescent substrate (Western Lightning Plus-ECL, Perkin Elmer; or SuperSignal West femto, ThermoFisher). 60 min-treatment of C6 antibody induced phosphorylation of Y1056 and Y984 on HER4, but not Y1284, in JMaCYT1 BT549 cells; such effects being also observed with D5 antibody, but at lower intensity. In contrast, no effect on HER4 phosphorylation was observed in D5- or C6-treated JMaCYT2 cells. Ab77 abrogated all the HER4 phosphorylation profile both in JMaCYT1- and JMaCYT2-transfected BT549. Concomitantly, D5 antibody inhibited pAKT S473 and pp38 T180/Y182 in JMaCYT1 BT549 cells; such effects being also observed at lower intensity with C6 antibody (Data not shown). As confirmed in a time-dependent manner (Data not shown), D5 and C6 induced Y984 and Y1056 phosphorylation from 30 min to 60 min post-treatment, but unexpectedly C6 abolished HER4 phosphorylation at 90 min post-treatment. All these effects translated to an increased expression of 4ICD in D5- and C6-treated JMaCYT1 BT549 cells at 90 min (Data not shown).

Example 8: Effect of Human Anti-HER4 Antibodies C6 and D5 on Poly(ADP-Ribose) Polymerase (PARP) Cleavage and γH2AX-Mediated Double-Strand Breaks in C33A Cervix Cancer Cell Line $2\times10^5$ C33A cells were seeded in 12-well plates for 24 h in RPMI-10% FCS. After one PBS wash, cells were treated with 20 µg/ml of anti-HER4 antibodies D5 and C6, or irrelevant antibody Rituximab (Rtx), in RPMI-10% FCS from 24 h to 72 h at 37° C. After washing twice in cold PBS, cells were lysed, submitted to PAGE-SDS and western blot as described above. Detection was performed with appropriate primary antibodies directed to cleaved PARP (E51, Abcam) and γH2AX (ref. 05-636, Millipore). Antibodies D5 and C6 increased PARP cleavage at 72 h post-treatment, with regard to lower PARP activation induced by irrelevant antibody rituximab; this mechanism initiating HER4 antibody-induced apoptosis of C33A cervix cancer cells. Concomitantly, increased γH2AX activation, which signed DNA double-strand breaks, was observed in D5- and C6-treated C33A cells from 48 h to 72 h post-treatment, compared to control. Unexpectedly, C6 increased HER4 expression at 72 h post-treatment (Data not shown). These effects were also observed, but at different intensities and time-frame, in ovarian COV318 and Kuramochi, triple-negative breast MDA-MB-453 and HCC1187 cancer cell lines (data not shown).

Example 9: HER4 Epitope Mapping of Human Anti-HER4 Antibodies D5 and C6

The HER4 epitope mapping of antibodies D5 and C6 was predicted using the MAbTope technology (Bourquard et al. 2015) developed by the MAbSilico company (Nouzilly, France). This technology, based on mathematical formalization of 3D antibody structures of both antibody and target, combined to machine-learning, allows identifying residues involved in the target epitope. To this end, homology models of the 3D structures of the variable domains of C6 and D5 were made using Modeller program (Webb et al. 2017). Given the high similarities between the sequences of the two antibodies D5 and C6, the same templates were used for modelling. C6 and D5 variable domains were PDB:4ZS6 (Yu et al. 2015) for VH and PDB:4NIK (Robin et al. 2014)

for VL. The relative orientation of VH and VL domains was taken from PDB:4ZS6. The 3D structure chosen for the target HER4 receptor was PDB:2AHX (Bouyain et al. 2005). The top30 ranked conformations of the antibody/HER4 complex are well gathered (Data not shown), confirming that the docking procedure is correct. From the top30 ranking structures, the amino-acid residues from the sequence of the HER4 extra-cellular domain were scored for their probability to belong to the epitope of antibodies D5 and C6. Four predicted areas were identified to belong to the D5 and C6 putative epitopes: P1 606-623, P2 573-593, P3 260-279 and P4 622-642 (Data not shown).

Mutated variants of HER4 were designed within the four predicted areas (HER4_P1 to P4) (Data not shown). Only the surface amino-acids were mutated into alanine, ensuring that the structure of the protein was not altered. All the HER4 constructs were flanked by a N-terminal Flag. HEK293 cells were transiently transfected with the WT HER4, one of the mutants HER4_P1 to P4 or left untransfected (mock). Cells were fixed before incubation with C6 or D5 antibodies. The HER4 overexpression in HEK-transfected cells was monitored with a PE-labelled anti-Flag antibody (Data not shown), and C6 or D5 binding was detected with an APC-labelled anti-IgG antibody (in abscissa in Data not shown). The number of APC- and PE-positive cells were collected from four independent experiments and normalized as a percentage of the maximal APC+/PE+ population (Data not shown). The percentage of PE+/APC+ cells, which signed HER4 expression at the cell surface and HER4 antibody binding, was increased in HER4 WT cells compared with no PE+/APC+ cell expression measured in mock-transfected cells. Compared to HER4 WT expression, the percentage of PE+/APC+ cells decreased in HER4 mutated_P1- and P2-transfected cells whereas it was not modified in mutated_P3- and_ P4-transfected cells (Data not shown). Taken together, these results experimentally demonstrated that anti-HER4 antibodies D5 and C6 share a common conformational epitope located in domain IV, and restricted to regions 605-620 (part of P1 area) and 575-592 (part of P2 area).

Inside the two regions P1 606-623 and P2 573-593 experimentally-identified, surface residues (those ensuring that the structure of the protein was not altered) were divided in three categories as a function of their raw probability to belong to the epitope (Data not shown). For epitope mapping of C6 antibody, residue E613 from sequence HER4 was identified as very highly probable, whereas residue H615 was identified as probable (Data not shown). For epitope mapping of D5 antibody, only domain IV-residue E613 was very highly probable residue, and residue D611 and residue H615 belonged to highly probable residues (Data not shown). Altogether, these predictions indicated that human anti-HER4 antibodies D5 and C6 share common conformational epitopes on the HER4 extracellular region.

To test the efficacy of the 4 anti-HER4 Abs, we used an MTS assay to assess the metabolic activity of C-33A cells. Compared with irrelevant control Ab (Ctrl), the metabolic activity of C-33A cells was reduced by 50% when incubated with D5 and by 15%-30% in the presence of C6, F4, and H2 (Data not shown). Coincubation with 10 ng/mL NRG1 increased the C6-, F4- and H2-mediated metabolic activity inhibition to 50% (Data not shown), suggesting that NRG1 potentiates the effect of these Abs. Conversely, NRG1 did not improve D5 inhibitory effect. The anti-HER4 agonist Ab Ab77 increased the metabolic activity of unstimulated and NRG1-stimulated C-33A cells up to 120%, as previously suggested. 37. To confirm, we analyzed the clonogenic survival of C-33A cells after treatment with anti-HER4 Abs, to investigate whether selected Abs could affect colony formation (Data not shown). At day 15 posttreatment, the clonogenic survival was notably reduced in cells incubated with 5 µg/mL Abs D5 and C6 than in cultures incubated with control IgG (Data not shown). As positive controls, trastuzumab (Data not shown) as well as dose-dependent irradiation (Data not shown), also affected clonogenic survival of C-33A cells.

Example 10: C6 mAb is a PAM/Agonist Anti-HER4 mAb Inducing Cell Death by Sharing Some of NRG1 Mechanisms of Action We demonstrated that C6 mAb induces 4ICD location to the mitochondria, even in presence of NRG1. In contrast, D5 mAb doesn't induce this location and its efficacy is independent of NRG1 addition (Data not shown). To uncover D5 and C6 mechanisms of action, we first analyzed MMP changes after mAbs treatment for 24 h. As expected from subcellular fractionation experiments, only C6 mAb induces mitochondrial depolarization from JMa/CYT1-transfected BT549 cells (Data not shown). D5 mAb, which doesn't drive 4ICD to the mitochondria, doesn't induce mitochondrial depolarization, suggesting this mAb induces cell death through a mechanism of action distinct from C6 mAb and NRG1. D5 and C6 mAbs don't induce MMP changes from JMa/CYT2-transfected cells, confirming that depolarization following 4ICD location to mitochondria is a specific mechanism to the JMa/CYT1 tumor suppressor isoform. Since C6 mAb induces mitochondrial depolarization, we investigated ROS production after D5 and C6 mAbs treatment, from JMa/CYT1 and JMa/CYT2-transfected BT549 cells. As expected, only C6 mAb increases ROS production from JMa/CYT1 cells (Data not shown). Although modest, this increase confirms that 4ICD location to mitochondria, mitochondrial depolarization and ROS production, as we observed for NRG1, are closely connected. Interestingly, D5 and C6 mAbs also increase ROS production from JMa/CYT2 cells (Data not shown). These results suggest that ROS are involved in cell death induced by mAbs from this isoform, but contradictorily to JMa/CYT1, this cell death doesn't involve mitochondria.

Because C6 mAb seems to act as NRG1, we were then searching for evidences for HER4 activation. To this end, we investigated HER4 phosphorylation after mAbs treatment. From JMa/CYT1 cells, D5 and C6 mAbs strongly induce phosphorylation of JMa/CYT1 on Y1056, a phosphorylation site described as essential for HER4 tumor suppressor function (Gallo et al., 2006). This result indicates that D5 and C6 are agonist anti-HER4 mAbs (Data not shown). In contrast, agonist Ab77 only induces JMa/CYT1 phosphorylation on Y984, a site responsible for 4ICD-STATSA binding (Han et al., 2016). We no detected HER4 phosphorylation after mAbs treatment from JMa/CYT2 cells. This last result is coherent for Y1056, only present into CYT1 but surprising for Y984, since this site is shared by both isoforms. Besides phosphorylation, HER4 activation can be analyzed through receptor cleavage and 4ICD release. Since mAbs induce JMa/CYT1 phosphorylation, we investigated 4ICD release following mAbs treatment. From JMa/CYT1 cells, D5 and C6 increase 4ICD release over time, suggesting that JMa/CYT1 cleavage occurs and therefore HER4 was activated (Data not shown). Taken together, these results indicate that D5 and C6 mAbs induce cell death through JMa/CYT1 activation. Because C6 mAb acts by sharing some NRG1 mechanisms of action with an epitope distinct from NRG1, we believe this mAb is a PAM/agonist.

Example 11: In Vivo Effect of Human Anti-HER4 Antibodies D5 and C6 on Tumor Growth of Xenografted Mice Athymic, 6- to 8-week-old, female BALB/c nude mice were purchased from Charles River Laboratories. HER4-positive HER3-negative ovarian cancer COV434, cervix cancer C33A and triple-negative breast cancer HCC1187 cells were injected s.c. into the right flank of athymic BALB/c nude mice ($10 \times 10^6$ cells v/v in matrigel). All in vivo experiments were done in compliance with the French guidelines for experimental animal studies (Agreement no. C34-172-27).

Tumor-bearing mice were randomized in the different treatment groups when the tumors reached an approximate volume of 100 mm³. The mice were treated by i.p. injections of HER4-specific antibodies D5 and C6 vs CTRL IgG. The amount of injected antibody was 300 µg/injection (15 mg/kg), twice a week, for 4 weeks consecutively (Q3D-4W), except for HCC1187 experiment (20 mg/kg, Q3D-6W with an initial 2× dose). As positive control of treatment, carboplatin was used at 1.2 mg/injection (60 mg/kg), one time per week for 4 weeks. Tumor sizes were measured twice weekly with a caliper and the volumes were calculated by the formula D1×D2×D3/2. Tumor progression was calculated using the formula [(final volume)-(initial volume)]/(initial volume).

Figure 3A:
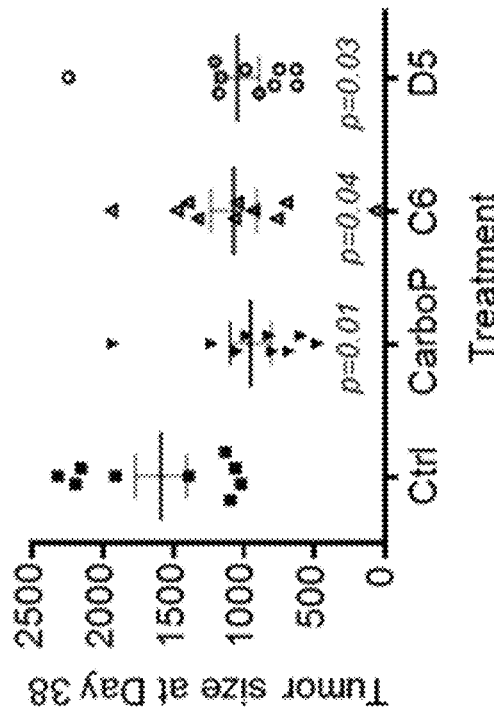
Figure 3A:
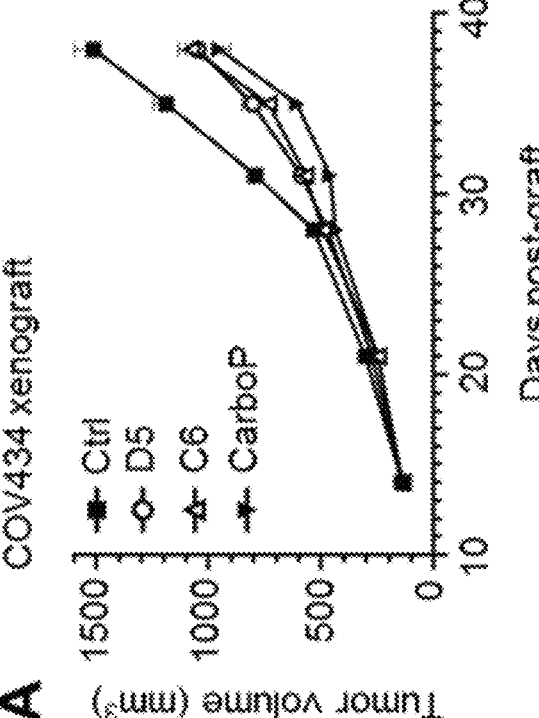
Figure 3A:
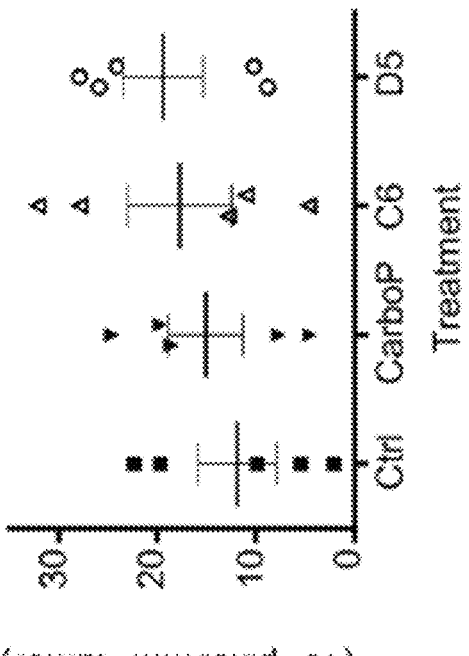
Figures 3B, 3C:
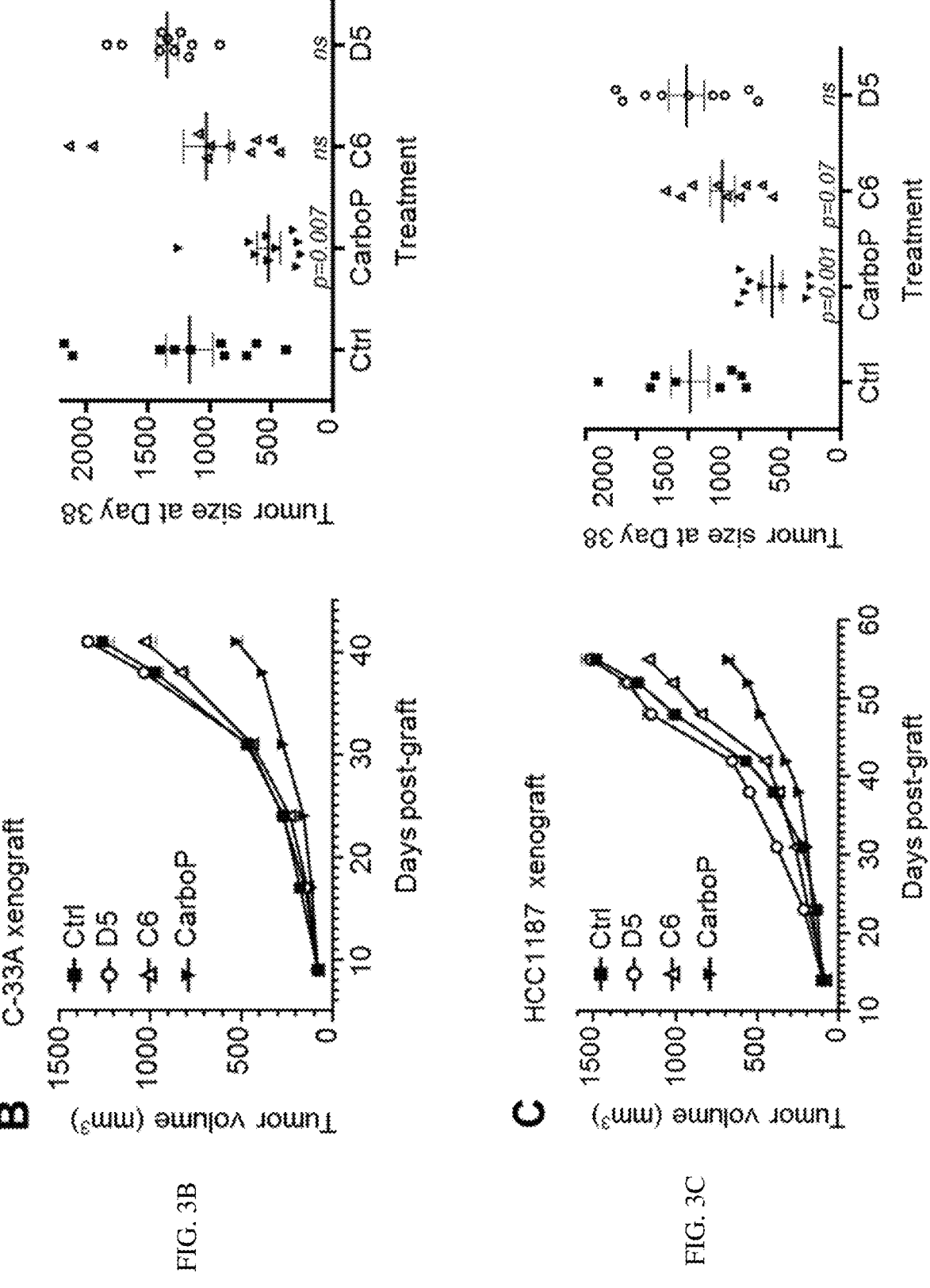

As shown in FIGS. 3A to 3C, we observed a significant 33%-reduction of ovarian COV434 tumor growth in D5 and C6-treated mice at day 38 post-tumor implantation (p=0.049 and p=0.034 respectively) (3 days after the end of antibody treatment; day 35), with regard to mean tumor size measured in mice treated with control IgG. At day 38 post-tumor implantation, carboplatin, as positive control treatment, induced 37%-reduction in tumor size (p=0.015) (FIG. 3A).

In correlation, analysis of COV434 tumor samples at day 38 postxenograft (Data not shown) showed that the number of cancer cells positive for cleaved caspase-3 (a marker of apoptosis) tend to increase in mice treated with the anti-HER4 Abs D5 and C6 compared with control-treated mice (FIG. 3A). At day 41 postxenograft, the mean tumor volume was reduced by 18% in mice xenografted with C-33A cells and treated with C6 compared with control (IgG), but this difference was not significant (P=0.617) (FIG. 3B). D5 did not affect tumor growth. Conversely, tumor volume was reduced by 59% (at day 38 postgraft) in mice treated with carboplatin (P=0.007). In mice xenografted with HCC1187 cells, tumor volume was reduced by 21.5% (at day 55 postxenograft, 4 days after the treatment end; day 51) after treatment with C6 compared with control (IgG) (P=0.07) (FIG. 3C). D5 did not have any effect. At day 55 postgraft, tumor size was reduced by 54% in carboplatin-treated mice (P=0.001).

Taken together, these results demonstrate that anti-HER4 Ab C6 delayed tumor growth in mice xenografted with either ovarian and triple-negative breast cancer cell lines.

Discussion

The development of antagonist mAbs is a classical and effective way to inhibit cancer progression, with the targeting of EGFR and HER2 as example of success-story (Hynes and Lane, 2005; Mota et al., 2017). The characterization of HER4-specific mAbs was initially based on the same concept, i.e. blocking receptor activity to kill cancer cell (Ben-Yosef et al., 2007; Starr et al., 2006). Because HER4 is unique among HER family, in terms of mechanism of action and functions, we believe this way as being inappropriate to target HER4 for a therapeutic purpose. Since conflicting results concerning the correlation between patient's survival and HER4 expression have been described (Barnes et al., 2005; Bièche et al., 2003), it is now clear that HER4 harbors oncogene and tumor suppressor functions related to its four isoforms (Kim et al., 2016; Machleidt et al., 2013). In this context, previously-described anti-HER4 mAbs showed disappointing results because HER4 was targeted as a whole, both blocking its oncogene and tumor suppressor activities (Hollmén et al., 2009; Okazaki et al., 2016).

The inventors characterized the agonist anti-HER4 antibody C6 that mimics NRG1 effects, by promoting cleavage and translocation of 4ICD to mitochondria, leading to antibody-induced cell death from JMa/CYT1 HER4-expressing cancer cells. Cell death occurred after ROS production through mitochondrial membrane depolarization, γH2AX expression sensing DNA damage and Y1056 HER4 phosphorylation. All these C6-induced biological events translated in vivo to tumor growth regression in ovarian cancer and TNBC. In HER3neg HER4pos C-33A cells, NRG1 induced PARP cleavage over time with DNA fragmentation. The type of cell death induced by NRG1 through HER4 is currently unknown and needs to be investigated. Because HER4 is very important for brain homeostasis, and PARP cleavage after NRG1 stimulation is characteristic for neurodegeneration, various cell death mechanisms can potentially be activated through HER4 (Chaitanya et al., 2010; Fricker et al., 2018). We suspect an unconventional cell death like necroptosis or parthanatos with caspase-independent mechanism involving endoplasmic reticulum stress.

To sustain this hypothesis, we measured an increase of protein level in NRG1-induced cell death of HCC1187 cells, suggesting protein synthesis increased, as previously described (Han et al., 2013). Secondly, this synthesis was associated with ROS production and JNK activation (Urano et al., 2000), two events we found associated to JMa/CYT1 isoform after NRG1 stimulation. Protein synthesis could be also associated to parthanatos, a mitochondrial cell death implicating ROS, AIF release and PARP as central mediator (Fatokun et al., 2014). The anti-tumor effect of C6 antibody is related to HER4 JMa/CYT1 cleavage and formation of a stable active 4ICD fragment located into mitochondria. Many evidences were described concerning the HER4 tumor suppressor function through 4ICD (Feng et al., 2007; Naresh et al., 2006), but without defining the exact role of each isoform. We excluded JMb isoforms because their expression is absent in cancer or limited to certain tissues (Veikkolainen et al., 2011). Using plasmids encoding for both "full-length" JMa isoforms, we demonstrated that NRG1-induced cell death occurs through JMa/CYT1, whereas JMa/CYT2 induced cell survival. We used BT549 cells, a relevant model which does not express HER3 and HER4, and which belongs to the TNBC subtype, the most aggressive breast cancer with unmet medical needs. Because HER4 is expressed in about 20% of TNBC patients (Machleidt et al., 2013), results from our study using HCC1187 TNBC xenograft demonstrated that targeting HER4 with agonist antibodies could be an efficient alternative to treat TNBC. Indeed, in our model, stimulation of JMa/CYT1 by NRG1 increased PARP cleavage in contrast to NRG1-induced JMa/CYT2 activation, thus showing the dichotomy between the tumor suppressor isoform JMa/CYT1 and the pro-survival isoform JMa/CYT2. JMa/CYT1 isoform acts by activating JNK, relocating 4ICD to the mitochondria and increasing ROS production. Altogether, these events led to cell death but we still have to precisely decipher the pathway. We hypothesized that ROS amplification inducing DNA damage could be due to transient mitochondrial membrane potential (MMP) change, leading to a cell death mechanism called RIRR (ROS-Induced ROS Release), a phenomenon of ROS amplification through mitochondria (Zorov et al., 2006).

We used this model as template for HER4 antibody discovery. Because NRG1 induces cell death by activating JMa/CYT1, we tried to potentiate this function without hampering NRG1 action on HER4. To this end, we performed whole cell panning by phage display using NRG1-stimulated JMa/CYT1 cells to select NRG1 agonistic/modulator anti-HER4 mAbs with unique capacities. Firstly, NRG1 binding to HER4 differently affects mAb binding to the receptor. Using C-33A cells, we demonstrated that all mAbs can bind to HER4 in presence of 30 ng/ml NRG1, a concentration inducing cancer cell death. Secondly, selected mAbs act synergistically with NRG1 to decrease metabolic activity of cells. Thirdly, epitopes form antibodies C6 and D5 are far from the NRG1 binding site (Liu et al., 2012) on HER4, suggesting that cooperation between HER4-specific mAbs and NRG1 could occur at the cell surface. Similarly to NRG1, we demonstrated that C6 mAb induces HER4/4ICD location to the mitochondria, mitochondrial depolarization and ROS production, leading to cell death. These JMa/CYT1-triggered pathways suggest that the 16 AA stretch into CYT1 is crucial for cell death. Interestingly, previously-described anti-HER4 antibody MAb-3 (Starr et al., 2006) has been demonstrated to enhance apoptosis in HER4pos NSCLC cell line, with an increase of sub-diploid cells signing DNA damage. Using the same MAb-3 antibody, Ben-Yosef et al. observed multiple apoptotic cells with pyknotic and fragmented nuclei, karyorrhexis, and loss of cytoplasm in sections of xenografted prostate tumors resected from MAb-3-treated nude mice (Ben-Yosef et al., 2007). In contrast, JMa/CYT1 transgenic mice demonstrated enhanced breast cancer tumorigenesis, compared with JMa/CYT2 counterpart, with no apoptosis observed (Wali et al., 2014a). Thus, cell death induction seems to be a critical point for inhibiting tumorigenesis via HER4 (Wali et al., 2014b). We demonstrated C-33 that C6 mAb was effective to kill ovary and TNBC cancer cells in vitro by inducing PARP cleavage and DNA damage, and in vivo by reducing tumor growth. Pre-clinical studies must be pursued to confirm this way, especially in TNBC where these new first-in-class anti-HER4 mAbs could benefit to TNBC patients.

Finally, because C6 mAb has a different binding site than NRG1 on HER4, our results suggest that similar pathways can be triggered from different receptor conformation and indicate that C6 could be an allosteric modulator of the HER4 receptor. Based on discoveries in GPCR biology, allosteric modulation is an important mechanism which has been recently adapted from small to large molecules (Webb et al., 2013; Wootten et al., 2013). By acting on the receptor, allosteric molecules can modulate endogenic ligand binding and/or signaling. The effect of C6 and H2 antibodies, combined to NRG1 binding on HER4, could exemplified allosteric modulation, with cooperation to initialize new signaling pathways through HER4, non-permitted for each molecule by themselves (Data not shown). This phenomenon probably implicates receptor rearrangement, and because C6, H2, Ab77 (Chen et al., 1996) and mAb1479 (Hollinén et al., 2012) have epitopes closely related but very different mechanism of action, this suggests that minor differences in conformational changes can induce major differences in signaling and cell fate. More importantly, we demonstrated that we can induce biased signaling with RTK-specific antibodies, similarly as observed with molecules targeting GPCR. From JMa/CYT1, C6 mAb locates 4ICD to the mitochondria whereas Ab77 mAb locates 4ICD into the cytosol of JMa/CYT1-expressing cells, resulting in different cell fate. Altogether, our observations pave the way to next-generation of mAbs with "biasing properties" in cancer.

REFERENCES

Throughout this application, various references describe the state of the art to which this invention pertains. The disclosures of these references are hereby incorporated by reference into the present disclosure.

Canfield K, Li J, Wilkins O M, Morrison M M, Ung M, Wells W, Williams C R, Liby K T, Vullhorst D, Buonanno A, Hu H, Schiff R, Cook R S, Kurokawa M. Receptor tyrosine kinase ERBB4 mediates acquired resistance to ERBB2 inhibitors in breast cancer cells. Cell Cycle. 2015; 14(4):648-55

Prickett T D, Agrawal N S, Wei X, Yates K E, Lin J C, Wunderlich J R, Cronin J C, Cruz P, Rosenberg S A, Samuels Y. Analysis of the tyrosine kinome in melanoma reveals recurrent mutations in ERBB4. Nat Genet. 2009 October; 41(10):1127-32

Elenius K1, Corfas G, Paul S, Choi C J, Rio C, Plowman G D, Klagsbrun M. A novel juxtamembrane domain isoform of HER4/ErbB4. Isoform-specific tissue distribution and differential processing in response to phorbol ester. J Biol Chem. 1997 Oct. 17; 272(42):26761-8

Elenius K1, Choi C J, Paul S, Santiestevan E, Nishi E, Klagsbrun M. Characterization of a naturally occurring ErbB4 isoform that does not bind or activate phosphatidyl inositol 3-kinase. Oncogene. 1999 Apr. 22; 18(16):2607-15

Williams C C1, Allison J G, Vidal G A, Burow M E, Beckman B S, Marrero L, Jones F E. The ERBB4/HER4 receptor tyrosine kinase regulates gene expression by functioning as a STAT5A nuclear chaperone. J Cell Biol. 2004 Nov. 8; 167(3):469-78

Kainulainen V1, Sundvall M, Määttä J A, Santiestevan E, Klagsbrun M, Elenius K. A natural ErbB4 isoform that does not activate phosphoinositide 3-kinase mediates proliferation but not survival or chemotaxis. J Biol Chem. 2000 Mar. 24; 275(12):8641-9

Das P M1, Thor A D, Edgerton S M, Barry S K, Chen D F, Jones F E. Reactivation of epigenetically silenced HER4/ERBB4 results in apoptosis of breast tumor cells. Oncogene. 2010 Sep. 16; 29(37):5214-9

Veikkolainen V1, Vaparanta K, Halkilahti K, Iljin K, Sundvall M, Elenius K. Function of ERBB4 is determined by alternative splicing., Cell Cycle. 2011 Aug. 15; 10(16):2647-57

Muraoka-Cook R S, Sandahl M A, Strunk K E, Miraglia L C, Husted C, Hunter D M, Elenius K, Chodosh L A, Earp H S: ErbB4 splice variants Cyt1 and Cyt2 differ by 16 amino acids and exert opposing effects on the mammary epithelium in vivo. Mol Cell Biol. 2009, 29 (18): 4935-4948.

Ji-Yeon Kim, Hae Hyun Jung, In-Gu Do, SooYoun Bae, Se Kyung Lee, Seok Won Kim, Jeong Eon Lee, Seok Jin Nam, Jin Seok Ahn, Yeon Hee Park, and Young-Hyuck Im., BMC Cancer. 2016 Feb. 22; 16:138

Machleidt A., Buchholz S., Diermeier-Daucher S., Zeman F., Ortmann 0 Brockhoff G. The prognostic value of Her4 receptor isoform expression in triple-negative and Her2 positive breast cancer patients. BMC Cancer. 2013 Sep. 24; 13:437

Thor A D, Edgerton S M, Jones F E: Subcellular localization of the HER4 intracellular domain, 4ICD, identifies distinct prognostic outcomes for breast cancer patients. Am J Pathol. 2009, 175 (5): 1802-1809

Naresh A, Long W, Vidal G A, Wimley W C, Marrero L, Sartor C I, Tovey S, Cooke T G, Bartlett J M, Jones F E: The ERBB4/HER4 intracellular domain 4ICD is a BH3-only protein promoting apoptosis of breast cancer cells. Cancer Res. 2006, 66 (12): 6412-6420.

Chen X., Levkowitz G., Tzahar E., Karunagaran Lavi S. Ben-Baruch N., Leitner O., Ratzkini B. J., Bacus S. S, Yarden Y. An Immunological Approach Reveals Biological Differences between the Two NDF/Heregulin Receptors, ErbB-3 and ErbB-4. J Biol Chem. 1996 Mar. 29; 271(13):7620-7629

Bourquard T., Landomiel F., Reiter E., Crépieux P., W. Ritchie D., Azé J., Poupon A. Unraveling the molecular architecture of a G protein-coupled receptor/β-arrestin/Erk module complex. Sci Rep. 2015 Jun. 1; 5:10760

Webb B, Sali A. Protein Structure Modeling with MODELLER. Methods Mol Biol. 2017; 1654:39-54

Yu X., Zhang S., Jiang L., Cui Y., Li D., Wang D., Wang N., Fu L., Shi X., Li Z., Zhang L. Wang X. Structural basis for the neutralization of MERS-CoV by a human monoclonal antibody MERS-27. Sci. Rep. 2015 Aug. 18; 5:13133

Robin G., Sato Y., Desplancq D., Rochel N., Weiss E., Martineau P. Restricted diversity of antigen binding residues of antibodies revealed by computational alanine scanning of 227 antibody-antigen complexes. J Mol Biol. 2014 Nov. 11; 426(22):3729-3743

Bouyain S, Longo P A, Li S, Ferguson K M, Leahy D J. The extracellular region of ErbB4 adopts a tethered conformation in the absence of ligand. 2005 Oct. 18; 102(42): 15024-15029

The invention claimed is:

1. An isolated anti-HER4 antibody selected from a first, second, third, and fourth mab wherein:

the first mab, has:
(a) a heavy chain variable domain which comprises:
  a H-CDR1 having a sequence set forth as SEQ ID NO: 2;
  a H-CDR2 having a sequence set forth as SEQ ID NO: 3;
  a H-CDR3 having a sequence set forth as SEQ ID NO: 4;
(b) a light chain variable domain which comprises:
  a L-CDR1 having a sequence set forth as SEQ ID NO: 6;
  a L-CDR2 having a sequence set forth as SEQ ID NO: 7;
  a L-CDR3 having a sequence set forth as SEQ ID NO: 8;
the second mab, has:
(a) a heavy chain variable domain which comprises:
  a H-CDR1 having a sequence set forth as SEQ ID NO: 10;
  a H-CDR2 having a sequence set forth as SEQ ID NO: 11;
  a H-CDR3 having a sequence set forth as SEQ ID NO: 12;
(b) a light chain variable domain which comprises:
  a L-CDR1 having a sequence set forth as SEQ ID NO: 14;
  a L-CDR2 having a sequence set forth as SEQ ID NO: 15;
  a L-CDR3 having a sequence set forth as SEQ ID NO: 16;
the third mab, has:
(a) a heavy chain variable domain which comprises:
  a H-CDR1 having a sequence set forth as SEQ ID NO: 18;
  a H-CDR2 having a sequence set forth as SEQ ID NO: 19;
  a H-CDR3 having a sequence set forth as SEQ ID NO: 20;
(b) a light chain variable domain which comprises:
  a L-CDR1 having a sequence set forth as SEQ ID NO: 22;
  a L-CDR2 having a sequence set forth as SEQ ID NO: 23;
  a L-CDR3 having a sequence set forth as SEQ ID NO: 24;
and the fourth mab, has:
(a) a heavy chain variable domain which comprises:
  a H-CDR1 having a sequence set forth as SEQ ID NO: 26;
  a H-CDR2 having a sequence set forth as SEQ ID NO: 27;
  a H-CDR3 having a sequence set forth as SEQ ID NO: 28;
(b) a light chain variable domain which comprises:
  a L-CDR1 having a sequence set forth as SEQ ID NO: 30;
  a L-CDR2 having a sequence set forth as SEQ ID NO: 31;
  a L-CDR3 having a sequence set forth as SEQ ID NO: 32.

2. The isolated anti-HER4 antibody of claim 1 having a heavy chain identical to SEQ ID NO: 1, SEQ ID NO: 9, SEQ ID NO: 17 or SEQ ID NO: 25 and a light chain identical to SEQ ID NO: 5 SEQ ID NO: 13, SEQ ID NO: 21 or SEQ ID NO: 29.

3. The isolated anti-HER4 antibody of claim 1 having a heavy chain having at least 70, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or 100% of identity with SEQ ID NO: 1, SEQ ID NO: 9, SEQ ID NO: 17 or SEQ ID NO: 25 and a light chain having at least 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or 100% of identity with SEQ ID NO: 5, SEQ ID NO: 13, SEQ ID NO: 21 or SEQ ID NO: 29.

4. The isolated anti-HER4 antibody of claim 1 which is a chimeric antibody.

5. The isolated anti-HER4 antibody of claim 1 which is a humanized antibody.

6. The isolated anti-HER4 antibody of claim 1 which is selected from the group consisting of Fab, F (ab')2, Fab' and scFv.

7. The isolated anti-HER4 antibody of claim 1 which is conjugated to a cytotoxic moiety.

8. The isolated anti-HER4 antibody of claim 1 which is conjugated to a cytotoxic moiety selected from the group consisting of paclitaxel; cytochalasin B; gramicidin D; ethidium bromide; emetine; mitomycin; etoposide; tenoposide; vincristine; vinblastine; colchicin; doxorubicin; daunorubicin; dihydroxy anthracin dione; a tubulin-inhibitor; an antimitotic agent; dolastatin 10 or 15; irinotecan; mitoxantrone; mithramycin; actinomycin D; 1-dehydrotestosterone; a glucocorticoid; procaine; tetracaine; lidocaine; propranolol; puromycin; calicheamicin; an antimetabolite; an alkylating agent; a platinum compound; diphtheria toxin; diphtheria toxin A chain, ricin toxin, cholera toxin, a Shiga-like toxin, LT toxin, C3 toxin, Shiga toxin, pertussis toxin, tetanus toxin, soybean Bowman-Birk protease inhibitor, Pseudomonas exotoxin, alorin, saporin, modeccin, gelanin, abrin A chain, modeccin A chain, alpha-sarcin, an Aleurites fordii proteins, a dianthin proteins, a Phytolacca americana proteins, momordica charantia inhibitor, curcin, crotin, a sapaonaria officinalis inhibitor, gelonin, mitogellin, restrictocin, phenomycin, an enomycin toxins; ribonuclease (RNase); DNase I, Staphylococcal enterotoxin A; pokeweed antiviral protein; and Pseudomonas endotoxin.

9. The isolated anti-HER4 antibody of claim 8, wherein the tubulin-inhibitor is maytansine; and/or the antimitotic agent is monomethyl auristatin E or F; and/or the antimetabolite is methotrexate, 6 mercaptopurine, 6 thioguanine, cytarabine, fludarabin, 5 fluorouracil, decarbazine, hydroxyurea, asparaginase, gemcitabine, or cladribine; and/or the alkylating agent is mechlorethamine, thioepa, chlorambucil, melphalan, carmustine (BSNU), lomustine (CCNU), cyclophosphamide, busulfan, dibromomannitol, streptozotocin, dacarbazine (DTIC), procarbazine, or mitomycin C; and/or the platinum compound is cisplatin or carboplatin; duocarmycin A, duocarmycin SA, rachelmycin (CC-1065); and/or the antibiotic is dactinomycin, bleomycin, daunorubicin, doxorubicin, idarubicin, mithramycin, mitomycin, mitoxantrone, plicamycin, anthramycin (AMC)); or pyrrolo[2,1-c][1,4]-benzodiazepines (PDB); and/or the ricin toxin is ricin A or a deglycosylated ricin A chain toxin; and/or the Shiga-like toxin is SLT I, SLT II, SLT IIV; and/or the Phytolacca americana protein is PAPI, PAPII, or PAP-S.

10. The isolated anti-HER4 antibody of claim 1 which promotes cleavage of the 4ICD of the isoform JMaCYT1.

11. A pharmaceutical composition comprising the isolated anti-HER4 antibody of claim 1.

12. A method of treating cancer in a subject in need thereof comprising administering to the subject a therapeutically effective amount of the isolated anti-HER4 antibody of claim 1.

13. The method of claim 12, wherein the cancer is breast, ovarian, cervix, lung, urothelial, brain, or pancreatic cancer.

14. The method of claim 12, wherein the cancer is a metastatic cancer.

15. A nucleic acid molecule encoding the isolated anti-HER4 antibody of claim 1.

16. A chimeric antigen receptor which comprises the heavy chain variable domain and the light chain variable domain of the isolated anti-HER4 antibody of claim 1.

\* \* \* \* \*